United States Patent
Kozlowski et al.

(10) Patent No.: US 7,217,732 B2
(45) Date of Patent: May 15, 2007

(54) CANNABINOID RECEPTOR AGONISTS

(75) Inventors: Joseph A. Kozlowski, Princeton, NJ (US); Bandarpalle B. Shankar, Branchburg, NJ (US); Neng-Yang Shih, North Caldwell, NJ (US); Ling Tong, Warren, NJ (US)

(73) Assignee: Schering Corporation, Kenilworth, NJ (US)

( * ) Notice: Subject to any disclaimer, the term of this patent is extended or adjusted under 35 U.S.C. 154(b) by 166 days.

(21) Appl. No.: 10/464,174

(22) Filed: Jun. 17, 2003

(65) Prior Publication Data
US 2004/0044051 A1 Mar. 4, 2004

Related U.S. Application Data

(60) Provisional application No. 60/389,788, filed on Jun. 19, 2002.

(51) Int. Cl.
*A61K 31/404* (2006.01)
*C07D 209/04* (2006.01)

(52) U.S. Cl. ............... 514/418; 548/469; 548/484; 548/486; 548/511

(58) Field of Classification Search ............... 548/469, 548/484, 486, 511; 514/418, 415
See application file for complete search history.

(56) References Cited

U.S. PATENT DOCUMENTS

| | | |
|---|---|---|
| 4,466,965 A | 8/1984 | Stout et al. |
| 4,567,184 A | 1/1986 | Musser et al. |
| 5,332,820 A | 7/1994 | Duncia et al. |
| 5,338,753 A | 8/1994 | Burstein et al. |
| 5,462,960 A | 10/1995 | Barth et al. |
| 5,486,525 A | 1/1996 | Summers, Jr. et al. |
| 5,532,237 A | 7/1996 | Gallant et al. |
| 5,747,524 A | 5/1998 | Cullinan et al. |
| 5,925,768 A | 7/1999 | Barth et al. |
| 5,948,777 A | 9/1999 | Bender et al. |
| 5,990,170 A | 11/1999 | Della Valle et al. |
| 6,013,648 A | 1/2000 | Rinaldi et al. |
| 6,017,919 A | 1/2000 | Inaba et al. |

FOREIGN PATENT DOCUMENTS

| | | |
|---|---|---|
| DE | 19533644 | 9/1995 |
| EP | 0181568 | 5/1986 |
| EP | 0401030 | 12/1990 |
| EP | 0407217 | 1/1991 |
| EP | 1031571 | 8/2000 |
| EP | 1283039 | 2/2003 |
| JP | 06072979 | 3/1994 |
| WO | WO 93/21158 | 10/1993 |
| WO | WO 96/23783 | 8/1996 |
| WO | WO 97/03953 | 2/1997 |
| WO | WO 98/10763 | 3/1998 |
| WO | WO 98/31227 | 7/1998 |
| WO | WO 98/33769 | 8/1998 |
| WO | WO 98/41519 | 9/1998 |
| WO | WO 99/26612 | 6/1999 |
| WO | WO 99/36393 | 7/1999 |
| WO | WO 99/50245 | 10/1999 |
| WO | WO 00/06146 | 2/2000 |
| WO | WO 01/37826 | 5/2001 |
| WO | WO 01/44172 | 6/2001 |
| WO | WO 01/44239 | 6/2001 |
| WO | WO 01/64642 | 9/2001 |
| WO | WO 01/70753 | 9/2001 |
| WO | WO 01/74762 | 10/2001 |
| WO | WO 01/83460 | 11/2001 |
| WO | WO 02/062750 | 8/2002 |
| WO | WO 03/042174 | 5/2003 |

OTHER PUBLICATIONS

M. Curtin et al., "Discovery and Evaluation of a Series of 3-Acylindole Imidazopyridine Platelet-Activating Factor Antagonists", 41(1) *J. Med. Chem.* 74-95 (1998).

G. Hartman et al., "4-Substituted Thiophene—and Furan—2-Sulfonamides as topical carbonic anhydrase inhibitors" 35(21) *J. Med. Chem.* 3822-31 (1992).

G. Hartman et al., "Synthesis and derivatization of 4-(arylsulfonyl) thiophene—and—furan—2 sulfonamides", 27(2) *J. Heterocycl. Chem.* 127-34 (1990).

P. Cozzi et al., New N-(2-ethoxyethyl)-N-(4-phenoxybenzyl) dichloroacetamides as potent antiamoebic agents 18(3) *Eur. J. Med. Chem.* 203-208 (1983).

U.S. Appl. No. 03/024,398, for "Cannabinoid Receptor Ligands", filed Aug. 5, 2003.

U.S. Appl. No. 10/464,174, for "Cannabinoid Receptor Agonist", filed Jun. 17, 2003.

(Continued)

*Primary Examiner*—Golam M. M. Shameem
(74) *Attorney, Agent, or Firm*—William Y. Lee

(57) ABSTRACT

A compound of the formula

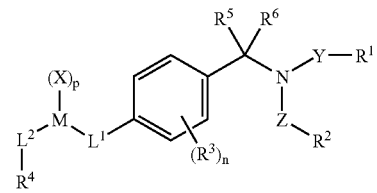

or a pharmaceutically acceptable salt thereof, wherein:
$R^1$, $R^2$, $R^3$, $R^4$, $R^5$, $R^6$, $L^1$, $L^2$, M, n, p, X, Y and Z are as described in the specification; pharmaceutical compositions thereof, methods of making said pharmaceutical compositions; and methods of use thereof.

28 Claims, No Drawings

OTHER PUBLICATIONS

R.G. Pertwee, "Pharmacology of Cannabinoid Receptor Ligands", Curr. Med. Chem 6(8), (1999), 635-664.

T.W. Greene et al. Protective Groups in Organic Synthesis (1981), Wiley, New York.

T. Higuchi and V. Stella, Pro-drugs as Novel Drug Delivery Systems (1975) 14 of the A.C.S. Symposium Series.

Bio reversible Carriers in Drug Design, (1987) Edward B. Roche, ed., American Pharmaceutical Association and Pergamon Press.

S. Berge et al., "Pharmaceutical Salts", Journal of Pharmaceutical Sciences (1977) 66(1) 1-19.

P. Gould, "Salt Selection for Basic Drugs", International J. of Pharmaceutics (1986) 33 201-217.

Anderson et al, The Practice of Medicinal Chemistry (1996), Academic Press, New York.

International Search Report for PCT/US 03/19245.

European Patent Office Communication Pursuant to Article 96(2) EPC (dated Nov. 1, 2006)-4 Pages.

CANNABINOID RECEPTOR AGONISTS

CROSS REFERENCE TO RELATED APPLICATION

This application claims priority to U.S. Provisional Application No. 60/389,788, filed Jun. 19, 2002.

FIELD OF THE INVENTION

The present invention relates to cannabinoid receptor agonists which bind to cannabinoid ($CB_2$) receptors. Compounds according to the present invention generally exhibit anti-inflammatory and immunomodulatory activity and are useful in treating conditions characterized by inflammation and immunomodulatory irregularities. Examples of conditions which can be treated include, but are not limited to, rheumatoid arthritis, asthma, allergy, psoriasis, Crohn's disease, systemic lupus erythematosus, multiple sclerosis, diabetes, cancer, glaucoma, osteoporosis, renal ischemia, cerebral stroke, cerebral ischemia, and nephritis. The invention also relates to pharmaceutical compositions containing said compounds.

BACKROUND OF THE INVENTION

Cannabinoid receptors belong to the superfamily of G-protein coupled receptors. They are classified into the predominantly neuronal $CB_1$ receptors and the predominantly peripheral $CB_2$ receptors. These receptors exert their biological actions by modulating adenylate cyclase and $Ca^{+2}$ and $K^+$ currents. While the effects of $CB_1$ receptors are principally associated with the central nervous system, $CB_2$ receptors are believed to have peripheral effects related to bronchial constriction, immunomodulation and inflammation.

Various compounds have reportedly been developed which interact with $CB_2$ receptors and/or which have, inter alia, anti-inflammatory activity associated with cannabinoid receptors. See, e.g., U.S. Pat. Nos. 5,338,753, 5,462,960, 5,532,237, 5,925,768, 5,948,777, 5,990,170, 6,013,648 and 6,017,919.

SUMMARY OF THE INVENTION

The present invention relates to compounds of formula I:

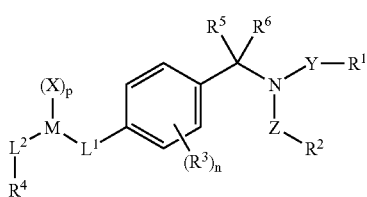

or a pharmaceutically acceptable salt or solvate thereof; wherein:

$R^1$ is selected from the group consisting of hydrogen, substituted or unsubstituted alkyl, substituted or unsubstituted alkenyl, haloalkyl, —$N(R^7)_2$, substituted or unsubstituted cycloalkyl, substituted or unsubstituted cycloheteroalkyl, substituted or unsubstituted aryl, and substituted or unsubstituted heteroaryl, wherein the term "substituted" means being substituted with $(X)_p$;

$R^2$ is selected from the group consisting of hydrogen, substituted or unsubstituted alkyl, substituted or unsubstituted alkenyl, haloalkyl, —$N(R^7)_2$, substituted or unsubstituted cycloalkyl, substituted or unsubstituted cycloheteroalkyl, substituted or unsubstituted aryl, and substituted or unsubstituted heteroaryl, wherein the term "substituted" means being substituted with $(X)_p$;

$R^3$ is selected from the group consisting of alkyl, heteroalkyl, aryl, heteroaryl, Br, Cl, F, $CF_3$, $OCF_2H$, $OCF_3$, and alkoxy, wherein $R^3$ can be the same or different and is independently selected when n>1;

$R^4$ is selected from the group consisting of H, substituted or unsubstituted alkyl, substituted or unsubstituted alkenyl, substituted or unsubstituted cycloalkyl, substituted or unsubstituted cycloheteroalkyl, substituted or unsubstituted aryl, and substituted or unsubstituted heteroaryl, wherein the term "substituted" means being substituted with $(X)_p$;

$R^5$ and $R^6$, which can be the same or different, are independently selected from the group consisting of H, substituted or unsubstituted alkyl, substituted or unsubstituted alkenyl, substituted or unsubstituted cycloalkyl, substituted or unsubstituted cycloheteroalkyl, substituted or unsubstituted aryl, and substituted or unsubstituted heteroaryl, wherein the term "substituted" means being substituted with $(X)_p$;

$R^7$ is selected from the group consisting of hydrogen, substituted or unsubstituted alkyl, substituted or unsubstituted alkenyl, haloalkyl, substituted or unsubstituted cycloalkyl, substituted or unsubstituted cycloheteroalkyl, substituted or unsubstituted aryl, and substituted or unsubstituted heteroaryl, or two $R^7$ groups can form a ring of 4–7 carbon atoms, wherein the term "substituted" means being substituted with $(X)_p$;

$L^1$ is selected from the group consisting of —$C(R^2)_2$—, —$C(O)$—, —$(CH(OR^2))$—, —$S(O_2)$—, —$S(O)$—, —$S$—, —$O$—, —$N(R^2)$—, —$C(O)N(H)$—, —$N(H)C(O)$—, —$CF_2$—, —$CH=N$—$O$—$R^2$ and —$CH(NHOR^2)$—;

$L^2$ is selected from the group consisting of a covalent bond, —$CH_2$—, —$CH(CH_3)$—, —$C(CH_3)_2$—, —$CH=N$—$O$—$R^2$, —$S(O_2)$—, —$S(O)$—, —$S$—, —$C(O)$—, —$O$—, —$N(R^2)$—, —$C(O)N(H)$— and —$N(H)C(O)$—;

M is a heteroaryl moiety;

n is 0–4;

p is 0–5;

X can be the same or different and is selected from the group consisting of Br, Cl, F, $CF_3$, OH, $OCF_2H$, $OCF_3$, alkoxy, alkyl, cycloalkyl, —O-cycloalkyl, heteroalkyl, —$C(O)N(R^7)_2$, —$S(O_2)R^2$, and —$OS(O_2)R^2$, wherein X is independently selected when p>1;

Y is selected from the group consisting of a covalent bond, —$CH_2$—, —$S(O_2)$—, and —$C(O)$—; and Z is selected from the group consisting of a covalent bond, —$CH_2$—, —$S(O_2)$—, and —$C(O)$—, with the following provisos:

when $L^2$ is a covalent bond, M is directly linked to $R^4$;

when Y is a covalent bond, $R^1$ is directly linked to the nitrogen atom shown in formula I; and when Z is a covalent bond, $R^2$ is directly linked to the nitrogen atom shown in formula I.

Another aspect of the invention relates to a pharmaceutical composition comprising one or more compounds of formula I, preferably with a pharmaceutically acceptable carrier.

Another aspect of the invention relates to a method of preparing a pharmaceutical composition comprising one or more compounds of formula I, said method comprising contacting one or more compounds of formula I with one or more pharmaceutically acceptable carriers.

Another aspect of the invention relates to a method of stimulating cannabinoid $CB_2$ receptors in a patient in need of such stimulation comprising administering to a patient having $CB_2$ receptors a $CB_2$ receptor stimulating amount of one or more compounds of formula I.

Another aspect of the invention relates to a method of treating cancer, to inflammatory diseases, immunomodulatory diseases, or respiratory diseases comprising administering to a patient in need of such treatment one or more compounds of formula I.

Another aspect of the invention relates to a method of treating multiple sclerosis comprising co-administering or combining with the compound of formula I one or more additional agents which may be the same or different and are independently selected from the group consisting of Interferon B1a, Interferon B1b and glatiramer acetate.

Another aspect of the invention relates to a kit for treating cancer, inflammatory diseases, immunomodulatory diseases, and respiratory diseases comprising in one or more containers an active compound for stimulating cannabinoid $CB_2$ receptors in a patient in need of such stimulation which comprises in one or more containers, one or more compounds according to claim 1 in one or more pharmaceutically acceptable carriers.

DETAILED DESCRIPTION

The present invention relates to cannabinoid receptor antagonist compounds of formula I:

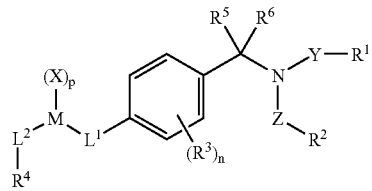

or a pharmaceutically acceptable salt or solvate thereof; wherein $R^1$, $R^2$, $R^3$, $R^4$, $R^5$, $R^6$, $L^1$, $L^2$, M, n, p, X, Y, and Z are as defined above.

$L^1$ preferably represents —$(SO_2)$—, —$CH_2$—, or —CH(OH)—.

$L^2$ preferably represents —$(SO_2)$—.

n is preferably 0.

$R^1$ preferably represents $CH_3$ or $CF_3$.

$R^2$ preferably represents H.

$R^4$ preferably represents furanyl, pyridyl, thienyl, quinolyl or fluorophenyl.

$R^5$ and $R^6$, which can be the same or different, preferably represent H or $CH_3$.

X preferably represents Cl or F.

M is preferably selected from the group consisting of indolyl, benzofuranyl, dihydrobenzofuranyl, furanyl, thienyl, pyridinyl, aryl and pyridinyl-N-oxide. In another embodiment, M is selected from the group consisting of pyridinyl, pyridinyl-N-oxide, furanyl and thienyl.

Y preferably represents —$S(O_2)$— or —$C(O)$—.

Exemplary compounds of formula 1 are set forth in Table I below wherein Z is a covalent bond, n is 0, $R^2$ is H, and $R^1$, $R^4$, $R^5$, $R^6$, M, $L^1$, $L^2$, p, Y and X are defined in Table 1 below as follows:

TABLE I

| # | $R^1$ | $R^5$, $R^6$ | $R^4$ (with liking point to $L^2$) | M (with linking points to $L^1$, $L^2$ and Z) | $L^1$ | $L^2$ | Y | p, X |
|---|---|---|---|---|---|---|---|---|
| 1 | $CH_3$ | $CH_3$, H | 2-fluorophenyl | indolyl | —$S(O_2)$— | —$S(O_2)$— | —$S(O_2)$— | 0 |
| 2 | $CF_3$ | $CH_3$, H | 2-fluorophenyl | indolyl | —$S(O_2)$— | —$S(O_2)$— | —$C(O)$— | 0 |
| 3 | $CF_3$ | $CH_3$, H | 2-fluorophenyl | furanyl | —$S(O_2)$— | —$S(O_2)$— | —$S(O_2)$— | 0 |

TABLE I-continued

| # | $R^1$ | $R^5, R^6$ | $R^4$ (with linking point to $L^2$) | M (with linking points to $L^1$, $L^2$ and Z) | $L^1$ | $L^2$ | Y | p, X |
|---|---|---|---|---|---|---|---|---|
| 4 | $CF_3$ | $CH_3$, H | 4-methoxyphenyl | indole (N-$L^2$, 2-$L^1$) | —S($O_2$)— | —S($O_2$)— | —C(O)— | 0 |
| 5 | $CH_3$ | H, H | 4-methoxyphenyl | indole (N-$L^2$, 2-$L^1$) | —S($O_2$)— | —S($O_2$)— | —S($O_2$)— | 0 |
| 6 | $CH_3$ | $CH_3$, H | 2-fluorophenyl | 5-X-indole (N-$L^2$, 2-$L^1$) | —S($O_2$)— | —S($O_2$)— | —S($O_2$)— | 1, Cl |
| 7 | $CF_3$ | $CH_3$, H | 2-fluorophenyl | 5-X-indole (N-$L^2$, 2-$L^1$) | —S($O_2$)— | —S($O_2$)— | —S($O_2$)— | 1, Cl |
| 8 | $CH_3$ | $CH_3$, H | phenyl | indole (N-$L^2$, 2-$L^1$) | —$CH_2$— | —S($O_2$)— | —S($O_2$)— | 0 |
| 9 | $CF_3$ | $CH_3$, H | 4-methoxyphenyl | indole (N-$L^2$, 2-$L^1$) | —CH(OH)— | —S($O_2$)— | —C(O)— | 0 |
| 10 | $CF_3$ | $CH_3$, H | phenyl | indole (N-$L^2$, 2-$L^1$) | —$CH_2$— | —S($O_2$)— | —C(O)— | 0 |
| 11 | $CF_3$ | $CH_3$, H | 4-methoxyphenyl | indole (N-$L^2$, 2-$L^1$) | —$CH_2$— | —S($O_2$)— | —C(O)— | 0 |

TABLE I-continued

| # | R$^1$ | R$^5$, R$^6$ | R$^4$ (with linking point to L$^2$) | M (with linking points to L$^1$, L$^2$ and Z) | L$^1$ | L$^2$ | Y | p, X |
|---|---|---|---|---|---|---|---|---|
| 12 | CH$_3$ | H, H | 2-F-phenyl | 5-X-indole (L$^1$ at 2, L$^2$ at N) | —S(O$_2$)— | —S(O$_2$)— | —S(O$_2$)— | 1, F |
| 13 | CH$_3$ | H, H | 2-F-phenyl | indole (L$^1$ at 2, L$^2$ at N) | —S(O$_2$)— | —S(O$_2$)— | —S(O$_2$)— | 0 |
| 14 | CF$_3$ | CH$_3$, H | 2-F-phenyl | furan (L$^1$ at 2, L$^2$ at 3) | —S(O$_2$)— | —S(O$_2$)— | —C(O)— | 0 |
| 15 | CF$_3$ | CH$_3$, H | 2-Cl-phenyl | furan (L$^1$ at 2, L$^2$ at 3) | —S(O$_2$)— | —S(O$_2$)— | —C(O)— | 0 |
| 16 | CF$_3$ | CH$_3$, H | 2-F-phenyl | indole (L$^1$ at 2, L$^2$ at N) | —S(O$_2$)— | —S(O$_2$)— | —S(O$_2$)— | 0 |
| 17 | CF$_3$ | CH$_3$, H | 2-Cl-phenyl | furan (L$^1$ at 2, L$^2$ at 3) | —S(O$_2$)— | —S(O$_2$)— | —S(O$_2$)— | 0 |
| 18 | CF$_3$ | CH$_3$, H | 2-F-phenyl | indole (L$^1$ at 2, L$^2$ at N) | —CH(OH)— | —S(O$_2$)— | —C(O)— | 0 |
| 19 | CF$_3$ | CH$_3$, H | 2-Cl-phenyl | pyridine (L$^1$ at 2, L$^2$ at 3) | —CH$_2$— | —S(O$_2$)— | —S(O$_2$)— | 0 |
| 20 | CF$_3$ | CH$_3$, H | 2-F-phenyl | indole (L$^1$ at 2, L$^2$ at N) | —CH$_2$— | —S(O$_2$)— | —C(O)— | 0 |

TABLE I-continued

| # | R¹ | R⁵, R⁶ | R⁴ (with linking point to L²) | M (with linking points to L¹, L² and Z) | L¹ | L² | Y | p, X |
|---|----|--------|-------------------------------|------------------------------------------|-----|-----|-----|------|
| 21 | CH₃ | CH₃, H | 2-Cl-phenyl | pyridine (N, L¹, L²) | —CH₂— | —S(O₂)— | —S(O₂)— | 0 |
| 22 | CF₃ | CH₃, H | 2-F-phenyl | indole (L¹, L²) | —CH₂— | —S(O₂)— | —S(O₂)— | 0 |
| 23 | CF₃ | CH₃, H | 2-Cl-phenyl | pyridine (N, L¹, L²) | —CH₂— | —S(O₂)— | —C(O)— | 0 |
| 24 | CH₃ | CH₃, CH₃ | 2-F-phenyl | indole (L¹, L²) | —S(O₂)— | —S(O₂)— | —S(O₂)— | 0 |
| 25 | CH₃ | H, H | 3-F-phenyl | indole (L¹, L²) | —S(O₂)— | —S(O₂)— | —S(O₂)— | 0 |
| 26 | CF₃ | CH₃, CH₃ | 2-F-phenyl | indole (L¹, L²) | —S(O₂)— | —S(O₂)— | —S(O₂)— | 0 |
| 27 | CF₃ | CH₃, H | pyridine | 2,3-dihydrobenzofuran (L¹, L²) | —S(O₂)— | —S(O₂)— | —C(O)— | 0 |
| 28 | CH₃ | H, H | 4-F-phenyl | indole (L¹, L²) | —S(O₂)— | —S(O₂)— | —S(O₂)— | 0 |
| 29 | CH₃ | H, H | 4-Cl-phenyl | indole (L¹, L²) | —S(O₂)— | —S(O₂)— | —S(O₂)— | 0 |

TABLE I-continued

| # | R¹ | R⁵, R⁶ | R⁴ (with linking point to L²) | M (with linking points to L¹, L² and Z) | L¹ | L² | Y | p, X |
|---|----|--------|-------------------------------|------------------------------------------|-----|-----|---|------|
| 30 | CH₃ | CH₃, H | 2-fluorophenyl | indole (L¹ at 2, L² at N) | —CH₂— | —S(O₂)— | —S(O₂)— | 0 |
| 31 | CF₃ | H, H | 2-fluorophenyl | indole (L¹ at 2, L² at N) | —S(O₂)— | —S(O₂)— | —S(O₂)— | 0 |
| 32 | CF₃ | CH₃, H | 4-methoxyphenyl | indole (L¹ at 2, L² at N) | —C(O)— | —S(O₂)— | —C(O)— | 0 |
| 33 | CF₃ | CH₃, H | phenyl | indole (L¹ at 3, L² at N) | CH=N—O—CH₃ | —S(O₂)— | —C(O)— | 0 |
| 34 | CH₃ | CH₃, H | 4-methoxyphenyl | indole (L¹ at 3, L² at N) | —C(O)— | —S(O₂)— | —S(O₂)— | 0 |
| 35 | CF₃ | CH₃, CH₃ | pyridin-2-yl | indole (L¹ at 2, L² at N) | —S(O₂)— | —S(O₂)— | —S(O₂)— | 0 |
| 36 | CF₃ | CH₃, H | 3-fluorophenyl | indole (L¹ at 2, L² at N) | —S(O₂)— | —S(O₂)— | —S(O₂)— | 0 |
| 37 | CH₃ | CH₃, H | 4-(trifluoromethoxy)phenyl | indole (L¹ at 2, L² at N) | —S(O₂)— | —S(O₂)— | —S(O₂)— | 0 |

TABLE I-continued

| # | R¹ | R⁵, R⁶ | R⁴ (with linking point to L²) | M (with linking points to L¹, L² and Z) | L¹ | L² | Y | p, X |
|---|----|--------|-------------------------------|------------------------------------------|----|----|----|------|
| 38 | CH₃ | CH₃, H | 4-Cl-phenyl | pyridine (L¹, L²) | CH=N-O-CH₃ | —O— | —S(O₂)— | 0 |
| 39 | | H, H | 2-F-phenyl | indole (L¹, L²) | —S(O₂)— | —S(O₂)— | —S(O₂)— | 0 |
| 40 | CF₃ | H, H | 4-Cl-phenyl | indole (L¹, L²) | —S(O₂)— | —S(O₂)— | —C(O)— | 0 |
| 41 | CF₃ | CH₃, H | 2-Cl-phenyl | indole with X (L¹, L²) | —S(O₂)— | —S(O₂)— | —S(O₂)— | 1, Cl |
| 42 | CH₃ | H, H | 3-Cl-phenyl | indole (L¹, L²) | —S(O₂)— | —S(O₂)— | —S(O₂)— | 0 |
| 43 | CF₃ | CH₃, H | phenyl | indole (L¹, L²) | —C(O)— | —S(O₂)— | —C(O)— | 0 |
| 44 | CH₃ | CH₃, H | 4-OCH₃-phenyl | indole (L¹, L²) | —C(O)— | —S(O₂)— | —S(O₂)— | 0 |
| 45 | CH₃ | CH₃, H | 4-Cl-phenyl | pyridine (L¹, L²) | —CH₂— | —O— | —S(O₂)— | 0 |

TABLE I-continued

| # | R¹ | R⁵, R⁶ | R⁴ (with linking point to L²) | M (with linking points to L¹, L² and Z) | L¹ | L² | Y | p, X |
|---|----|--------|-------------------------------|----------------------------------------|----|----|----|------|
| 46 | CF₃ | CH₃, H | pyridin-3-yl | indole (X on N, L¹ at 5-position, L² at 4-position) | —S(O₂)— | —SO— | —C(O)— | CH₃ |
| 47 | CF₃ | CH₃, H | 2-chlorophenyl | pyridine N-oxide (L¹, L²) | —CH₂— | —S(O₂)— | —C(O)— | 0 |
| 48 | CF₃ | CH₃, H | 4-chlorophenyl | pyridin-2,3-diyl | —C(O)— | —O— | —C(O)— | 0 |
| 49 | CF₃ | H, H | 4-fluorophenyl | indol-1,2-diyl | —S(O₂)— | —S(O₂)— | —S(O₂)— | 0 |
| 50 | CF₃ | H, H | 3-fluorophenyl | indol-1,2-diyl | —S(O₂)— | —S(O₂)— | —S(O₂)— | 0 |
| 51 | CF₃ | CH₃, H | 2-fluorophenyl | indol-1,2-diyl | —S(O₂)— | —C(O)— | —C(O)— | 0 |
| 52 | CF₃ | CH₃, H | 4-chlorophenyl | pyridin-2,3-diyl | —C(O)— | —S— | —C(O)— | 0 |
| 53 | CH₃ | CH₃, H | 4-chlorophenyl | pyridin-2,3-diyl | —C(O)— | —S— | —S(O₂)— | 0 |
| 54 | CF₃ | H, H | 4-chlorophenyl | indol-1,2-diyl | —S(O₂)— | —S(O₂)— | —S(O₂)— | 0 |

TABLE I-continued
| # | R¹ | R⁵, R⁶ | R⁴ (with liking point to L²) | M (with linking points to L¹, L² and Z) | L¹ | L² | Y | p, X |
|---|---|---|---|---|---|---|---|---|
| 55 | CH₃ | H, H | 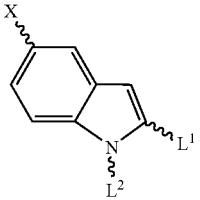 | 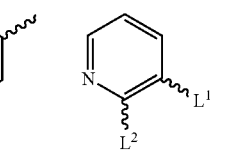 | —S(O₂)— | —CH₂— | —S(O₂)— | 1, F |
| 56 | CH₃ | CH₃, H | 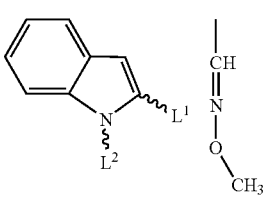 | 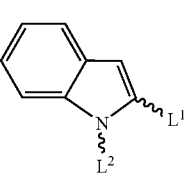 | —C(O)— | —S(O₂)— | —S(O₂)— | 0 |
| 57 | CH₃ | CH₃, H | 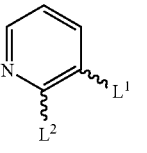 | 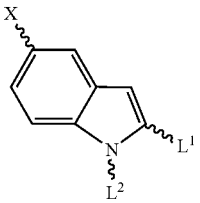 | | —S(O₂)— | —S(O₂)— | 0 |
| 58 | CH₃ | CH₃, H | 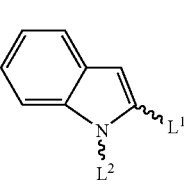 | 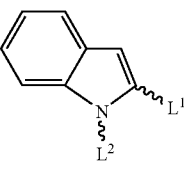 | —S(O₂)— | —CH₂— | —S(O₂)— | 0 |
| 59 | CH₃ | CH₃, H | | | —C(O)— | —O— | —S(O₂)— | 0 |
| 60 | CH₃ | CH₃, H | | | —S(O₂)— | —C(O)— | —S(O₂)— | 1, Cl |
| 61 | | H, H | | | —S(O₂)— | —S(O₂)— | —S(O₂)— | 0 |
| 62 | | H, H | | | —S(O₂)— | —S(O₂)— | —S(O₂)— | 0 |

TABLE I-continued

| # | R¹ | R⁵, R⁶ | R⁴ (with linking point to L²) | M (with linking points to L¹, L² and Z) | L¹ | L² | Y | p, X |
|---|----|--------|-------------------------------|-----------------------------------------|----|----|---|------|
| 63 | $CF_3$ | H, H | 3-chlorophenyl | indole (N-L², 2-L¹) | —S($O_2$)— | —S($O_2$)— | —S($O_2$)— | 0 |
| 64 | $CF_3$ | $CH_3$, H | 2-pyridyl | 2,3-dihydrobenzofuran | —S($O_2$)— | —S— | —C(O)— | 0 |
| 65 | $CF_3$ | H, H | 2-fluorophenyl | indole (with X) | —S($O_2$)— | —$CH_2$— | —S($O_2$)— | 1, F |
| 66 | 4-Cl-phenyl | $CH_3$, H | 4-chlorophenyl | indole | —S($O_2$)— | —$CH_2$— | —$CH_2$— | F |
| 67 | $CF_3$ | $CH_3$, H | phenyl | thiophene | —S($O_2$)— | —S($O_2$)— | —C(O)— | F |

In a preferred embodiment, the compound of the present invention is represented by the formula:

In another preferred embodiment, the compound of the present invention is represented by the formula:

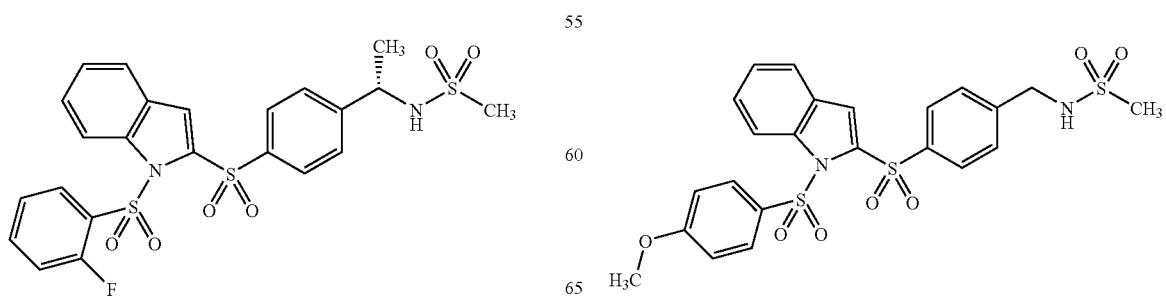

In another preferred embodiment, the compound of the present invention is represented by the formula:

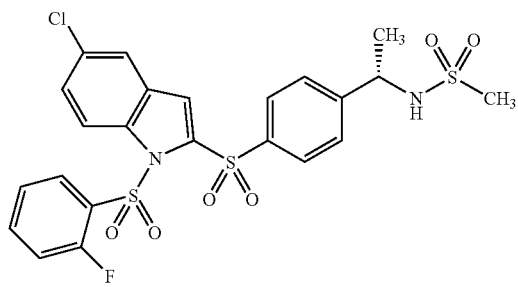

In another preferred embodiment, the compound of the present invention is represented by the formula:

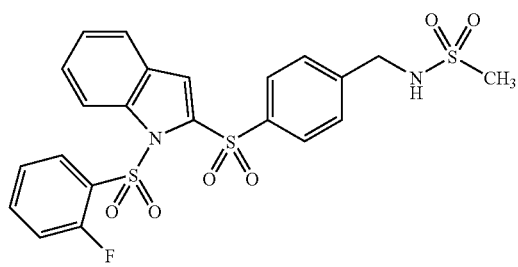

In another preferred embodiment, the compound of the present invention is represented by the formula:

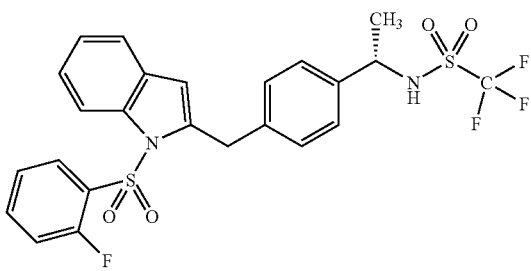

In another preferred embodiment, the compound of the present invention is represented by the formula:

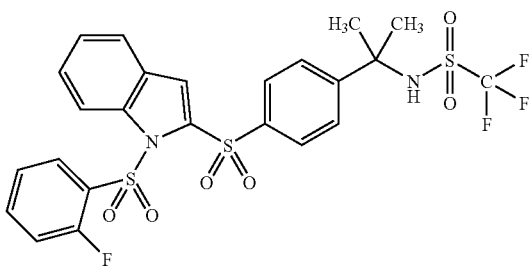

In another preferred embodiment, the compound of the present invention is represented by the formula:

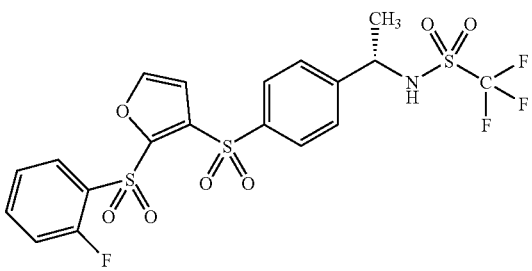

In another preferred embodiment, the compound of the present invention is represented by the formula:

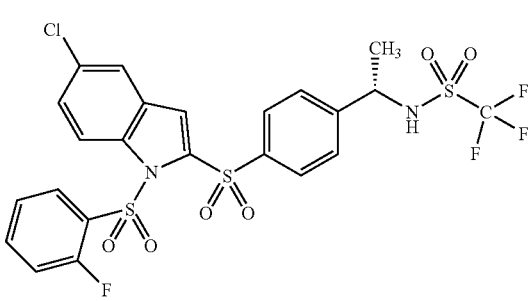

In another preferred embodiment, the compound of the present invention is represented by the formula:

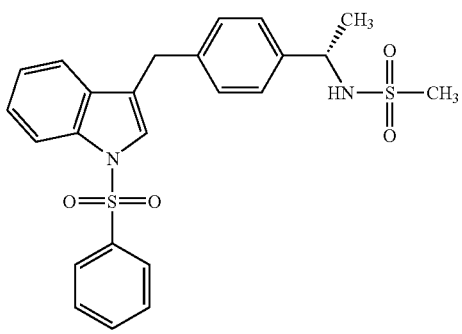

In another preferred embodiment, the compound of the present invention is represented by the formula:

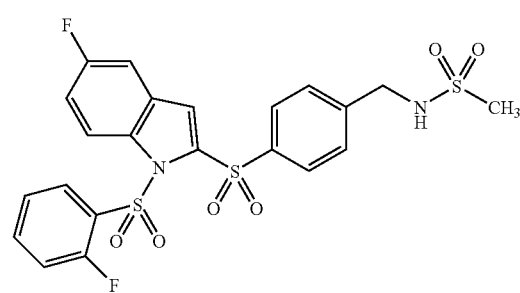

In another preferred embodiment, the compound of the present invention is represented by the formula:

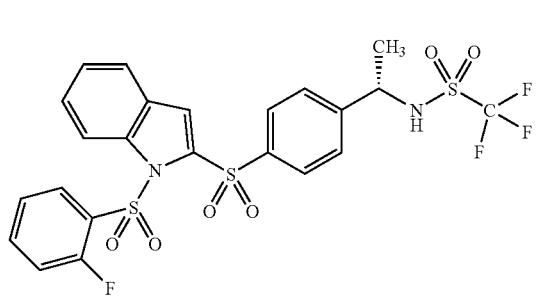

In another preferred embodiment, the compound of the present invention is represented by the formula:

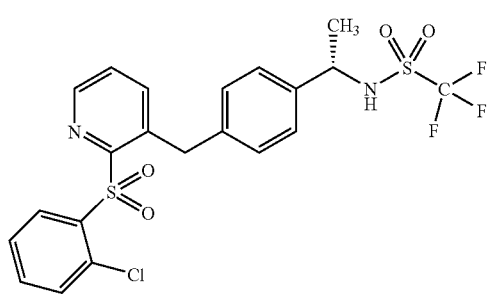

In another preferred embodiment, the compound of the present invention is represented by the formula:

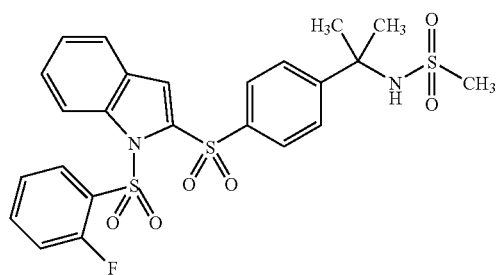

In another preferred embodiment, the compound of the present invention is represented by the formula:

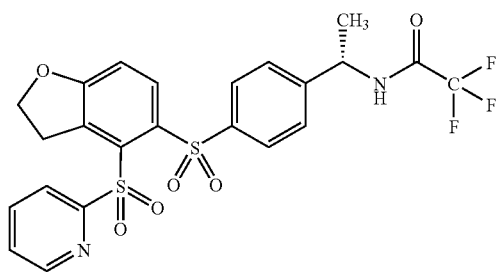

In another preferred embodiment, the compound of the present invention is represented by the formula:

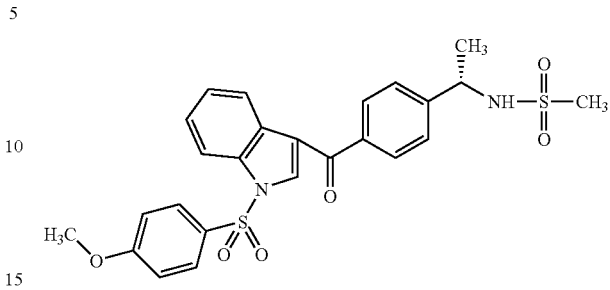

In another preferred embodiment, the compound of the present invention is represented by the formula:

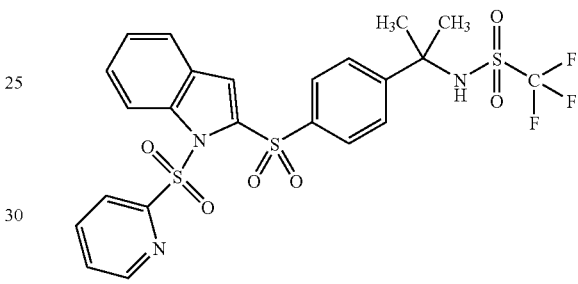

In another preferred embodiment, the compound of the present invention is represented by the formula:

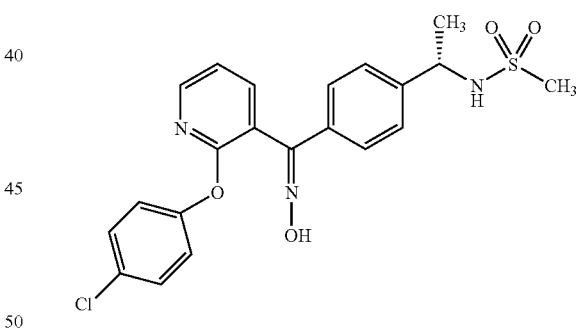

In another preferred embodiment, the compound of the present invention is represented by the formula:

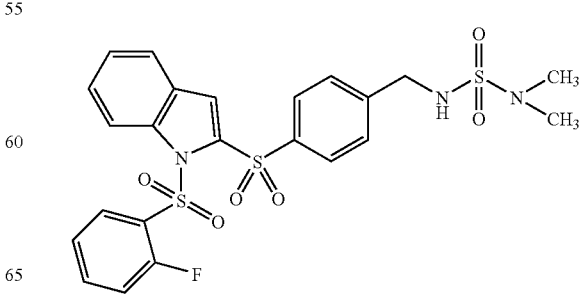

In yet another preferred embodiment, the compound of the present invention is represented by the formula:

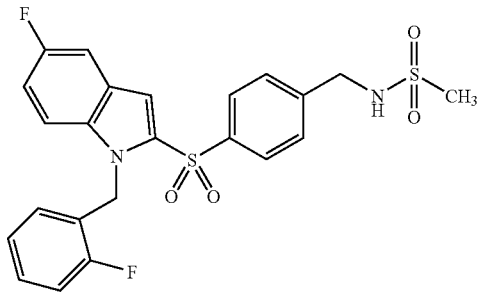

Cannabinoid receptor agonists according to the present invention can have anti-inflammatory activity and/or immunomodulatory activity and are useful in the treatment of various medical conditions including, e.g., rheumatoid arthritis, systemic lupus erythematosus, multiple sclerosis, glaucoma, diabetes, osteoporosis, renal ischemia, cerebral stroke, cerebral ischemia, nephritis, psoriasis, allergy, inflammatory disorders of the lungs and gastrointestinal tract such as Crohn's disease, and respiratory tract disorders such as reversible airway obstruction, asthma and bronchitis.

Except where stated otherwise, the following definitions apply throughout the present specification and claims. These definitions apply regardless of whether a term is used by itself or in combination with other terms. Hence the definition of "alkyl" applies to "alkyl" as well as the "alkyl" portions of "alkoxy", "haloalkyl", etc.

"Alkyl" means an aliphatic hydrocarbon group which may be straight or branched and comprising 1 to about 20 carbon atoms in the chain. Preferred alkyl groups contain 1 to about 12 carbon atoms in the chain. More preferred alkyl groups contain 1 to about 6 carbon atoms in the chain. Branched alkyl means that one or more lower alkyl groups such as methyl, ethyl or propyl, are attached to a linear alkyl chain. "Lower alkyl" means a group having about 1 to about 6 carbon atoms in the chain which may be straight or branched. Preferred alkyl groups in the present invention are lower alkyl groups. Non-limiting examples of suitable alkyl groups include methyl, ethyl, n-propyl, isopropyl, n-butyl, t-butyl, n-pentyl, heptyl, nonyl, decyl, trifluoromethyl and cyclopropylmethyl.

"Alkenyl" means an aliphatic hydrocarbon group containing at least one carbon-carbon double bond and which may be straight or branched and comprising 2 to 15 carbon atoms in the chain. Preferred alkenyl groups have 2 to 2 carbon atoms in the chain; and more preferably 2 to 6 carbon atoms in the chain. Branched alkyenyl means that one or more lower alkyl groups such as methyl, ethyl or propyl, are attached to a linear alkenyl chain. "Lower alkenyl" means 2 to 6 carbon atoms in the chain which may be straight or branched. Non-limiting examples of suitable alkenyl groups include ethenyl, propenyl, n-butenyl, 3-methylbut-2-enyl, and n-pentenyl.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine or bromine, and more preferred are fluorine and chlorine.

"Haloalkyl" or "halogenated alkyl" means alkyl having one or more halo atom substituents. Non-limiting examples include —$CH_2Cl$, —$CHCl_2$, —$CCl_3$, —$CH_2F$, —$CHF_2$, —$CF_3$, —$CH_2$—$CH_2Cl$, —$CH_2$—$CHCl_2$, and —$CHCl$—$CH_2Cl$.

"Heteroalkyl" means straight or branched alkyl chain as defined above comprising 1 or more heteroatoms, which can be the same or different, and are independently selected from the group consisting of N, O and S.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, phenylethyl and naphthalenylmethyl. The aralkyl is linked to an adjacent moiety through the alkyl.

"Alkylaryl" means an alkyl-aryl-group in which the alkyl and aryl are as previously described. Preferred alkylaryls comprise a lower alkyl group. Non-limiting examples of suitable alkylaryl groups include tolyl and xylyl. The alkylaryl is linked to an adjacent moiety through the aryl.

"Aralkenyl" means an aryl-alkenyl-group in which the aryl and alkenyl groups are as previously described. Preferred aralkenyls contain a lower alkenyl group. Non-limiting examples of suitable aralkenyl groups include phenylethenyl and naphthylethenyl. The aralkenyl is linked to an adjacent moiety through the alkenyl.

"Alkoxy" means an alkyl-O— group in which the alkyl group is as previously described. Non-limiting examples of suitable alkoxy groups include methoxy, ethoxy, n-propoxy and isopropoxy. The alkyl group is linked to an adjacent moiety through the ether oxygen.

"Aryloxy" means an aryl-O— group in which the aryl group is as previously described. Non-limiting examples of suitable aryloxy groups include phenoxy and naphthoxy. The aryl group is linked to an adjacent moiety through the ether oxygen.

"Aralkyloxy" means an aralkyl-O— group in which the aralkyl group is as previously described. Non-limiting examples of suitable aralkyloxy groups include benzyloxy and naphthalenylmethoxy. The aralkyl group is linked to an adjacent moiety through the ether oxygen.

"Alkylamino" means an —$NH_2$ or —$NH_3^+$ group in which one or more of the hydrogen atoms on the nitrogen is replaced by an alkyl group as defined above.

"Arylamino" means an —$NH_2$ or —$NH_3^+$ group in which one or more of the hydrogen atoms on the nitrogen is replaced by an aryl group as defined above.

"Alkylthio" means an alkyl-S— group in which the alkyl group is as previously described. Non-limiting examples of suitable alkylthio groups include methylthio, ethylthio and isopropylthio. The alkyl is linked to an adjacent moiety through the sulfur.

"Arylthio" means an aryl-S— group in which the aryl group is as previously described. Non-limiting examples of suitable arylthio groups include phenylthio and naphthylthio. The aryl is linked to an adjacent moiety through the sulfur.

"Aralkylthio" means an aralkyl-S— group in which the aralkyl group is as previously described. Non-limiting example of a suitable aralkylthio group is benzylthio. The aralkyl is linked to an adjacent moiety through the sulfur.

"Alkoxycarbonyl" means an alkyl-O—C(O)— group. Non-limiting examples of suitable alkoxycarbonyl groups include methoxycarbonyl and ethoxycarbonyl. The alkoxy is linked to an adjacent moiety through the carbonyl.

"Aryloxycarbonyl" means an aryl-O—C(O)— group. Non-limiting examples of suitable aryloxycarbonyl groups include phenoxycarbonyl and naphthoxycarbonyl. The aryloxy is linked to an adjacent moiety through the carbonyl.

"Aralkoxycarbonyl" means an aralkyl-O—C(O)— group. Non-limiting example of a suitable aralkoxycarbonyl group is benzyloxycarbonyl. The aralkoxy is linked to an adjacent moiety through the carbonyl.

"Alkylsulfonyl" means an alkyl-S(O$_2$)— group. The alkyl is linked to an adjacent moiety through the sulfonyl. Preferably, the alkyl portion of the "alkylsulfonyl" is lower alkyl.

"Alkylsulfinyl" means an alkyl-S(O)— group. The alkyl is linked to an adjacent moiety through the sulfinyl. Preferably, the alkyl portion of the "alkylsulfinyl" is lower alkyl.

"Arylsulfonyl" means an aryl-S(O$_2$)— group. The aryl is linked to an adjacent moiety through the sulfonyl.

"Aryl" means an aromatic monocyclic or multicyclic ring system comprising 6 to 14 ring carbon atoms, preferably 6 to 10 ring carbon atoms. The aryl group can be optionally substituted with one or more "ring system substituents" which may be the same or different, and are as defined herein. Non-limiting examples of suitable aryl groups include phenyl and naphthyl.

"Heteroaryl" represents cyclic aromatic groups of 5 or 6 ring atoms or bicyclic groups of 11 to 12 ring atoms having 1 or 2 heteroatoms independently selected from O, S or N, said heteroatom(s) interrupting a carbocyclic ring structure and having a sufficient number of delocalized pi electrons to provide aromatic character, provided that the rings do not contain adjacent oxygen and/or sulfur atoms. Preferred heteroaryls contain 5 to 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. Nitrogen atoms can form an N-oxide. All regioisomers are contemplated, e.g., 2-pyridyl, 3-pyridyl and 4-pyridyl. Useful 6-membered heteroaryl groups include pyridyl, pyrimidinyl, pyrazinyl, pyridazinyl and the like and the N-oxides thereof. Useful 5-membered heteroaryl rings include furyl, thienyl, pyrrolyl, thiazolyl, isothiazolyl, imidazolyl, pyrazolyl, isoxazolyl and the like. Useful bicyclic groups include benzofused ring systems derived from the heteroaryl groups named above, e.g. quinolyl, phthalazinyl, quinazolinyl, benzofuranyl, benzothienyl, indolyl and the like.

"Ring system substituent" means a substituent attached to an aromatic or nonaromatic ring system which, for example, replaces an available hydrogen on the ring system. Ring system substituents may be the same or different, each being independently selected from the group consisting of aryl, heteroaryl, aralkyl, alkylamino, arylamino, alkylaryl, aralkenyl, heteroaralkyl, alkylheteroaryl, heteroaralkenyl, hydroxy, hydroxyalkyl, alkoxy, aryloxy, aralkoxy, aralkyloxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, $Y_1Y_2N$—, $Y_1Y_2$N-alkyl-, $Y_1Y_2$NC(O)— and $Y_1Y_2NSO_2$—, wherein $Y_1$ and $Y_2$ may be the same or different and are independently selected from the group consisting of hydrogen, alkyl, aryl, and aralkyl.

"Cycloalkyl" means a non-aromatic mono- or multicyclic fused ring system comprising 3 to 10 ring carbon atoms, preferably 3 to 7 ring carbon atoms, more preferably 3 to 6 ring carbon atoms. The cycloalkyl can be optionally substituted with one or more "ring system substituents" which may be the same or different, and are as defined above. Non-limiting examples of suitable monocyclic cycloalkyls include cyclopropyl, cyclobutyl, cyclopentyl, cyclohexyl and the like. Non-limiting examples of suitable multicyclic cycloalkyls include 1-decalinyl, norbornenyl, adamantyl and the like.

"Cycloheteroalkyl" means a non-aromatic mono- or multicyclic fused ring system comprising 3 to 10 ring carbon atoms, preferably 3 to 7 ring carbon atoms, more preferably 3 to 6 ring carbon atoms, wherein the cycloheteroalkyl has 1 or 2 heteroatoms independently selected from O, S or N, said heteroatom(s) interrupting a carbocyclic ring structure provided that the rings do not contain adjacent oxygen and/or sulfur atoms. The cycloheteroalkyl can be optionally substituted with one or more "ring system substituents" which may be the same or different, and are as defined above. Non-limiting examples of cycloheteroaryl groups include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like "Oxime" means a —CH(=NOR$^2$)— radical containing moiety, wherein R$^2$ is defined above.

The term "optionally substituted" means optional substitution with the specified groups, radicals or moieties.

The term "solvate" as used herein means an aggregate that consists of a solute ion or molecule with one or more solvent molecules, for example, a hydrate containing such ions.

As used herein, the terms "composition" and "formulation" are intended to encompass a product comprising the specified ingredients, as well as any product which results, directly or indirectly, from combination of the specified ingredients.

"Patient" includes mammals and other animals.

"Mammal" includes humans and other mammalian animals.

The term "pharmaceutically effective amount" or "therapeutically effective amount" is intended to mean an amount of a therapeutic agent of the compound of formula I that will have an effect on a tissue, system, animal or patient that is being sought by the administrator (such as a researcher, doctor or veterinarian), which includes alleviation of the symptoms of the condition or disease being treated and the prevention, slowing or halting of progression of the disease or condition, for example, the inflammatory, immunomodulatory or respiratory diseases discussed herein.

Prodrugs and solvates of the compounds of the invention are also contemplated within the scope of this invention. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

The compounds of formula I can form salts, solvates and prodrugs which are also within the scope of this invention. Reference to a compound of formula I herein is understood to include reference to salts, solvates and prodrugs thereof, unless otherwise indicated.

The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to, a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulforiates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1–19; P. Gould, *International J. of Pharmaceutics* (1986) 33 201–217; and Anderson et al, *The Practice of Medicinal Chemistry* (1996), Academic Press, New York). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula I, and salts and solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

The present invention also relates to a pharmaceutical composition comprising one or more compounds of formula I of this invention. Preferably, the pharmaceutical composition includes one or more pharmaceutically acceptable carriers. For preparing pharmaceutical compositions from the compounds described by this invention, inert, pharmaceutically acceptable carriers can be used. Such carriers can be either solid or liquid. Solid form preparations include powders, tablets, dispersible granules, capsules, cachets and suppositories. The powders and tablets can be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions can be found in A. Gennaro (ed.), *Remington's Pharmaceutical Sciences*, $18^{th}$ Edition, (1990), Mack Publishing Co., Easton, Pa.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. One example includes water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Another aspect of the invention relates to a method of stimulating cannabinoid $CB_2$ receptors in a patient comprising administering to a patient a $CB_2$ receptor stimulating amount of one or more compounds of formula I. The daily dose of a compound of formula I for stimulating cannabinoid $CB_2$ receptors in a patient can range from about 0.001 mg/kg to about 100 mg/kg of body weight per day, preferably from about 0.001 mg/kg to about 50 mg/kg of body weight per day, more preferably from about 0.001 mg/kg to about 10 mg/kg of body weight per day.

Another aspect of the invention relates to a method of treating cancer, inflammatory diseases, immunomodulatory diseases, or respiratory diseases comprising administering to a patient in need of such treatment one or more compounds of formula I. Preferably, the amount of compound I administered in this aspect of the invention is a therapeutically effective amount. The daily dose of a compound of formula I for treatment of a disease or condition can range from about 0.001 mg/kg to about 100 mg/kg of body weight per day, preferably from about 0.001 mg/kg to about 50 mg/kg of body weight per day, more preferably from about 0.001 mg/kg to about 10 mg/kg of body weight per day. For an average body weight of 70 kg, the dosage level can range from about 0.1 mg to about 700 mg of drug per day, given in a single dose or 2–4 divided doses. The exact dose, however, is determined by the attending clinician and is dependent on the potency of the compound administered, the age, weight, condition and response of the patient.

The compounds of the present invention can exhibit anti-inflammatory and/or immunomodulatory activity and are useful in the treatment of various medical conditions listed below. This utility is manifested as demonstrated by activity in the following assay.

Potential cannabinoid receptor ligands were screened for the ability to compete with [$^3$H] CP-55,940 for binding to recombinant cannabinoid receptors. Test compounds were serially diluted in Diluent Buffer (50 mM Tris pH 7.1, 1 mM EDTA, 3 mM $MgCl_2$, 0.1% BSA, 10% DMSO, 0.36% methyl cellulose (Sigma M-6385)) from stocks prepared in 100% DMSO. Aliquots (10 µl) were transferred into 96-well microtiter plates. Membrane preparations of recombinant human cannabinoid CB2 receptor (Receptor Biology #RB-HCB2) or recombinant human cannabinoid CB1 receptor (Receptor Biology #RB-HCB1) were diluted to 0.3 mg/ml in Binding Buffer (50 mM Tris pH 7.2, 1 mM EDTA, 3 mM $MgCl_2$, 0.1% BSA). Aliquots (50 µl) were added to each well of the microtiter plate. The binding reactions were initiated by addition of [$^3$H] CP-55,940 (New England Nuclear # NET 1051; specific activity=180 Ci/mmol available from New England Nuclear) to each well of the microtiter plate. Each 100 µl reaction mixture contained 0.48 nM [$^3$H] CP-55,940, 8 ug membrane protein in binding buffer containing 1% DMSO and 0.036% methyl cellulose. Following incubation for 2 hours at room temperature, the reaction mixtures were filtered through 0.5% polyethylenimine-coated GF/C filter plates (UniFilter-96, Packard) with a TomTec Mark 3U Harvester (Hamden, Conn.). The filter plate was washed 5 times with binding buffer, rotated 180°, then re-washed 5 times with binding buffer. Bound radioactivity was quantitated following addition of 30 µl of Packard Microscint 20 scintillant in a Packard TopCount NXT microplate scintillation counter. The resulting data was analyzed and Ki values for the compounds were determined using non-linear regression analysis performed using Prism 2.0b (from GraphPad, San Diego, Calif.). The data was analyzed and the cannabinoid receptor binding activity (Ki values) of the compounds were determined using GraphPad Prim.

For compounds of this invention, a range of Ki values ranging from about 0.1 nM to about 1 µM was observed. Preferred compounds 1–67 have Ki values ranging from about 0.1 nM to about 250 nM, preferably from about 0.1 to about 100 nM, more preferably from about 0.1 to about 10 nM.

It is contemplated that a compound of this invention can be useful in treating one or more of these diseases listed below.

Non-limiting examples of the cancer, inflammatory diseases, immunomodulatory diseases, and respiratory diseases include diseases selected from the group consisting of cutaneous T cell lymphoma, rheumatoid arthritis, systemic lupus erythematosus, multiple sclerosis, glaucoma, diabetes, osteoporosis, renal ischemia, myocardial infarction, cerebral stroke, cerebral ischemia, nephritis, hepatitis, glomerulonephritis, cryptogenic fibrosing aveolitis, psoriasis, atopic dermatitis, vasculitis, allergy, seasonal allergic rhinitis, Crohn's disease, inflammatory bowel disease, reversible airway obstruction, adult respiratory distress syndrome, asthma, chronic obstructive pulmonary disease (COPD) and bronchitis. Compound I of the invention can be administered as a monotherapy. Additionally, compound I of the present invention can be co-administered or used in combination with one or more disease-modifying antirheumatic drugs (DMARDS) such as methotrexate, azathioptrine leflunomide, penicillamine, gold salts, mycophenolate mofetil, cyclophosphamide and other similar drugs. They can also be co-administered with or used in combination with one or more non-steroidal anti-inflammatory drugs (NSAIDS) such as piroxicam, naproxen, indomethacin, ibuprofen and the like; COX-2 selective inhibitors such as rofecoxib, which is in Vioxx® (from Merck & Company, Whitehouse Station, N.J.) and celecoxib, which is in Celebrex® (from Pfizer Inc., New York, N.Y.); COX-1 inhibitors such as Piroxicam, which is in Feldene® (from Pfizer Inc., New York, N.Y.); immunosuppressives such as steroids, cyclosporine, Tacrolimus, rapamycin and the like; biological response modifiers (BRMs) such as etanercept, which is in Enbrel® (from Wyeth-Ayerst, Philadelphia, Pa.), infliximab, which is in Remicade® (from Centocor, Inc., Malvern, Pa.), IL-1 antagonists, anti-CD40, anti-CD28, IL-10, anti-adhesion molecules and the like; and other anti-inflammatory agents such as p38 kinase inhibitors, PDE4 inhibitors, TACE inhibitors, chemokine receptor antagonists, Thalidomide, which is in Thalomid® (Celgene Corporation, Warren, N.J.) and other small molecule inhibitors of pro-inflammatory cytokine production. Other drugs that the compounds of the invention can be co-administered or used in combination with include Anaprox, Arava, Arthrotec, Azulfidine, Aspirin, Cataflam, Celestone Soluspan, Clinoril, Cortone Acetate, Cuprimine, Daypro, Decadron, Depen, Depo-Medrol, Disalcid, Dolobid, Naprosyn, Gengraf, Hydrocortone, Imuran, Indocin, Lodine, Motrin, Myochrysine, Nalfon, Naprelan, Neoral, Orudis, Oruvail, Pediapred, Plaquenil, Prelone, Relafen, Solu-Medrol, Tolectin, Trilisate and Volataren. These include any formulation of the above named drugs.

For the treatment of multiple sclerosis, the compounds of the invention can be co-administered or used in combination with one or more additional agents, which may be the same or different, and are independently selected from the group consisting of Avonex® (Interferon B-1a from Biogen), Betaseron® (Interferon B-1b from Berlex) and Copaxone® (glatiramer acetate from Teva Neuroscience incorporated).

For combination treatment with more than one active agent, where the active agents are in separate dosage formulations, the active agents can be administered separately or in conjunction. In addition, the administration of one element can be prior to, concurrent to, or subsequent to the administration of the other agent, or other agents. Ideally, the active agents should be given at the same time.

Another aspect of the invention relates to a kit for treating cancer, inflammatory diseases, immunomodulatory diseases, and respiratory diseases comprising in one or more containers an active compound for stimulating cannabinoid $CB_2$ receptors in a patient which comprises in one or more containers, one or more compounds according to claim 1 in one or more pharmaceutically acceptable carriers. Preferably, the amount of compound I in the kit is a therapeutically effective amount. The daily dose of a compound of formula I for treatment of a disease or condition can range from about 0.001 mg/kg to about 100 mg/kg of body weight per day, preferably from about 0.001 mg/kg to about 50 mg/kg of body weight per day, more preferably from about 0.001 mg/kg to about 10 mg/kg of body weight per day.

Compounds of the present invention are generally prepared by processes known in the art, for example by the processes described below.

The following abbreviations are used in the procedures and schemes:

aqueous (aq), anhydrous (anhyd), n-Butyllithium (n-BuLi), dibromodimethylhydantoin (DBDMH), diisopropylethylamine (DIPEA), diethyl ether ($Et_2O$), dimethylacetamide (DMA), dimethyl sulfoxide (DMSO), ethanol (EtOH), ethyl acetate (EtOAC), leaving group (LG), meta-chloroperoxybenzoic acid (MCPBA), methanesulfonic acid (MsOH), methanesulfonyl chloride (MsCl), preparative thin layer chromatography on Merck-silica plates (PTLC), phenyl (Ph), pyridium chlorochromate (PCC), pyridine (Py), trifluoroacetic anhydide (TFAA), triflic anhydride ($Tf_2O$), tetrahydrofuran (THF), silica gel chromatography (sgc), thin layer chromatography (TLC), room temperature (rt), hour (h), minutes (min), mole (M), pounds per square inch (psi), and saturated aqueous sodium chloride solution (brine).

group. Examples of N-protecting groups suitable in the practice of the invention include allyl, methoxymethyl, benzyloxymethyl, $CG_3CO$ (where G is a halogen), benzyloxycarbonyl, trityl, pivaloyloxymethyl, tetrahydranyl, benzyl, di(p-methoxyphenyl)methyl, triphenylmethyl, (p-methoxyphenyl)diphenylmethyl, diphenylphosphinyl, benzenesulfenyl, methylcarbamate, 2-trimethylsilylethyl carbamate, 1-methyl-1-phenylethyl carbamate, t-butyl carbamate ("t-Boc"), cyclobutyl carbamate, 1-methylcyclobutyl carbamate, adamantyl carbamate, vinyl carbamate, allyl carbamate, cinnamyl carbamate, 8-quinolyl carbamate, 4,5-diphenyl-3-oxazolin-2-one, benzyl carbamate, 9-anthrylmethyl carbamate, diphenylmethyl carbamate, S-benzylcarbamate, and the moiety:

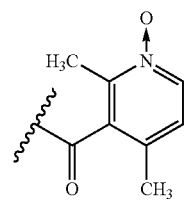

General Scheme I
Preparation if Indole Sulfonyl Linked Compounds

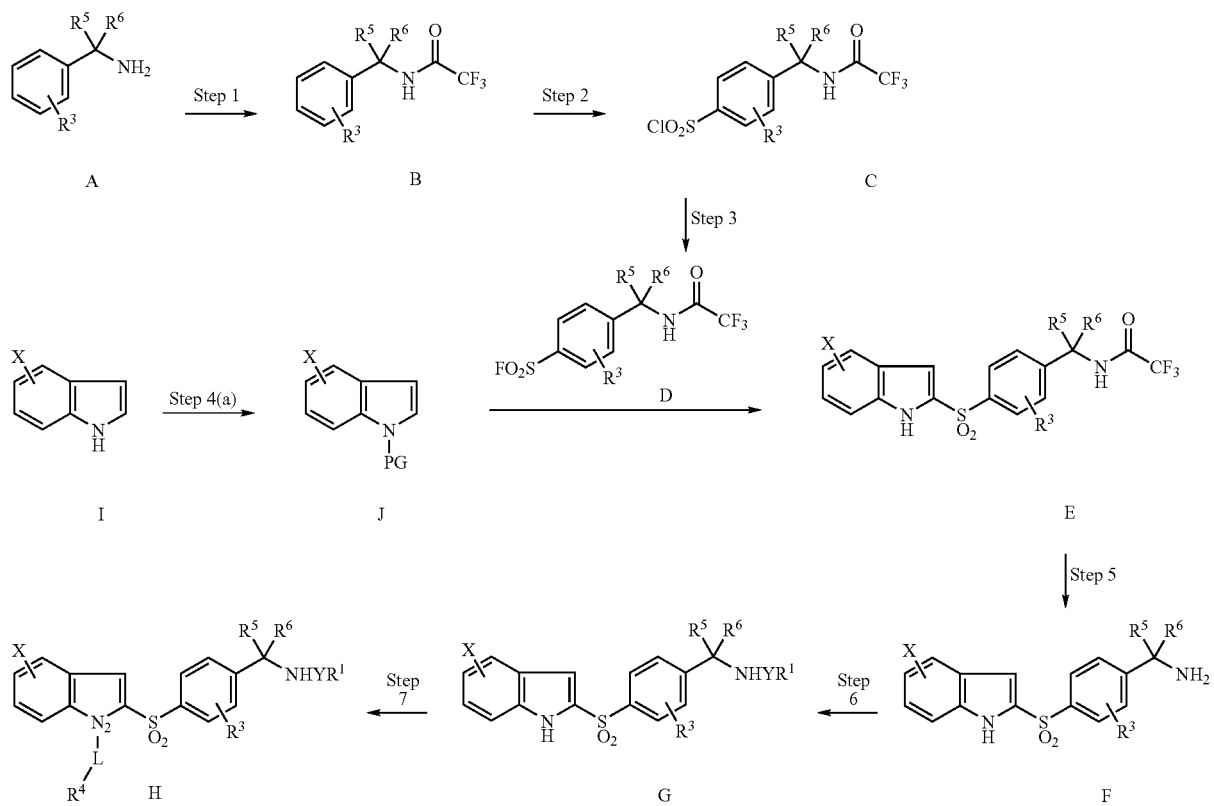

The substituents $L^1$, $L^2$, M, X, Y, Z, $R^1$, $R^2$, $R^3$, $R^4$, $R^5$, and $R^6$, and the symbols n and p in the general schemes below are defined above. PG represents an N-protecting In step 1, trifluoroacetic anhydride is dissolved in a suitable inert solvent such as methylene chloride, chloroform, acetonitrile, dichloroethane and the like, and reacted with compound A, preferably at room temperature for 1–5 h, to form compound B.

In step 2, compound B is dissolved in ClSO$_3$H between 0° C. and room temperature, stirred at room temperature for about 72 h, and then poured into ice H$_2$O. A precipitate is formed containing compound C, which can be collected by filtration methods known in the art.

Alternative step 2:

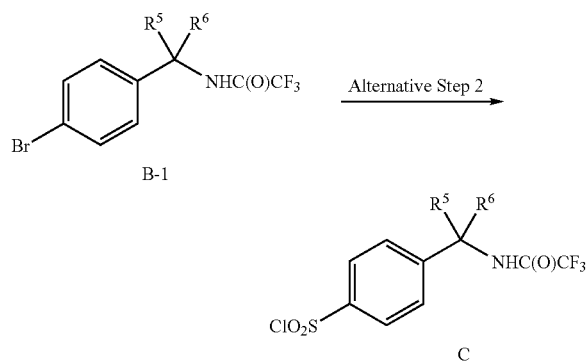

In alternative Step 2, compound B-1 is dissolved in anhydrous THF and cooled to about −78° C. and treated with nBuLi. The resulting lithiated species is quenched by bubbling SO$_2$ gas. The resulting mixture was warmed to room temperature and the precipitated lithium sulfonate salt was collected by filtration. The salt was redissolved in a 1:1 mixture of water to methylene chloride and treated with chlorinating agent such as NCS. After workup, compound C was obtained.

In step 3, compound C is dissolved in a suitable solvent such as acetone and H$_2$O. KF is added and it is stirred at room temperature. After work up, the product (compound D) can be purified via methods known in the art such as sgc or crystallization.

In step 4(a), a protected indole (compound J), for example, N-Boc indole, used in step 4 is prepared by dissolving protecting group (PG) as defined above in a suitable inert solvent such as methylene chloride, dichloroethane, THF and DMF, and reacting with an indole derivative (compound I) in the presence of dimethylaminopyridine, trimethylamine, and (iPr)$_2$NEt. The product (compound J) can be purified via sgc or crystallization.

In step 4, the protected indole (compound J) is dissolved in a suitable solvent such as EtOAc or ether, cooled in a dry ice/IPA bath and treated with n-BuLi. The resulting anion is trapped with compound D. The product, compound E, can be purified via chromatography or crystallization.

In step 5, compound E is dissolved in a suitable solvent such as dioxane, ethanol, methanol or THF and an alkali metal hydroxide or carbonate such as lithium hydroxide or potassium carbonate is added either as an aqueous solution or as a solid. The reaction mixture is stirred at room temperature for 0.5–24 h. The product, compound F, can be purified via sgc or crystallization.

In step 6, a combination of compound F and a tertiary amine base is dissolved in a suitable solvent such as methylene chloride or dioxane, at room temperature, cooled, and a suitable electrophile represented by $R^1$—Y-LG is added, wherein LG is preferably Cl or F. The reaction mixture is stirred between −78° C. and room temperature for about 0.5 to about 48 h. The product (compound G) can be purified via sgc or crystallization.

In step 7, compound G is dissolved in a suitable inert solvent such as THF, methylene chloride, dichloroethane, or ether. Aqueous NaOH is used as a base. An electrophile represented by $R^4$-$L^2$-LG, wherein LG is preferably Cl, is added and the reaction mixture is stirred in the presence of a phase-transfer catalyst (such as tetrabutyl ammonium hydrogen sulfate, methyl-n-butylammonium chloride, or benzyltriethylammonium hydroxide) between 0° C. and 100° C. for about 0.5 to about 48 h. The product (compound H) can be purified via sgc or crystallization.

General Scheme II

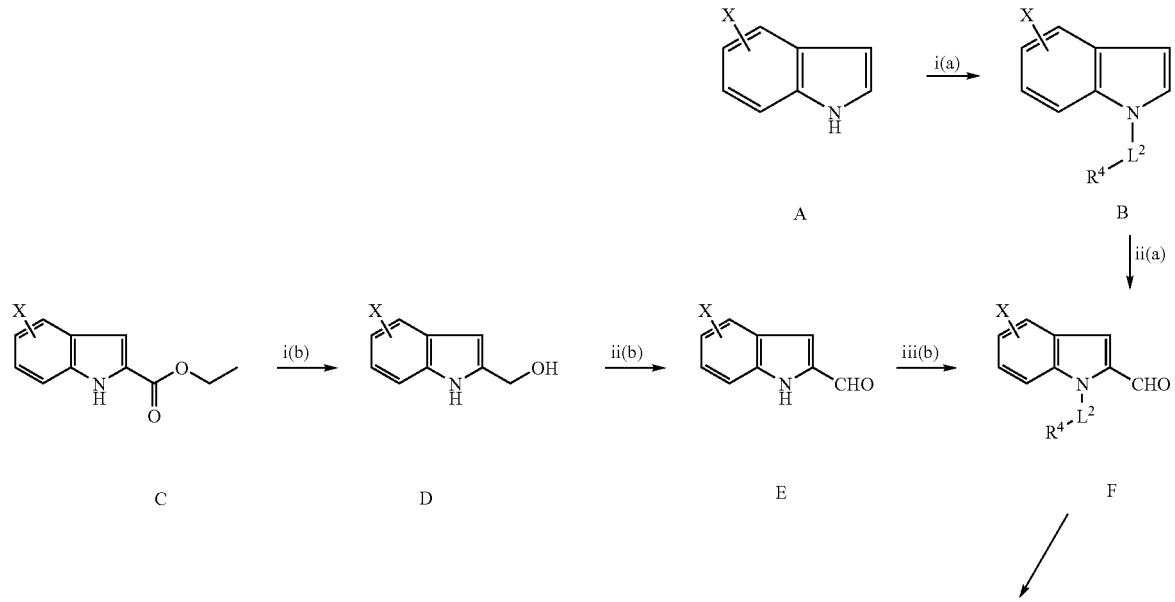

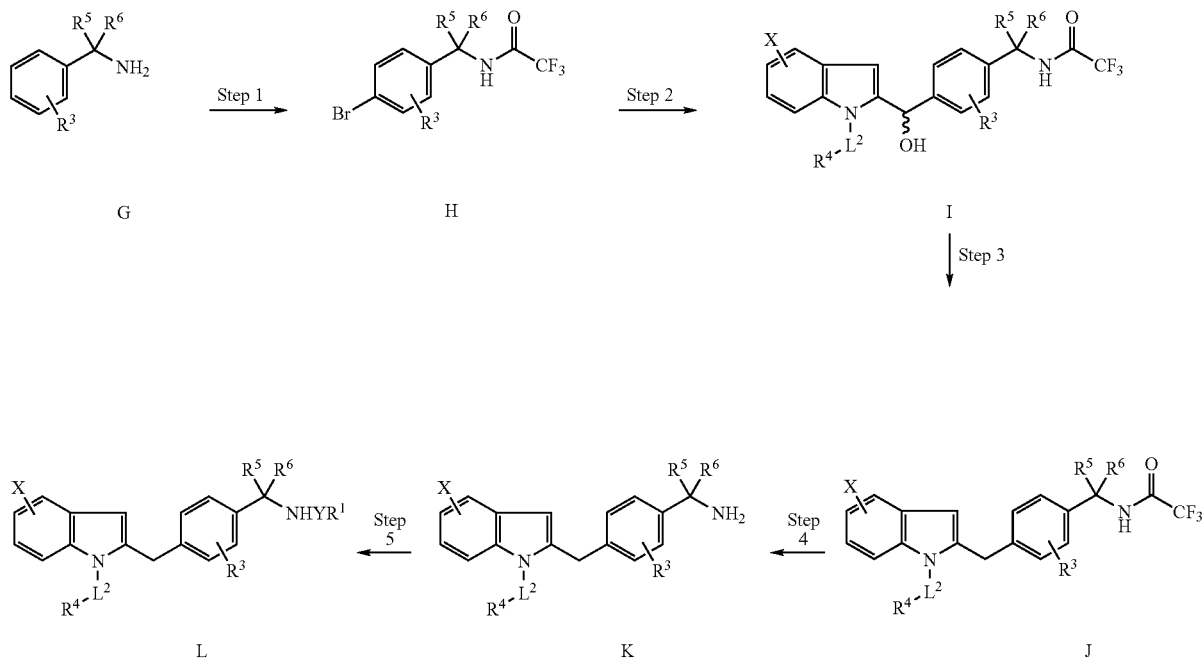

Description of Reactions-General Scheme II

In step 1, trifluoroacetic anhydride is dissolved in a suitable inert solvent, such as methylene chloride or dichloroethane, and reacted with a benzyl amine (compound G) at room temperature for 1–5 h. MsOH (2 eq) is added followed by DBDMH and the reaction mixture is stirred, preferably overnight at room temperature, and subjected to aqueous work up. The benzyl amide product (compound H) is recrystallized, preferably from a mixture of $Et_2O$ and hexanes.

In step 2, compound H is dissolved in a suitable solvent such as THF or ether, cooled in a dry ice/acetone bath (−78° C.) and treated with n-BuLi. The dianion is then treated with a THF solution containing compound F. The resulting mixture is warmed to about rt and stirred for about 10 h. The product (compound I) can be purified by chromatography.

In step 3, compound I is dissolved in a suitable inert solvent such as THF, methylene chloride or dichloroethane, and reacted with $Et_3SiH$ and TFA between 0° C. and 100° C. for about 0.5 to about 48 h. After work up, the product (compound J) can be purified via chromatography.

In step 4, compound J is dissolved in a suitable solvent such as dioxane, ethanol, methanol or THF, and an alkali metal hydroxide or carbonate such as lithium hydroxide or potassium carbonate is added either as an aqueous solution or as a solid. The reaction mixture is stirred at room temperature for 0.5–24 h. The product (compound K) can be purified via sgc or crystallization.

In step 5, a combination of compound K and a tertiary amine base is dissolved in a suitable solvent such as methylene chloride, THF, dichloroethane or dioxane, preferably at room temperature. The reaction mixture is cooled, and a suitable electrophile, represented by the formula $R^1$—Y-LG wherein LG is preferably CL or F, is added. The reaction mixture is stirred preferably at a temperature between −78° C. and room temperature for about 0.5 to about 48 h. The product (compound L) can be purified via sgc or crystallization.

The aldehyde (compound F) used in step 2 is prepared by one of the following two procedures:

1) Treating an indole derivative (compound A) with a suitable base, such as NaOH, KOH, NaH, $(iPr)_2NEt$, or nBuLi, in the presence of an electrophile represented by the formula $R^4$-$L^2$-LG, wherein LG is preferably Cl, followed by regioselective ortho lithiation of the product (compound B) and trapping with DMF to form compound F.

2) Indole carboxylate (compound C) is dissolved in a suitable inert solvent such as THF or ether, and reduced with LAH preferably between 0° C. and 100° C. for about 0.5 to about 48 h. The corresponding alcohol (compound D) is dissolved in a suitable inert solvent such as methylene chloride or dichloroethane, and is oxidized with $MnO_2$ between 0° C. and 100° C. for about 0.5 to about 48 h. The product (compound E) is dissolved in a suitable inert solvent such as THF, dichloroethane, DMF or methylene chloride, and an aqueous base such as NaOH, KOH, or $(iPr)_2NEt$. An electrophile represented by the formula $R^4$-$L^2$-LG, wherein LG preferably is Cl, is added and the reaction mixture is stirred in the presence of a phase-transfer catalyst (such as tetrabutyl ammonium hydrogen sulfate, methyl-n-butylammonium chloride, or benzyltriethylammonium hydroxide) between 0° C. and 100° C. for about 0.5 to about 48 h. The product (compound F) can be purified via sgc or crystallization.

General Scheme III
Preparation of Indole Carbonyl Linked Compounds

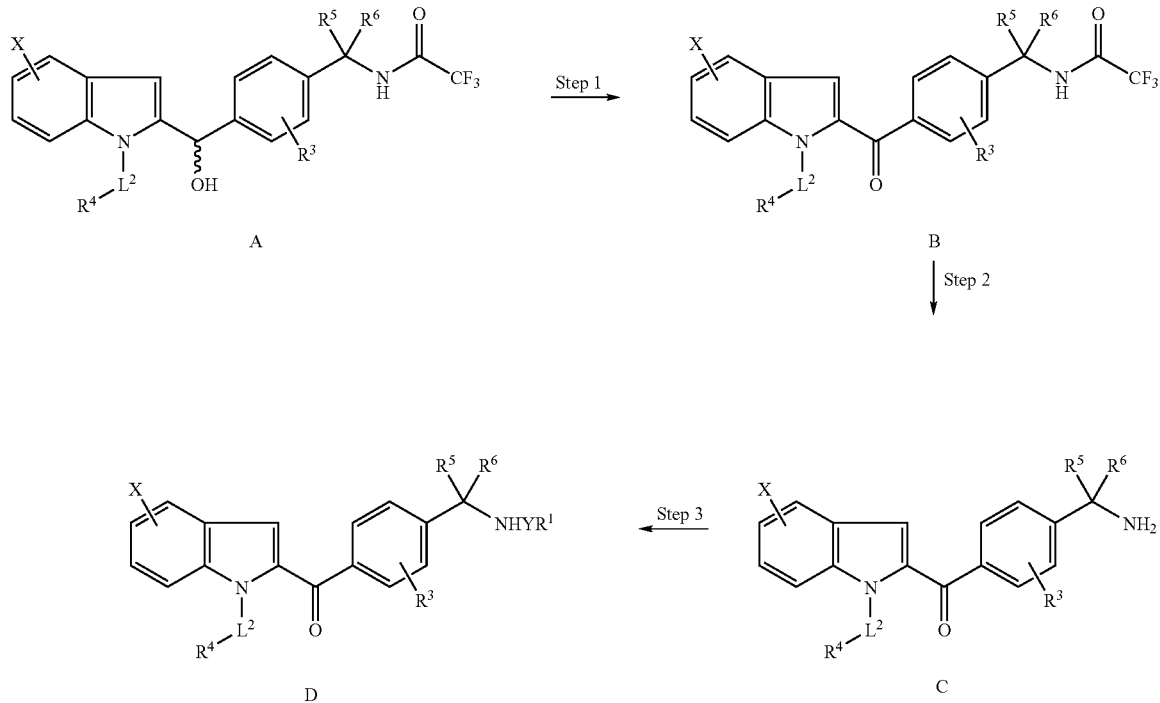

Description of Reactions-General Scheme III:

In step 1, compound A (the product of step 2 of Scheme II) is oxidized with PCC, in a suitable inert solvent such as methylene chloride, dichloroethane, or THF, to the carbonyl compound (B) by stirring preferably at rt for about 18 h.

In step 2, compound B is dissolved in a suitable solvent such as dioxane, ethanol, methanol or THF and an alkali metal hydroxide or carbonate such as lithium hydroxide or potassium carbonate is added either as an aqueous solution or as a solid. The reaction mixture is stirred at room temperature for 0.5–24 h. The product (compound C) can be purified via sgc or crystallization.

In step 3, a combination of compound C and a tertiary amine base is dissolved in a suitable solvent such as methylene chloride or dioxane, at room temperature, cooled, and a suitable electrophile represented by the formula $R^1$—Y-LG, wherein LG is preferably Cl, is added. The reaction mixture is stirred preferably between −78° C. and room temperature for about 0.5 to about 48 h. The product (compound D) can be purified via sgc or crystallization.

General Scheme IV
Preparation of Furanyl Compounds

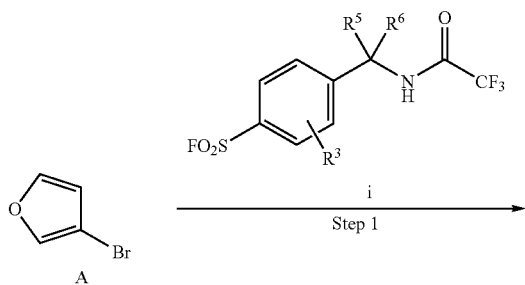

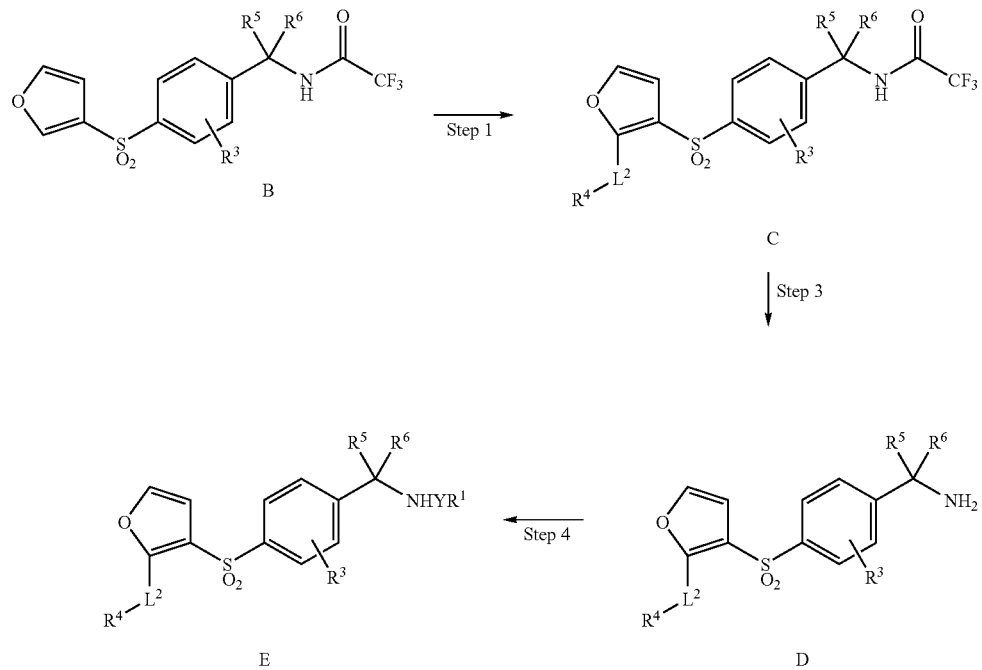

Description of Reactions-General Scheme IV:

In step 1, the Bromo-furan (Compound A) (obtained from Aldrich Chemical Company, Inc. Milwaukee, Wis.) is dissolved in THF or ether, cooled in a dry ice/IPA bath and treated with t-BuLi. The resulting anion is trapped with the sulfonyl fluoride compound (Compound i) which is prepared in step 3 of Scheme I. The product (compound B) can be purified via chromatography or crystallization.

In step 2, compound B is dissolved in THF or ether, and treated with a base such as t-BuLi at −78° C. to form a dianion, which is trapped with a suitable electrophile represented by $R^4$-$L^2$-LG, wherein LG is preferably Cl or F. The reaction mixture is quenched with a suitable proton source such as aq $NH_4Cl$ or phosphate buffer, then extracted with a suitable solvent such as EtOAc, ether or methylacetone. The product (compound C) can be purified via sgc or crystallization.

In step 3, compound C is dissolved in a suitable solvent, such as dioxane, ethanol, methanol or THF. An alkali metal hydroxide or carbonate, such as lithium hydroxide, potassium carbonate, NaOH, KOH or sodium carbonate, is added either as an aqueous solution or as a solid. The reaction mixture is stirred preferably at room temperature for 0.5–24 h. The product (compound D) can be purified via sgc or crystallization.

In step 4, a combination of compound D and a tertiary amine base is dissolved in a suitable solvent, such as methylene chloride, THF, dichloroethane or dioxane, at room temperature, cooled, and a suitable electrophile represented by the formula $R^1$—Y-LG is added, wherein LG is preferably Cl.

The reaction mixture is stirred preferably between −78° C. and room temperature for about 0.5 to about 48 h. The product (Compound E) can be purified via sgc or crystallization.

General Scheme V
Preparation of Pyridyl Carbonyl and Methylene Linked Compounds

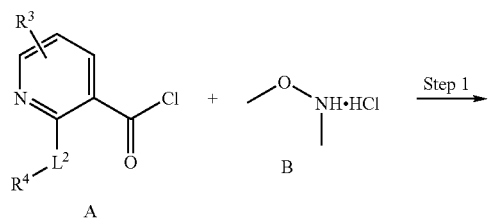

-continued

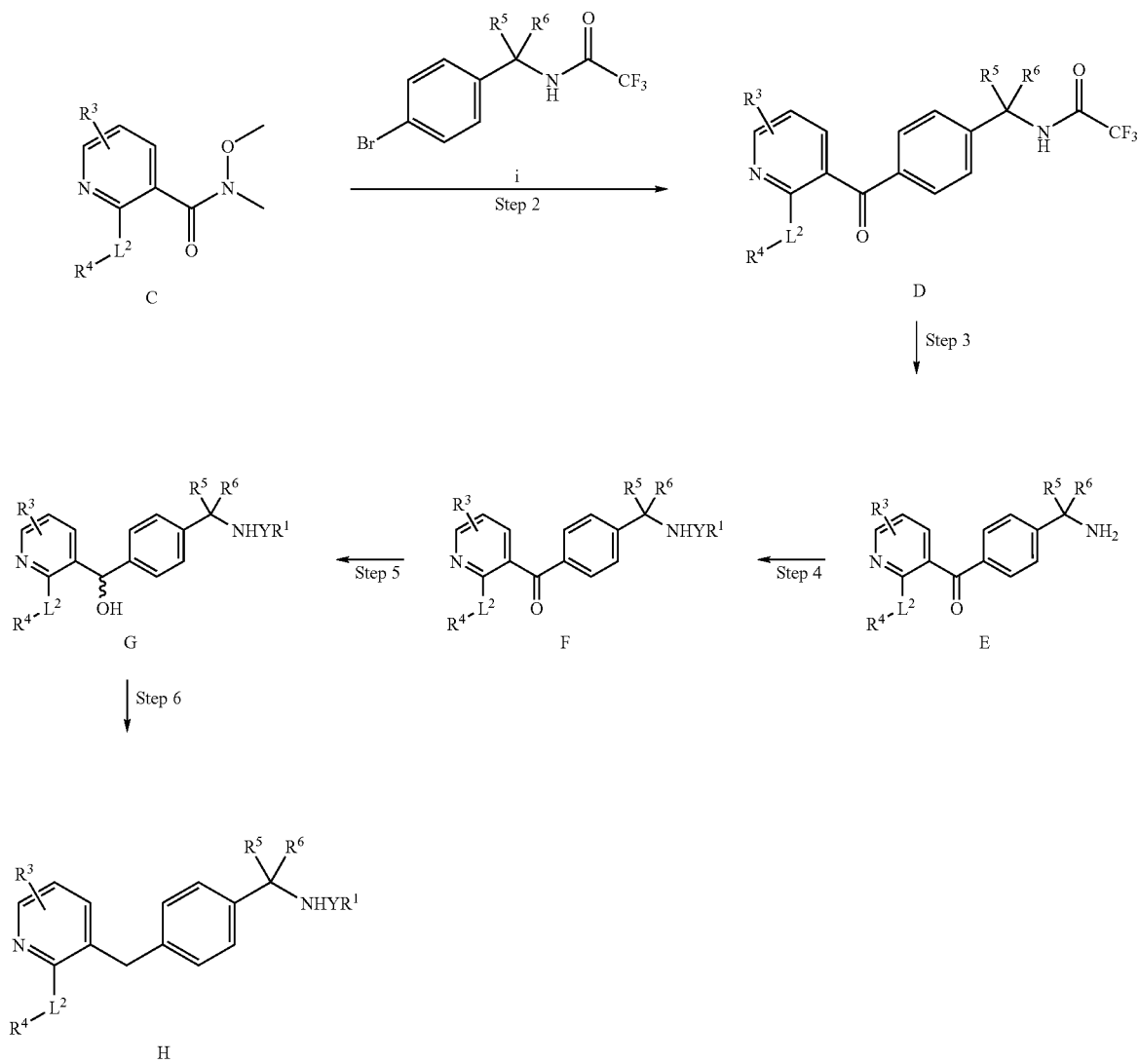

In step 1, the acyl chloride (compound A) and N-methoxyl-N-methylamine HCl (compound B) which is commercially available are dissolved in a suitable solvent, such as THF, dioxane or CH$_2$Cl$_2$, and treated with a base such as triethylamine, (iPr)$_2$NEt and/or DMAP, preferably at room temperature for 0.5–24 h. The product (compound C) can be purified via sgc or crystallization.

In step 2, compound i, which is prepared in step 1 of Scheme II, is dissolved in THF, cooled in a dry ice/IPA bath and treated with n-BuLi. The resulting anion is trapped with compound C. The product (compound D) can be purified via chromatography or crystallization.

In step 3, the compound D is dissolved in a suitable solvent such as dioxane, ethanol, methanol or THF and an alkali metal hydroxide or carbonate such as lithium hydroxide or potassium carbonate is added either as an aqueous solution or as a solid. The reaction mixture is stirred at room temperature for 0.5–24 h. The product (compound E) can be purified via sgc or crystallization.

In step 4, a combination of compound E and a tertiary amine base is dissolved in a suitable solvent such as methylene chloride or dioxane, at room temperature, cooled, and a suitable electrophile represented by R$^1$—Y-LG, wherein LG is preferably Cl. The reaction mixture is stirred between −78° C. and room temperature for about 0.5 to to about 48 h. The product (compound F) can be purified via sgc or crystallization.

In step 5, compound F is dissolved in a suitable solvent such as methanol. NaBH$_4$ is added at 0° C. The reaction mixture is then stirred between −78° C. and room temperature for about 0.5 to about 48 h. The product (compound G) can be purified via sgc or crystallization.

In step 6, compound G is dissolved in a suitable solvent such as methylene chloride, and treated with Et$_3$SiH and TFA at room temperature for 0.5 to 120 h. The product (compound H) can be purified via sgc or crystallization.

General Scheme VI
Preparation of Dihydrofuran Compounds

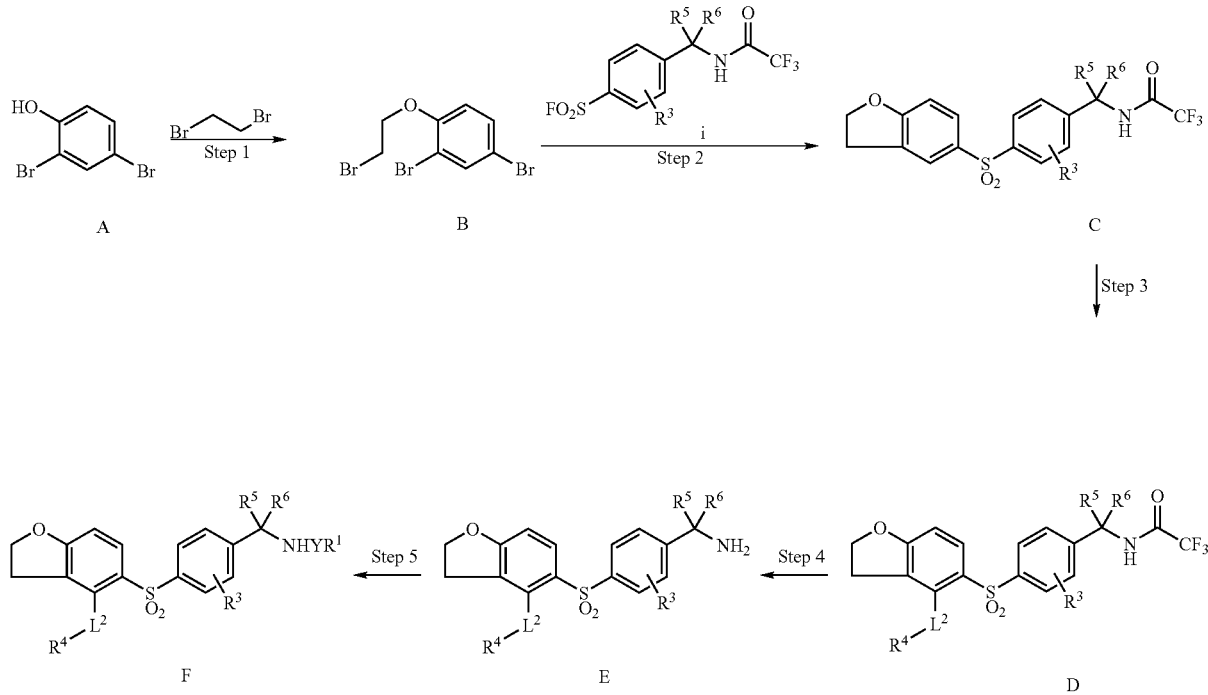

Description of Reactions-General Scheme VI:

In step 1,2,4-dibromophenol (Compound A) (obtained from Aldrich Chemical Company, Inc. Milwaukee, Wis.) and dibromoethane are dissolved in a suitable solvent, such as methylene chloride, benzene, dichloroethane or toluene, and an aqueous base such as NaOH, KOH or LiOH. The reaction mixture is stirred in the presence of a phase-transfer catalyst (such as tetrabutyl ammonium hydrogen sulfate, methyl-n-butylammonium chloride, or benzyltriethylammonium hydroxide) between 0° C. and 100° C. for about 0.5 to about 48 h. The product (compound B) can be purified via sgc or crystallization.

In step 2, compound B is dissolved in THF or ether, preferably between −78° C. to −100° C. After stirring, the reaction mixture is treated with another portion of base at preferably between −78° C. to −100° C. The resulting anion is trapped with compound (i) prepared in step 3 of Scheme I. The product (compound C) can be purified via chromatography or crystallization.

In step 3, the product of step 2 (compound C) is dissolved in THF or ether, and treated with a base such as n-BuLi, preferably between −78° C. and −100° C. to form a dianion, which is trapped with a suitable electrophile represented by $R^4$-$L^2$-LG. The reaction mixture is quenched with a suitable proton source such as aq $NH_4Cl$ or phosphate buffer, then extracted with EtOAc or ether. The product (compound D) can be purified via sgc or crystallization.

In step 4, the product of step 3 (compound D) is dissolved in a suitable solvent such as dioxane, ethanol, methanol or THF and an alkali metal hydroxide or carbonate such as lithium hydroxide or potassium carbonate is added either as an aqueous solution or as a solid. The reaction mixture is stirred preferably at room temperature for 0.5–24 h. The product (compound E) can be purified via sgc or crystallization.

In step 5, a combination of the product of step 4 (compound E) and a tertiary amine base, such as triethylamine or $(iPr)_2NEt$, is dissolved in a suitable solvent such as methylene chloride, dichloroethane or dioxane, at room temperature, cooled, and a suitable electrophile represented by $R^1$—Y-LG is added wherein LG preferably represents Cl. The reaction mixture is stirred preferably between −78° C. and room temperature for about 0.5 to about 48 h. The product (Compound F) can be purified via sgc or crystallization.

Those skilled in the art will appreciate that similar reactions to those described in the above schemes can be carried out on other compounds of formula I as long as substituents present would not be susceptible to the reaction conditions described. Starting materials for the above processes are either commercially available, known in the art, or prepared by procedures well known in the art.

The invention disclosed herein is exemplified by the following preparation and examples which should not be construed to limit the scope of the disclosure. Alternative mechanistic pathways and analogous structures can be apparent to those skilled in the art.

EXAMPLES

Example I

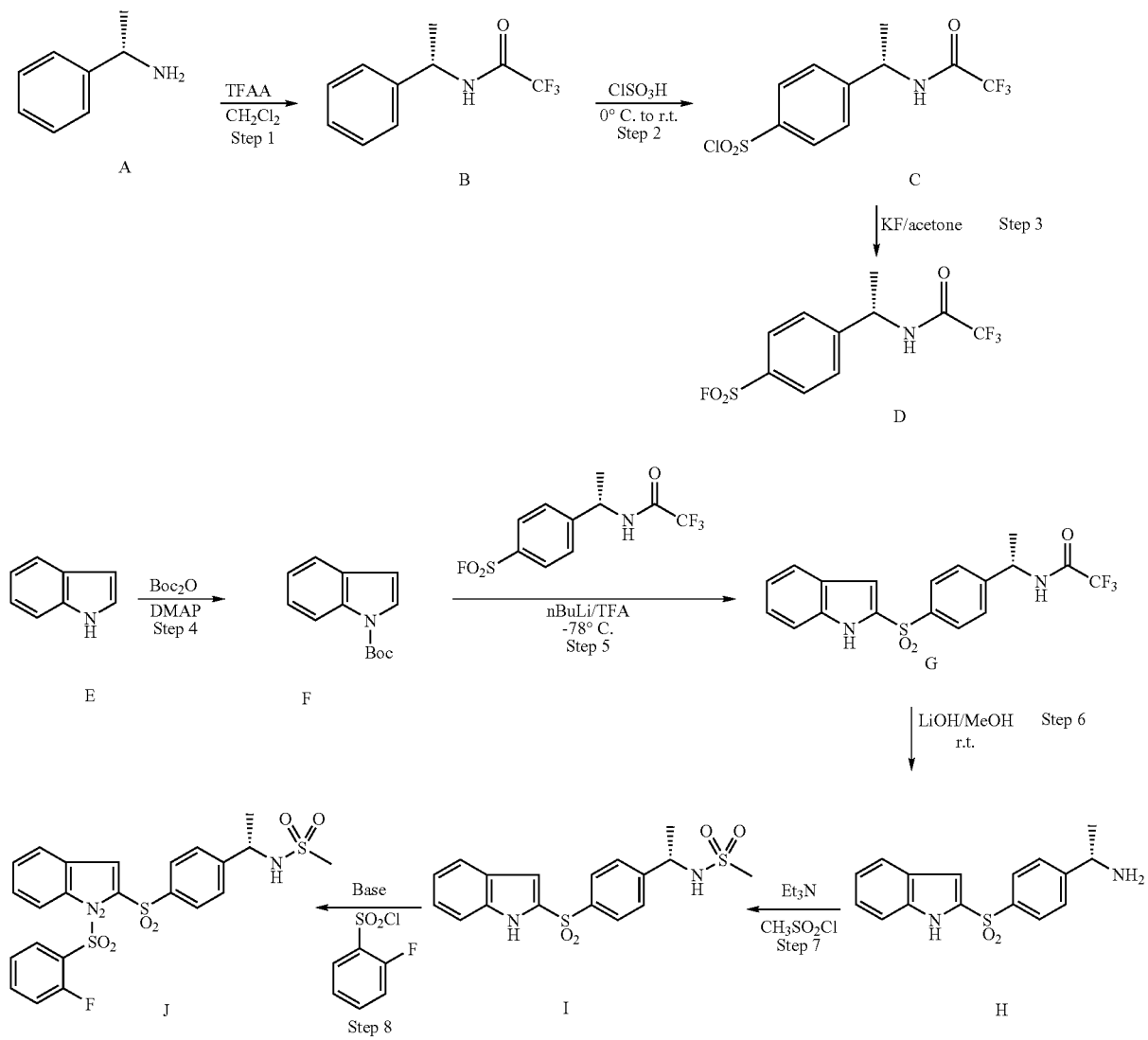

Step 1. Trifluoracetic anhydride (33.5 ml, 0.24 mol) was dissolved in CH$_2$Cl$_2$ (200 ml) and cooled in an ice-bath. A solution of (S)-α-methyl benzylamine (28.28 ml, 0.232 mol) (obtained from Aldrich Chemical Company, Inc. Milwaukee, Wis.) dissolved in CH$_2$Cl$_2$ (50 ml) was added and stirred for 10 h. The reaction was washed 4×100 ml water, 2×100 ml aq. NaHCO$_3$, and 1×100 ml brine. The organics were dried and concentrated. The crude product (compound B) was taken to step 2 without additional purification.

Step 2: Compound B from step 1 was dissolved in 100 ml of chlorosulfonic acid at 0° C. and stirred for 72 h allowing the temperature to rise to about room temperature. The reaction mixture was poured into a 500 ml ice-H$_2$O mixture and stirred vigorously for 2 h. The product (compound C) was collected by filtration, recrystallized from ether, and dried under reduced pressure to yield 52 g of pure C.

Alternative Step 2:

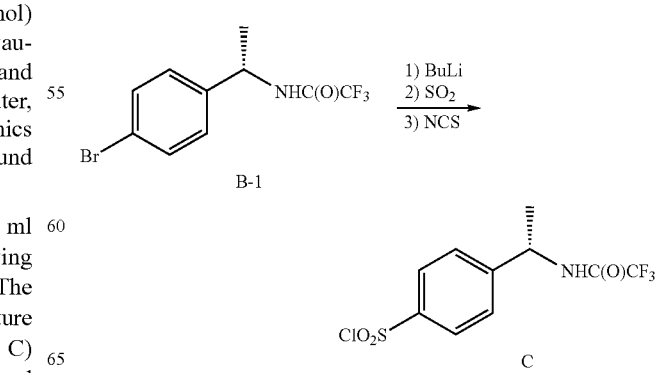

In a flame dried flask under N$_2$ blanket, compound B-1 (10 g, 33.8 mmol) (Compound E from example 4) was dissolved in dry THF (100 mL) and cooled to –78° C. A solution of n-butyl lithium (2.0 M in hexanes, 34 mL, 68.0 mmol) was added and the reaction mixture was stirred for 20 minutes. A solution of SO$_2$ in Et$_2$O (300 mL) was added and the reaction was stirred for one hour. The reaction mixture was slowly warmed up to room temperature and stirred overnight. Solid was collected by suction filtration and then washed with Et$_2$O. This solid was dissolved in a mixture of H$_2$O (50 ml) and CH$_2$Cl$_2$ (60 mL). NCS (4.5 g, 33.7 mmol) and acetic acid (1.8 g) were added and the reaction was stirred at rt for 2 h. The layers were separated and the organic layer washed with NaHCO$_3$ (100 mL) and brine (100 mL×2), respectively. The organic layer was dried over Na$_2$SO$_4$ and then concentrated to dryness to give the corresponding sulfonyl chloride compound C 4.35 g (41%).

Step 3: To a round-bottom flask was added compound C (4.0 g, 13 mmol) and KF (2.2 g, 38 mmol) followed by addition of acetone (40 mL) and water (40 mL). The reaction mixture was stirred at room temperature overnight. The solvent was then removed. Methylene chloride (40 mL) was added and it was washed with aqueous NaCl solution (40 mL). The organic layer was dried over Na$_2$SO$_4$ and then concentrated to dryness to give 3.75 g (99%) of compound D.

Step 4: Indole (10 g, 85 mmol) (compound E) and Boc$_2$O (18.79 g, 85 mmol) were dissolved in methylene chloride (200 mL). DMAP (cat.) was added and the reaction was stirred at room temperature overnight. The reaction mixture was washed with aqueous NaCl solution (100 mL). The organic layer was dried over Na$_2$SO$_4$, and concentrated to dryness. The crude product was purified via sgc (25% EtOAc/hexanes) to give 18.6 g (100%) of compound F.

Step 5: In a flame dried flask under N$_2$ blanket, compound F (2.0 g, 9.2 mmol) was dissolved in dry THF (20 mL) and cooled to –78° C. A solution of n-butyl lithium (1.7 M in hexanes, 5.9 mL, 10.0 mmol) was added and the reaction mixture was stirred for 45 min. Compound D (0.5 g, 1.7 mmol) in THF (1.5 mL) was added and the reaction mixture was stirred at –78° C. for 1 h. Another portion of compound F (0.5 g, 1.7 mmol) in THF (1.5 mL) was added, and the reaction mixture was stirred at –78° C. for several hours before slowly warming the reaction mixture up to room temperature. The reaction mixture was stirred at room temperature for 1 day. The reaction mixture was then quenched with saturated aqueous NH$_4$Cl (20 mL). Ethyl acetate (30 mL) was added and the layers were separated. The organic layer was washed with brine, then dried over Na$_2$SO$_4$, and concentrated to dryness. The crude product was purified via sgc (25% EtOAc/hexanes) to give 570 mg (43%) of Compound G.

Step 6: (90 mg, 0.23 mmol) of compound G was dissolved in methanol (1.5 mL) at room temperature. LiOH (1.0 M, 0.90 mL, 0.90 mmol) was added and the mixture was stirred at room temperature overnight. The solvent was removed and CH$_2$Cl$_2$ (15 mL) and brine (15 mL) were added and the layers were separated. The aqueous layer was extracted with additional CH$_2$Cl$_2$ (15 mL) and the combined organic layers were dried over Na$_2$SO$_4$ and concentrated to dryness to give compound H. This material was used without further purification.

Step 7: Compound H from Step 6 was dissolved in CH$_2$Cl$_2$ (10 mL) and cooled to 0° C. Methanesulfonyl chloride (26 mg, 0.23 mmol) was added followed by addition of triethylamine (25 mg, 0.25 mmol). The reaction mixture was slowly warmed up to room temperature and stirred overnight. Brine (15 mL) was added and extracted with 2×25 ml of CH$_2$CL$_2$. The organic layer was dried over Na$_2$SO$_4$ and concentrated to dryness. The crude product was purified via PTLC (50% EtOAc/hexanes) to give 65 mg of compound I.

Step 8: Compound I (64 mg, 0.17 mmol) was dissolved in CH$_2$Cl$_2$ (5 mL). NaOH (1.0 M, 1.5 mL) was added followed by addition of 2-fluorophenylsulfonyl chloride (33 mg, 0.17 mmol), and tetrabutylammonium hydrogensulfate (cat.). The reaction mixture was stirred at room temperature overnight. During this time, an additional portion of 2-fluorophenylsulfonyl chloride (33 mg, 0.17 mmol) was added. The aqueous layer was then removed, and the organic layer was dried over Na$_2$SO$_4$ and concentrated to dryness. The crude product was purified via PTLC (50% EtOAc/hexanes) to give 29 mg (32%) of compound J.

Step 2. An alternative to step 2 in Example I involves the following reaction:

Example II

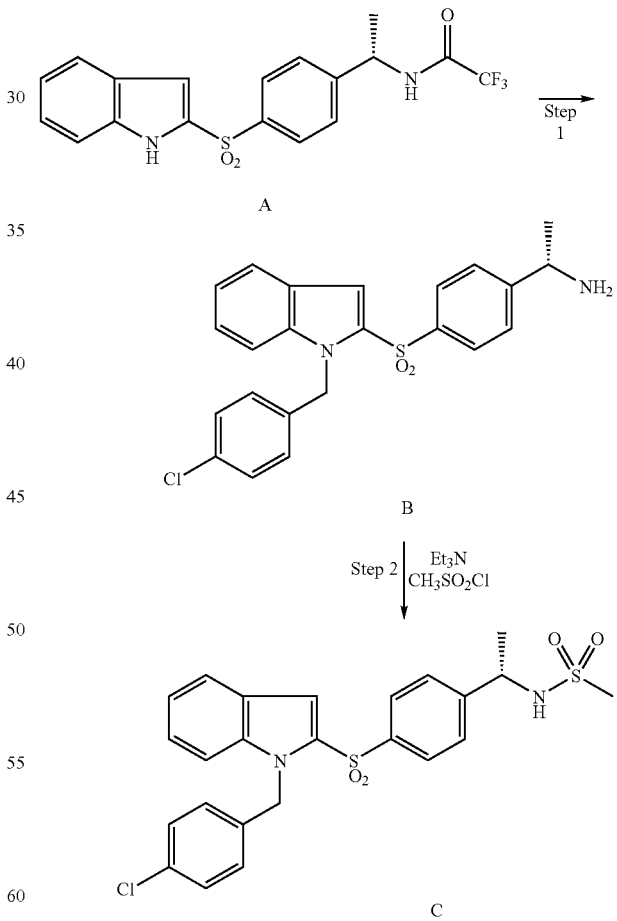

Step 1: Compound A (prepared from step 5 of Example 1) was dissolved in THF (10 mL) and cooled to –78° C. NaH (10 mg, 0.25 mmol) was added and the reaction mixture was warmed to room temperature and stirred for 1 h.

To the reaction mixture was added p-Cl-benzoic bromide (31 mg, 0.15 mmol), and the reaction mixture was stirred at room temperature for 2 days. Methylenechloride (30 ml) was added, and it was washed with aqueous NaCl (30 mL). The organic layer was dried over $Na_2SO_4$ and then concentrated to dryness. The crude product was purified via PTLC (25% EtOAc/hexanes) to give 7.0 mg (33%) of compound B.

Step 2: Compound B (7.0 mg, 17 mmol) was dissolved in $CH_2Cl_2$ (10 mL) and cooled to 0° C. Methanesulfonyl chloride (2.0 mg, 17 mmol) was added followed by addition of triethylamine (2.0 mg, 20 mmol). The reaction mixture was slowly warmed up to room temperature and stirred for overnight. The solvent was removed and the crude product was purified via PTLC (50% EtOAc/hexanes) to give 3.0 mg (36%) of compound C.

Example III

Step 1: Compound A (46 mg, 0.11 mmol) was dissolved in $CH_2Cl_2$ (10 mL) at room temperature. 2-Fluorobenzoyl chloride (22 mg, 0.14 mmol) was added followed by addition of triethylamine (15 mg, 0.15 mmol) and DMAP (cat.). The reaction mixture was stirred at room temperature for 2 h. Another portion of 2-fluorobenzoyl chloride (22 mg, 0.14 mmol) was added to the reaction mixture, which was then stirred for an additional 4 h. The reaction mixture was washed with aqueous NaCl. The organic layer was dried over $Na_2SO_4$ and then concentrated to dryness. The crude product was purified via PTLC (50% EtOAc/hexanes) to give 7.0 mg (12%) of compound B.

Example IV

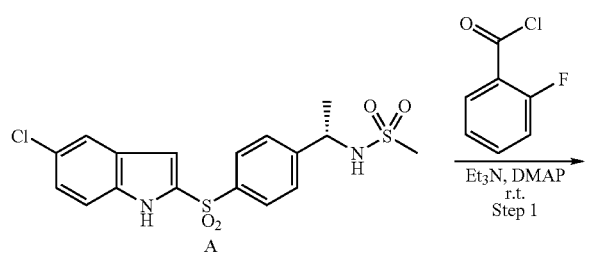

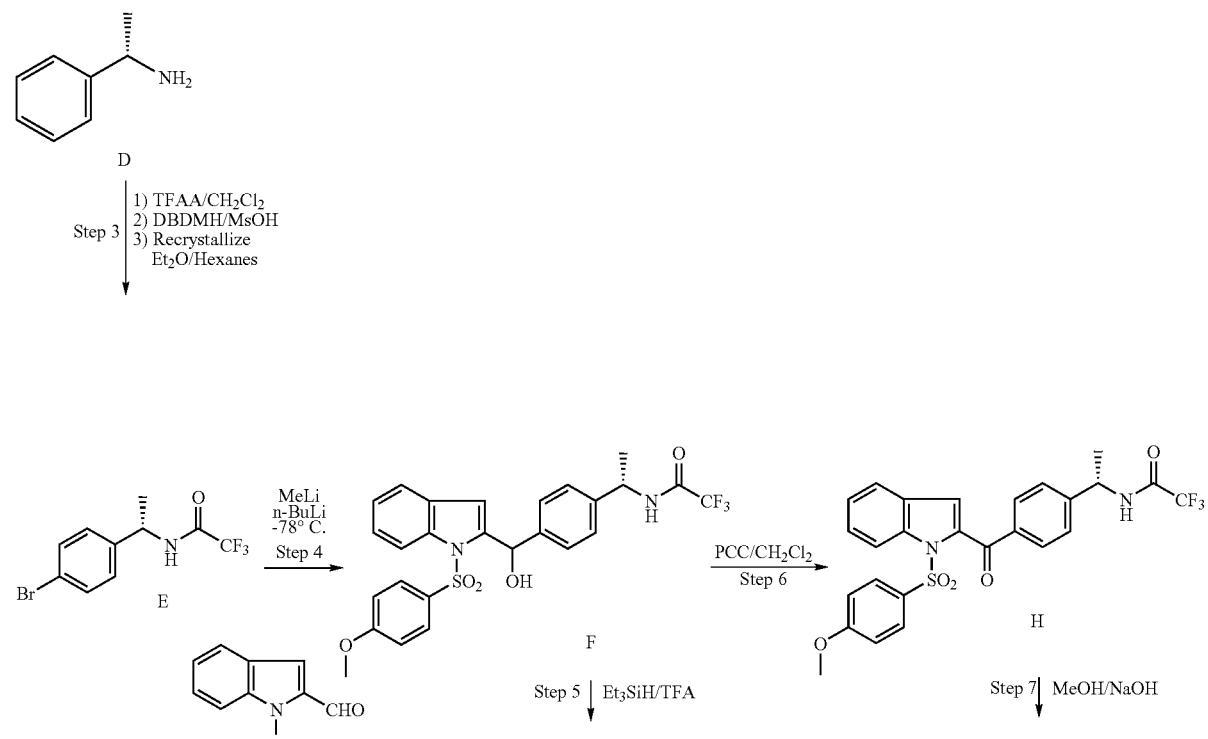

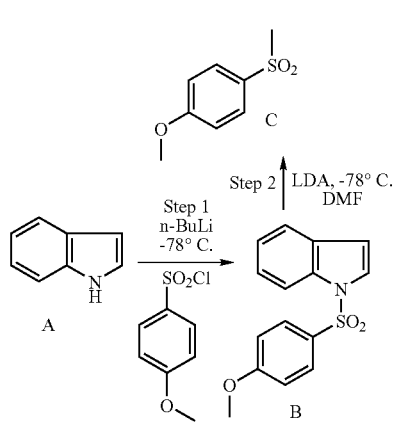
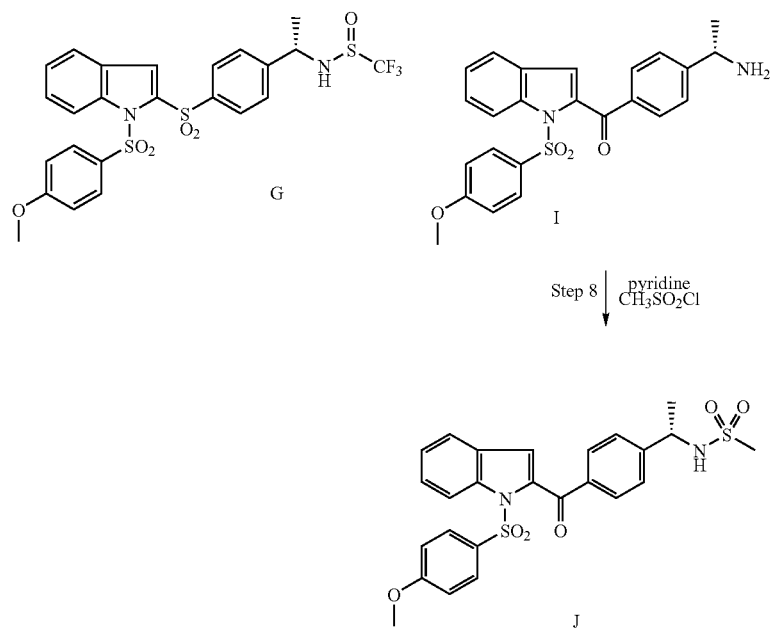

Step 1: In a flame dried flask under $N_2$ blanket, indole (5.0 g, 43 mmol) (obtained from Aldrich Chemical Company, Inc. Milwaukee, Wis.) was dissolved in dry THF (40 mL) and cooled to −78° C. A solution of n-butyl lithium (2.5 M in hexanes, 18 mL, 45 mmol) was added and the reaction mixture was stirred for 1 h while being warmed up to 0° C. The reaction suspension was cooled to −78° C. and a solution of p-methoxyphenyl sulfonyl chloride (9.7 g, 44 mmol) in THF (20 mL) was added dropwise. The reaction mixture was slowly warmed up to room temperature and stirred for 2 days. The mixture was poured into $NaHCO_3$ (2% aq, 120 mL) and extracted with diethyl ether (4×50 mL). The combined organic layers were washed with $NaHCO_3$ (2% aq, 50 mL), $H_2O$ (4×75 mL) and brine (2×50 mL) respectively. It was dried over $Na_2SO_4$, and concentrated to give 12.4 g of crude material. This material was further washed with hexanes to give 11.8 g (96%) of pure compound B.

Step 2: In a flame dried flask under $N_2$ blanket, diisopropylamine (0.4 g, 3.9 mmol) was dissolved in dry THF (8 mL) and cooled to −78° C. A solution of n-butyl lithium (2.5 M in hexanes, 1.46 mL, 3.65 mmol) was added and the reaction mixture was stirred for 0.5 h to form LDA. To this solution was added dropwise a solution of compound B (1.0 g, 3.48 mmol) in THF (10 mL).

The mixture was stirred for 1.5 h at below −70° C. and then allowed to warm slowly to 5° C. over 1.5 h. The reaction mixture was recooled to −78° C., and DMF (0.50 g, 6.8 mmol) was added. The reaction mixture was warmed up to room temperature slowly. The reaction mixture was poured into HCl (10% aq, 150 mL), and extracted with $CH_2Cl_2$ (3×100 mL). The combined organic layer was washed with brine, then dried over $Na_2SO_4$, and concentrated to dryness. The crude product was purified via sgc (10% EtOAc/hexanes) to give 367 mg (33%) of compound C.

Step 3: TFAA (67 mL, 0.474 mol) was dissolved in $CH_2Cl_2$ (300 mL) and cooled in an ice water bath. A solution of (S)-α methyl benzyl amine (56.4 g, 0.465 mol) dissolved in $CH_2Cl_2$ (100 mL) (obtained from Aldrich Chemical Company, Inc. Milwaukee, Wis.) was added and the ice bath was removed. The reaction mixture was stirred at rt for 3 h. The reaction mixture was cooled in an ice bath and MsOH (80 mL, 1.23 mol) was added followed by DBDMH (65 g, 0.227 mol). The reaction mixture was left stirring overnight at rt then quenched with 1M aq $NaHSO_3$. The organic layer was washed with water and brine, dried with $MgSO_4$, and concentrated to give 130 g of crude product, which was recrystallized from diethyl ether and hexanes giving 46 g (32%) of compound E.

Step 4: In a flame dried flask under $N_2$ blanket, compound E (0.28 g, 0.94 mmol) was dissolved in dry THF (20 mL) and cooled to −78° C. A solution of methyl lithium (1.4 M in hexanes, 0.74 mL, 1.04 mmol) was added and the reaction mixture was stirred for 15 min. A solution of n-butyl lithium (2.5 M in hexanes, 0.41 mL, 1.03 mmol) was added and the reaction mixture was stirred for 30 min. Compound C (0.36 g, 1.13 mmol) in THF (3 mL) was added to the reaction mixture at −78° C. and was slowly warmed to −10° C. The reaction mixture was then quenched with saturated aqueous $NH_4Cl$ (20 mL). Ethyl acetate (30 mL) was added and the layers were separated. The organic layer was washed with brine, then dried over $Na_2SO_4$, and concentrated to dryness. The crude product was purified via PTLC (33% EtOAc/hexanes) to give 330 mg (66%) of compound F.

Step 5: Compound F (50 mg, 95 mmol) was dissolved in $CH_2Cl_2$ (10 mL). Triethylsilane (440 mg, 3.825 mmol) was added followed by addition of TFA (47 mg, 0.42 mmol). The reaction mixture was then stirred at room temperature overnight followed by refluxing for 2–3 h. The reaction was quenched by addition of $NaHCO_3$ (sat. aq). It was extracted with $CH_2Cl_2$ (2×20 mL).

The combined organic layers were washed with brine and dried over $Na_2SO_4$. After removing the solvent, the crude product was purified via PTLC (40% EtOAc/hexanes) to give 33 mg (67%) of compound G.

Step 6. Compound F (277 mg, 0.52 mmol) was dissolved in $CH_2Cl_2$ (20 mL) at room temperature. Celite (320 mg) was added followed by addition of PCC (414 mg, 1.9 mmol). The mixture was stirred at room temperature overnight. The solid was filtered off and the organic layer was washed with NaHCO$_3$ and brine. The organic was dried over Na$_2$SO$_4$ and concentrated to dryness. The crude product was purified via PTLC (30% EtOAc/hexanes) to give 71.4 mg (26%) of compound H.

Step 7: Compound H (36.5 mg, 69 mmol) was dissolved in methanol (10 mL) at room temperature. NaOH (2.0 M, 0.52 mL, 1.04 mmol) was added and the mixture was stirred at room temperature for 3 days. The solvent was removed and CH$_2$Cl$_2$ (15 mL) and brine (15 mL) was added and the layers were separated. The aqueous layer was extracted with additional CH$_2$Cl$_2$ (15 mL) and the combined organic layers were dried over Na$_2$SO$_4$ and concentrated to give 21.6 mg (72%) of compound I.

Step 8. Compound I (21.6 mg, 50 mmol) was dissolved in CH$_2$Cl$_2$ (10 mL) and cooled to 0° C. Methanesulfonyl chloride (23 mg, 0.2 mmol) was added followed by addition of pyridine (39 mg, 0.5 mmol). The reaction mixture was slowly warmed up to room temperature and stirred overnight. Brine (15 mL) was added and extracted. The organic layer was dried over Na$_2$SO$_4$ and concentrated to dryness. The crude product was purified via PTLC (4% MeOH/CH$_2$Cl$_2$) to give 4.8 mg (19%) of compound J.

Example V and cooled to −78° C. A solution of n-butyl lithium (1.6 M in hexanes, 5.6 mL, 9.0 mmol) was added and the reaction mixture was stirred for 15 min. The sulfonyl fluoride compound i (prepared in step 3 of Example I) (0.90 g, 3.0 mmol) in THF (3 mL) was added to the reaction mixture at −78° C. and stirred for 3 h. The reaction mixture was slowly warmed to room temperature and quenched with saturated aqueous NH$_4$Cl (20 mL). Ethyl acetate (100 mL) was added and the layers were separated. The organic layer was washed with brine, then dried over Na$_2$SO$_4$, and concentrated to dryness. The crude product was purified via PTLC (50% EtOAc/hexanes) to give 440 mg (42%) of compound B.

Step 2: In a flame dried flask under N$_2$ blanket, compound B (440 mg, 1.3 mmol) was dissolved in dry THF (20 mL) and cooled to −78° C. A solution of t-butyl lithium (1.5 M in hexanes, 1.7 mL, 2.5 mmol) was added and the reaction mixture was stirred for 15 min. 2-fluorophenyl disulfide (0.32 g, 1.3 mmol) in THF (5 mL) was added and the reaction mixture was stirred at −78° C. for 1 h before slowly warming up to 0° C. The reaction mixture was then quenched with saturated aqueous NH$_4$Cl (50 mL). Ethyl acetate (100 mL) was added and the layers were separated. The organic layer was washed with brine, then dried over Na$_2$SO$_4$, and concentrated to dryness. The crude product of compound C was used without further purification.

Step 3: Compound C (270 mg, 0.57 mmol) was dissolved in CH$_2$Cl$_2$ (15 mL). mCPBA (210 mg, 57–86%, 0.69 mmol)

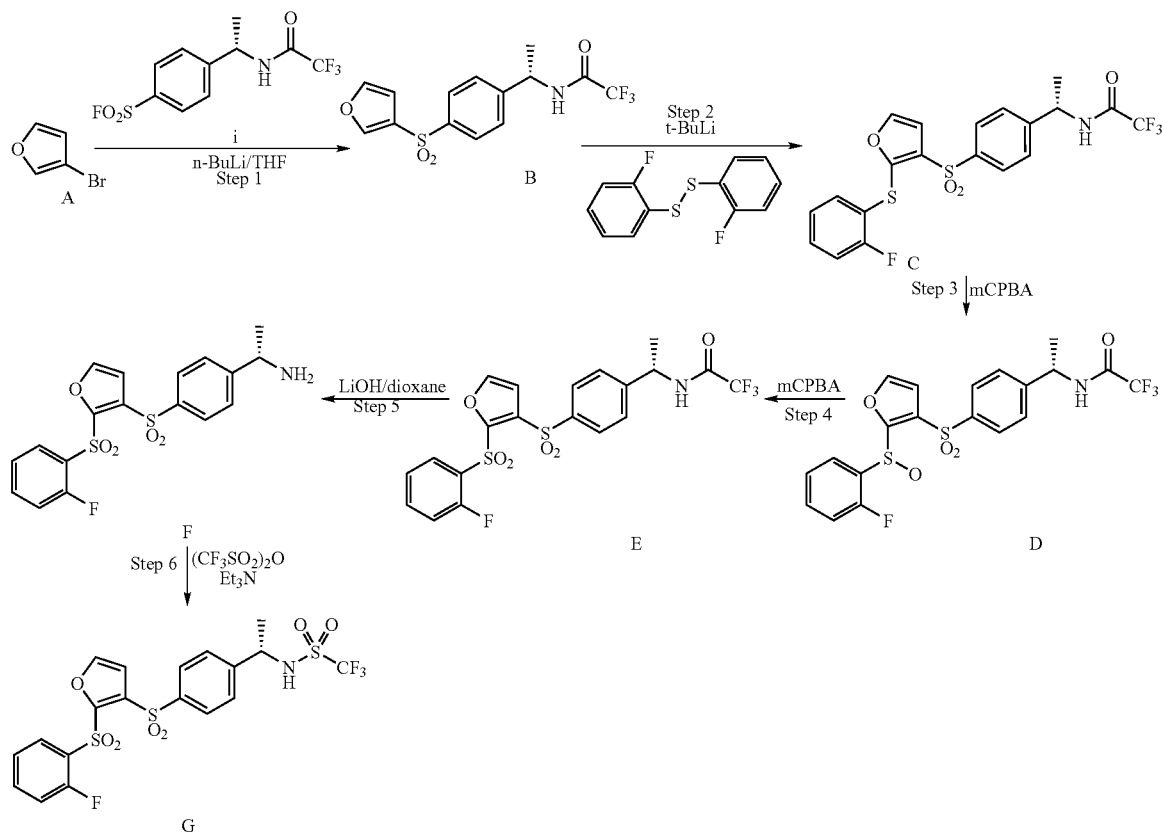

Step 1: In a flame dried flask under N$_2$ blanket, 3-bromofuran (1.3 g, 9.0 mmol) was dissolved in dry THF (50 mL)

was added and the solution was stirred at room temperature for 1 h. The reaction mixture was diluted with CH$_2$Cl$_2$ (50 mL), washed with NaHSO$_3$ (40 mL) and NaHCO$_3$(50 mL). The organic layers were combined and dried over Na$_2$SO$_4$ and concentrated. The crude material was purified via sgc (50% EtOAC/Hexanes) to give 120 mg (43%) of compound D.

Step 4: Compound D (70 mg, 0.14 mmol) was dissolved in CH$_2$Cl$_2$ (10 mL). mCPBA(30 mg, 57–86%, 0.10 mmol) was added and the solution was stirred at room temperature overnight. The reaction mixture was diluted with CH$_2$Cl$_2$ (50 mL), and washed with NaHSO$_3$ (40 mL) and NaHCO$_3$ (50 mL). The organic layers were combined and dried over Na$_2$SO$_4$ and concentrated. The crude material was purified via sgc (50% EtOAC/Hexanes) to give 59 mg (82%) of compound E.

Step 5: Compound E (53 mg, 0.10 mmol) was dissolved in dioxane (5 mL) at room temperature. LiOH (1.0 M, 1 mL, 1 mmol) was added and the mixture was stirred at room temperature for 3 h. The solvent was removed and CH$_2$Cl$_2$ (15 mL) and brine (15 mL) was added and the layers were separated. The aqueous layer was extracted with additional CH$_2$Cl$_2$ (15 mL) and the combined organic layers were dried over Na$_2$SO$_4$ and concentrated to dryness to give compound F.

Step 6: The crude product of compound F was dissolved in CH$_2$Cl$_2$ (5 mL) and cooled to −78° C. Et$_3$N (15 mg, 0.15 mmol) was added followed by the addition of trifluoromethanesulfonic anhydride (34 mg, 0.12 mmol). The reaction mixture was stirred for 2 h before warming up to 0° C. Brine (15 mL) was added and the product was extracted with CH$_2$Cl$_2$ (50 mL). The organic layer was dried over Na$_2$SO$_4$ and concentrated to dryness. The crude product was purified via PTLC (50% EtOAc/hexanes) to give 35 mg of compound G.

Example VI

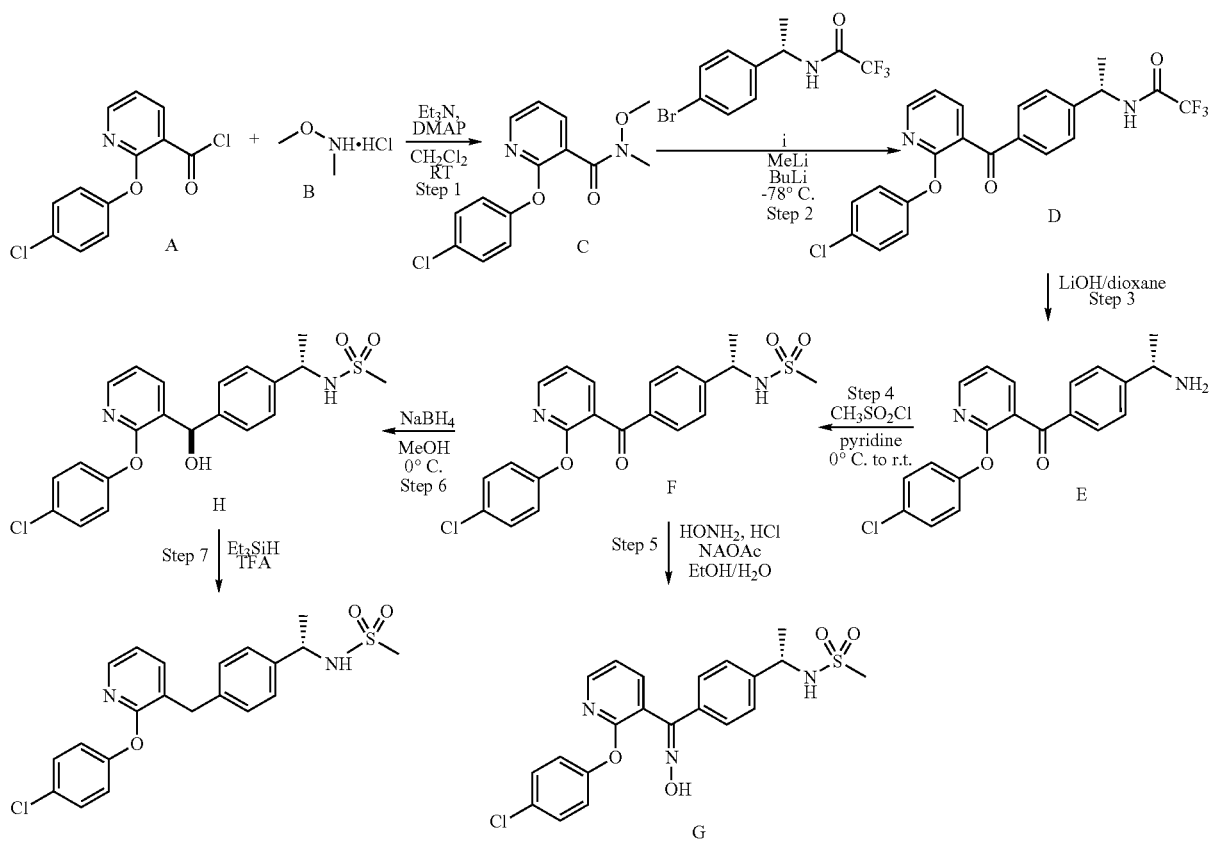

Step 1: To a suspension of N,O-dimethylhydroxylamine (compound B), hydrogen chloride (0.80 g, 8.2 mmol) in methylene chloride (35 mL) was added Et$_3$N (1.0 g, 9.8 mmol). It was stirred at room temperature for 10 min. To the resulting solution was added a solution of 2-(4-chlorophenoxy) pyridine (compound A) (2.0 g, 7.5 mmol.) (obtained from Maybridge Ltd. UK) in methylene chloride (40 mL) dropwise. The reaction mixture was stirred at room temperature overnight and H$_2$O (40 mL) was added. The organic layer was separated and washed with brine and dried over Na$_2$SO$_4$ and concentrated. The crude product was purified via sgc (25% EtOAc/hexanes) to give 2.2 g (88%) of compound C.

Step 2: In a flame dried flask under N$_2$ blanket, compound i (prepared in step 3 of Example IV) (0.1 g, 0.34 mmol) was dissolved in dry THF (20 mL) and cooled to −78° C. A solution of methyl lithium (1.4 M in hexanes, 0.27 mL, 0.37 mmol) was added and the reaction mixture was stirred for 15 min. A solution of n-butyl lithium (1.6 M in hexanes, 0.23 mL, 0.37 mmol) was added and the reaction mixture was stirred for 30 min. Compound C (0.12 g, 0.41 mmol) in THF (3 mL) was added to the reaction mixture at −78° C. and was slowly warmed to −10° C. The reaction mixture was then quenched with saturated aqueous NH₄Cl (20 mL). Ethyl acetate (30 mL) was added and the layers were separated. The organic layer was washed with brine, then dried over Na₂SO₄, and concentrated to dryness. The crude product was purified via PTLC (40% EtOAc/hexanes) to give 44 mg (29%) of compound D.

Step 3: Compound D (39 mg, 0.09 mmol) was dissolved in dioxane (3 mL) at room temperature. LiOH (1.0 M, 0.52 mL, 0.52 mmol) was added and the mixture was stirred at room temperature overnight. The solvent was removed and CH₂Cl₂ (15 mL) and brine (15 mL) was added and the layers were separated. The aqueous layer was extracted with additional CH₂Cl₂ (15 mL) and the combined organic layers were dried over Na₂SO₄ and concentrated to dryness to give compound E. This material was used without further purification.

Step 4: The crude product of compound E was dissolved in CH₂Cl₂ (10 mL) and cooled to 0° C. Methanesulfonyl chloride (33 mg, 0.28 mmol) was added followed by addition of pyridine (56 mg, 0.7 mmol). The reaction mixture was slowly warmed up to room temperature and stirred overnight. Brine (15 mL) was added and the product was extracted with CH₂Cl₂ (50 mL). The organic layer was dried over Na₂SO₄ and concentrated to dryness. The crude product was purified via PTLC (50% EtOAc/hexanes) to give 24 mg of compound F as a colorless oil.

Step 5: A solution of compound F (0.28 g, 0.64 mmol) in EtOH (34 mL) and H₂O (7 mL) was treated with NaOAc (1.05 g, 13 mmol) followed by H₂NOH.HCl (0.89 g, 13 mmol). The reaction was stirred at 65° C. for 17 days. EtOH was removed by vacuum. The crude material was dissolved in EtOAc and washed twice with H₂O and once with brine. The organic layer was dried over Na₂SO₄ and concentrated to dryness. The crude product was purified via PTLC (50% EtOAc/hexanes) to give 60 mg (21%) of compound G.

Step 6: To a solution of compound F (0.28 g, 0.65 mmol) in MeOH (20 mL) was added NaBH₄ (0.2 g, 5.2 mmol) at 0° C. and stirred for 0.5 h. H₂O was added to quench the reaction. MeOH was removed by vacuum. The mixture was extracted with methylene chloride (3×25 mL) and the combined organic layers were washed with brine and dried over Na₂SO₄. Compound H was obtained by removing the organic solvent. It gave 0.28 g of compound H.

Step 7. To a solution of compound H (0.28 g, 0.64 mmol) in methylene chloride (25 mL) was added Et₃SiH (1.5 g, 13 mmol) and TFA (0.28 g, 5.1 mmol). The reaction mixture was stirred at room temperature for 5 days. NaHCO₃ aq. was added to quench the reaction. The product was extracted with methylene chloride three times. The combined extracts were washed with brine. The organic layer was dried over Na₂SO₄ and concentrated to dryness. The crude product was purified via PTLC (50% EtOAc/hexanes) to give 30 mg (11%) of compound I.

Example VII

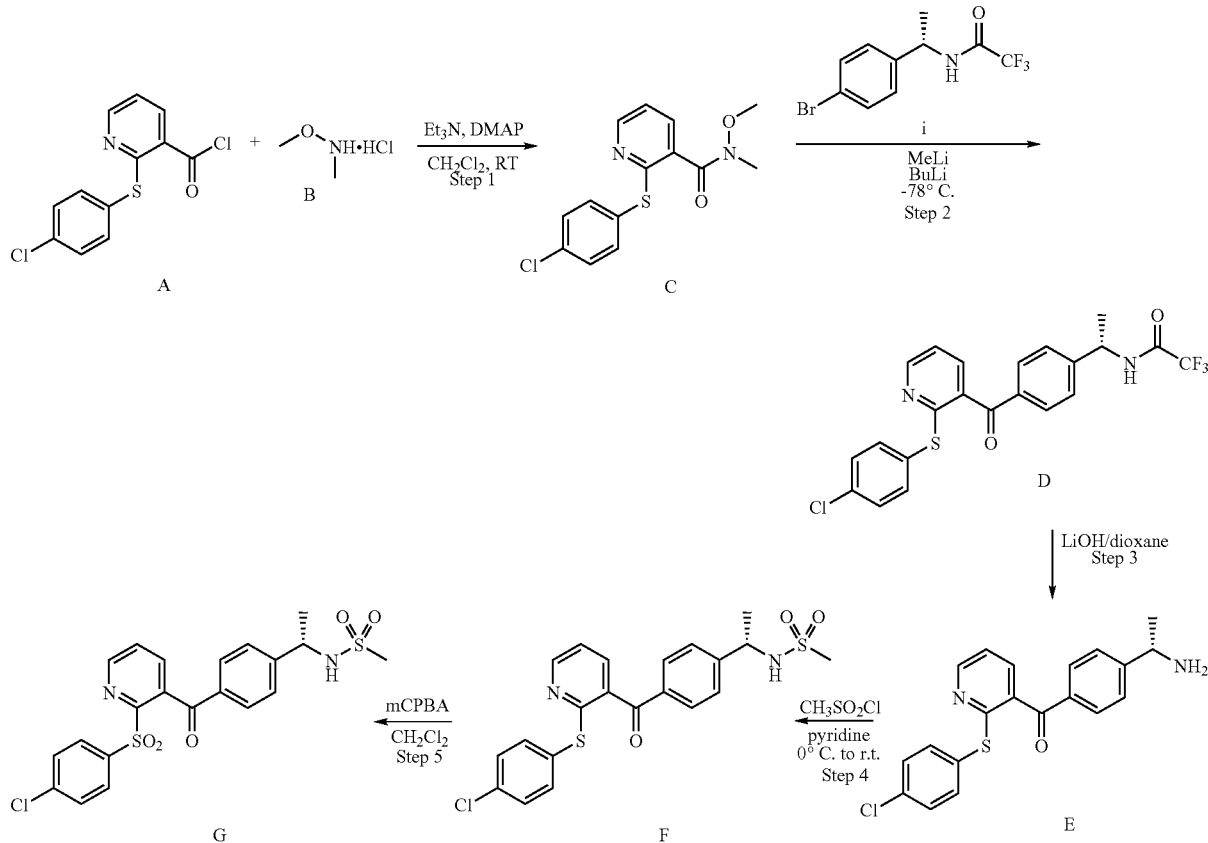

Step 1: To a suspension of N,O-dimethylhydroxylamine hydrogen chloride (compound B) (0.75 g, 7.7 mmol) in methylene chloride (35 mL) was added Et$_3$N (0.94 g, 9.2 mmol). It was stirred at room temperature for 10 min. To the resulting solution was added a solution of 2-(4-chlorophenylthio) pyridine (compound A) (2.0 g, 7.0 mmol.) (obtained from Maybridge Chemical Company Ltd., UK) in methylene chloride (40 mL) dropwise. The reaction mixture was stirred at room temperature overnight and water (40 mL) was added. The organic layer was separated and washed with brine and dried over Na$_2$SO$_4$ and concentrated. The crude product was purified via sgc (25% EtOAc/hexanes) to give 2.14 g (99%) of compound C.

Step 2: In a flame dried flask under N$_2$ blanket, compound i (prepared in step 3 of Example IV) (0.1 g, 0.34 mmol) was dissolved in dry THF (20 mL) and cooled to −78° C. A solution of methyl lithium (1.4 M in hexanes, 0.27 mL, 0.37 mmol) was added and the reaction mixture was stirred for 15 min. A solution of n-butyl lithium (1.6 M in hexanes, 0.23 mL, 0.37 mmol) was added and the reaction mixture was stirred for 30 min. Compound C (0.12 g, 0.41 mmol) in THF (3 mL) was added to the reaction mixture at −78° C. The mixture was slowly warmed to −10° C. and was then quenched with saturated aqueous NH$_4$Cl (20 mL). Ethyl acetate (30 mL) was added and the layers were separated. The organic layer was washed with brine, then dried over Na$_2$SO$_4$, and concentrated to dryness. The crude product was purified via PTLC (40% EtOAc/hexanes) to give 96 mg (61%) of compound D.

Step 3: Compound D (93 mg, 0.2 mmol) was dissolved in dioxane (3 mL) at room temperature. LiOH (1.0 M, 1.2 mL, 1.2 mmol) was added and the mixture was stirred at room temperature overnight. The solvent was removed and CH$_2$Cl$_2$ (15 mL) and brine (15 mL) were added and the layers were separated. The aqueous layer was extracted with additional CH$_2$Cl$_2$ (15 mL) and the combined organic layers were dried over Na$_2$SO$_4$ and concentrated to dryness to give compound E.

Step 4: The crude product of compound E was dissolved in CH$_2$Cl$_2$ (10 mL) and cooled to 0° C. Methanesulfonyl chloride (94 mg, 0.8 mmol) was added followed by addition of pyridine (162 mg, 2.0 mmol). The reaction mixture was slowly warmed up to room temperature and stirred overnight. Brine (15 mL) was added and extracted. The organic layer was dried over Na$_2$SO$_4$ and concentrated to dryness. The crude product was purified via PTLC (50% EtOAc/hexanes) to give 54 mg of compound F.

Step 5: Compound F (30 mg, 0.067 mmol) was dissolved in CH$_2$Cl$_2$ (15 mL). mCPBA(33.2 mg, 57–86%, 0.13 mmol) was added and the solution was stirred at room temperature overnight. The reaction mixture was diluted with CH$_2$Cl$_2$ (50 mL) and washed with NaHSO$_3$ (30 mL) and NaHCO$_3$ (30 mL). The organic layers were combined and dried over Na$_2$SO$_4$ and concentrated. The crude material was purified via sgc (50% EtOAC/Hexanes) to give 28 mg (86%) of compound G.

Example VIII

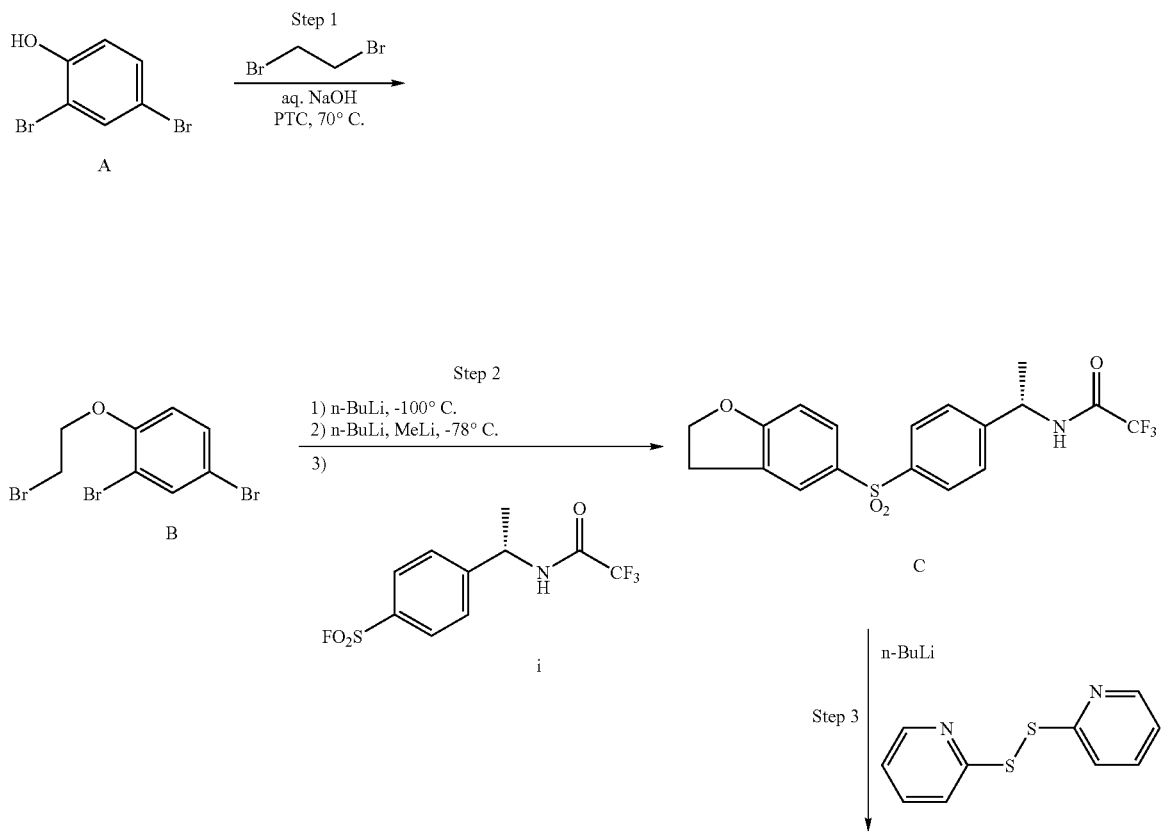

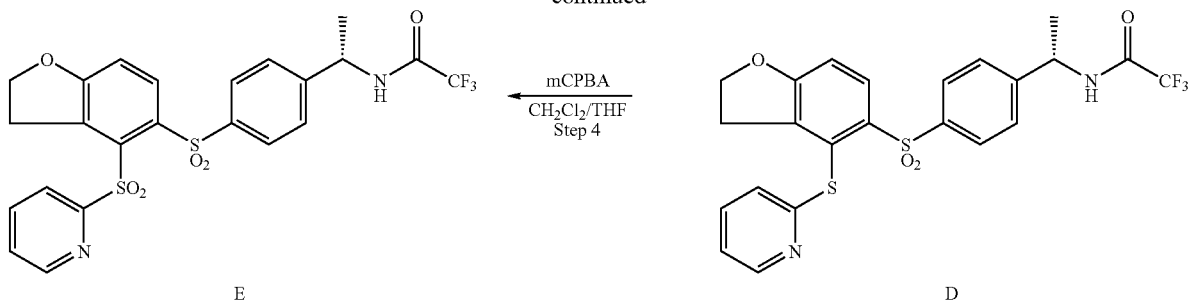

Step 1: A mixture of 2,4-dibromophenol (compound A) (5 g, 0.02 mol), 1,2 dibromoethane (37 mL, 0.4 mol) (obtained from Aldrich Chemical Company, Inc. Milwaukee, Wis.), and aq. NaOH (14 ml, 3N) Bu$_4$N$^+$HSO$_4$$^-$ (0.34 g, 1 mmol) was stirred vigorously at 70° C. for 10 h. The mixture was cooled to room temperature. CH$_2$Cl$_2$ (100 mL) was added. The organic layer was washed with NaOH(1N), HCl(1N), water and brine, respectively. The organic layer was dried over Na$_2$SO$_4$, and concentrated to dryness. The crude product was purified by recrystallization from ether:hexane to give 3.2 g (45%) of pure compound B.

Step 2: In a flame dried flask under N$_2$ blanket, compound B (2.6 g, 7.2 mmol) was dissolved in dry THF (40 mL) and cooled to −100° C. A solution of n-butyl lithium (2.5 M in hexanes, 3.17 mL, 7.9 mmol) was added and the reaction mixture was stirred for 30 min. The reaction mixture was warmed to −78° C. An additional equivalent of n-BuLi (2.5 M in hexanes, 3.17 mL, 7.9 mmol) was added and it was stirred for 30 min followed by addition of MeLi (1.4 M, 5.6 mL, 7.8 mmol). To the resulting mixture was added compound i (prepared in step 3 of Example I) (2.2 g, 7.2 mmol) in THF (5 mL) and the reaction mixture was stirred for 2 h before quenching with aq NH$_4$Cl. The reaction was diluted with EtOAc and extracted with water (100 mL) and brine (50 mL), respectively. The organic layer was dried over Na$_2$SO$_4$, and concentrated to dryness. The crude product was purified via PTLC (40% EtOAc/hexanes) to give 1.2 g (42%) of compound C.

Step 3: In a flame dried flask under N$_2$ blanket, compound C (1.1 g, 2.8 mmol) was dissolved in dry THF (20 mL) and cooled to −78° C. A solution of n-butyl lithium (1.7 M in hexanes, 3.6 mL, 6.0 mmol) was added and the reaction mixture was stirred for 45 min. Pyridine disulfide (0.6 g, 3.0 mmol) in THF (5 mL) was added and the reaction mixture was stirred at −78° C. for 2 h before slowly warming up to room temperature. The reaction mixture was then quenched with saturated aqueous NH$_4$Cl (50 mL). Ethyl acetate (100 mL) was added and the layers were separated. The organic layer was washed with brine, then dried over Na$_2$SO$_4$, and concentrated to dryness. The crude product was purified via sgc (25% EtOAc/hexanes) to give 670 mg of compound D.

Step 4: Compound D (670 mg, 1.3 mmol) was dissolved in CH$_2$Cl$_2$ (50 mL) with THF (0.2 mL). mCPBA(740 mg, 57–86%, 2.9 mmol) was added and the solution was stirred at room temperature overnight. The reaction mixture was taken up by CH$_2$Cl$_2$ and washed with NaHSO$_3$ (40 mL) and NaHCO$_3$(50 mL). The organic layers were combined and dried over Na$_2$SO$_4$ and concentrated. The crude material was purified via sgc (50% EtOAC/Hexanes) to give 300 mg (42%) of compound E.

Example IX

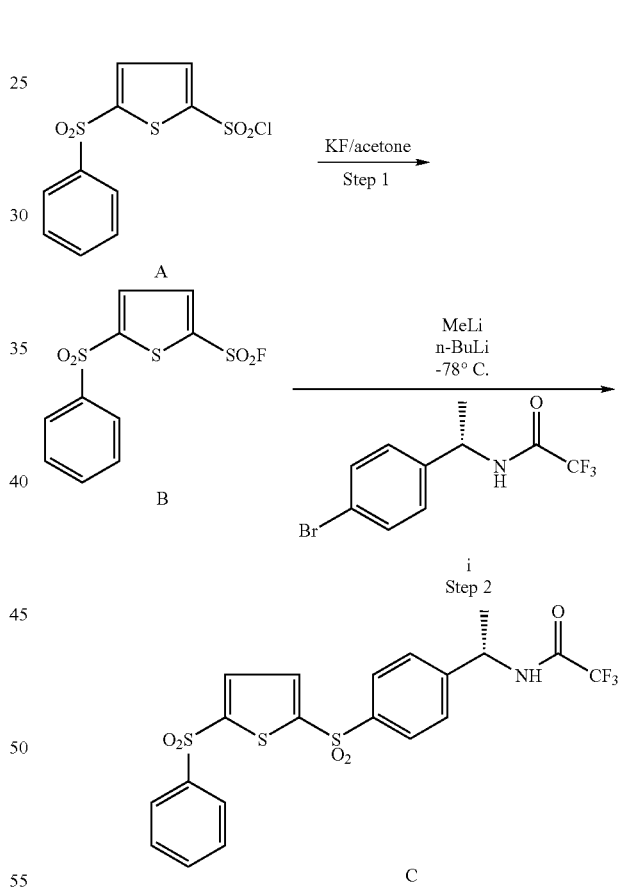

Step 1: Commercially available sulfonyl chloride (compound A) (1 g, 3 mmol) (obtained from Lancaster Synthesis Ltd., UK) in 20 mL acetone was treated with excess potassium fluoride (1.4 g, 24 mmol) in a 20 mL aqueous solution. The reaction was stirred for 3 h and then diluted with 100 mL ethylacetate. The organics were washed with 2×50 mL water, dried over MgSO$_4$ and concentrated to yeild pure solid sulfonyl fluoride (compound B) (0.8 g).

Step 2: Bromophenethyamine trifluoroacetamide (compound i prepared in step 3 of example IV) (0.5 g, 18 mmol)

in 25 mL anhydrous THF was treated with methyllithium (2 mmol) at −78° C. After stirring the mixture for 15 min, nBuLi (2 mmol) was added. The reaction mixture was stirred for 0.5 h and then sulfonyl fluoride (compound B) (0.5 g) was added in a 10 mL THF solution. The reaction mixture was stirred for 3 h, and at the same time, the temperature was allowed to rise to 0° C. The reaction mixture was then quenched with aqueous ammonium chloride. The reaction mixture was diluted with ethyl acetate (100 mL) and washed with water (2×50 mL) and brine (1×25 mL). The organics were dried and concentrated under reduced pressure. The crude product was purified by prep. plate chromatography using 30% ethylacetate/hexane as the developing solvent to obtain compound C (0.06 g).

Using the appropriate starting materials in the procedures described above or modifications of those procedures well known to those skilled in the art, the compounds shown in the following tables were prepared. The compound numbers in the TABLE OF COMPOUNDS below correspond to the compound numbers in Table 1.

| Compound Number | Structure |
|---|---|
| 1 | *structure* |
| 2 | *structure* |
| 3 | *structure* |
| 4 | *structure* |

TABLE OF COMPOUNDS

-continued

TABLE OF COMPOUNDS

| Compound Number | Structure |
|---|---|
| 5 | 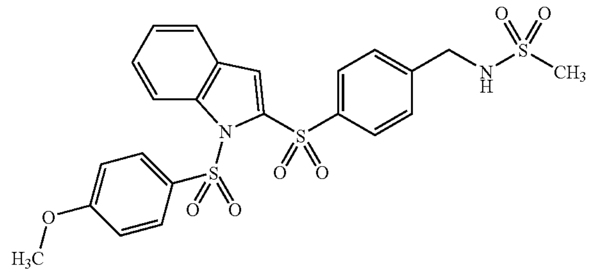 |
| 6 | 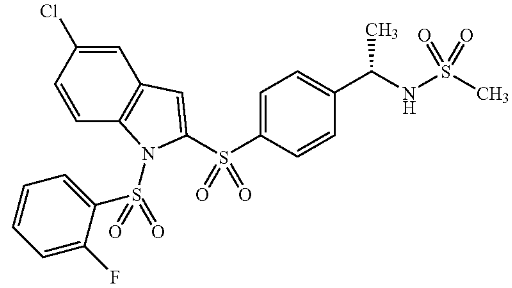 |
| 7 | 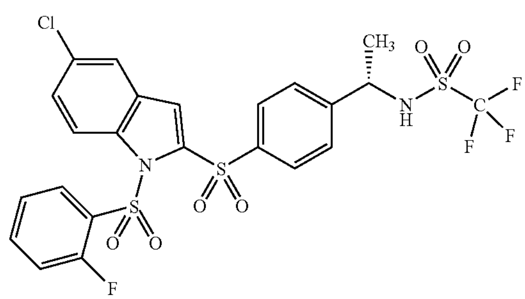 |
| 8 | 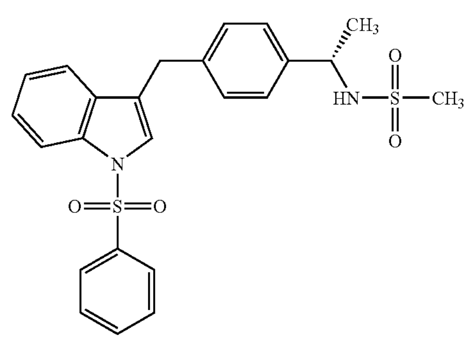 |
| 9 | 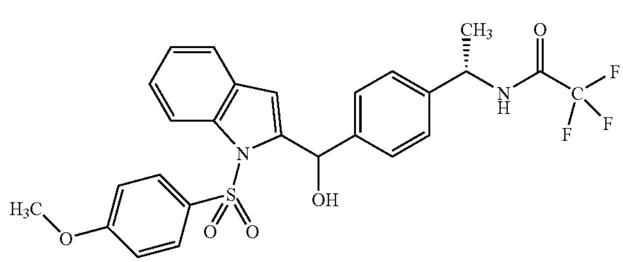 |

-continued
TABLE OF COMPOUNDS
| Compound Number | Structure |
|---|---|
| 10 | 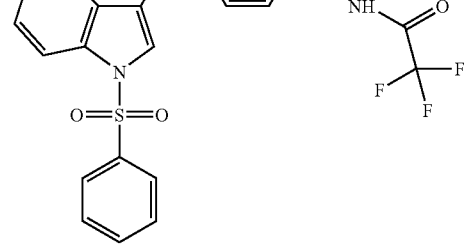 |
| 11 | 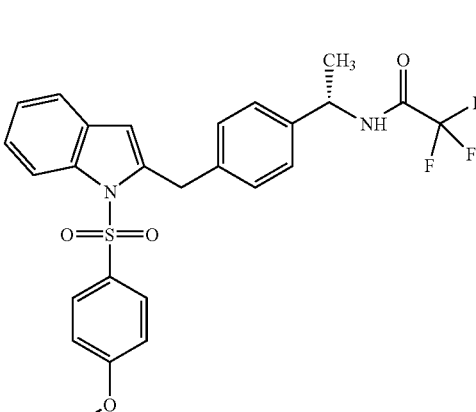 |
| 12 | 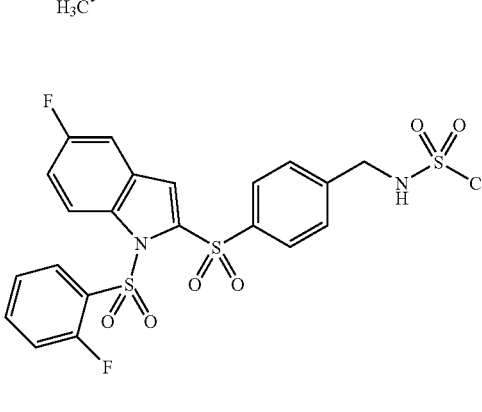 |
| 13 | 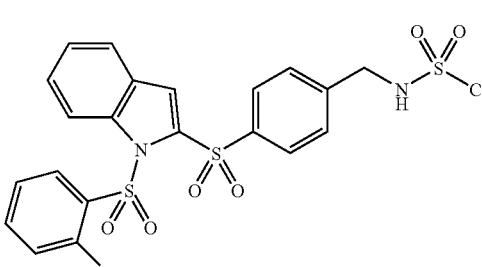 |

-continued
TABLE OF COMPOUNDS
| Compound Number | Structure |
|---|---|
| 14 | 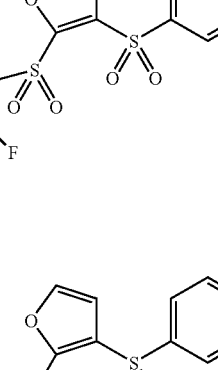 |
| 15 | 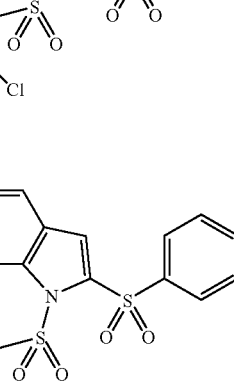 |
| 16 | 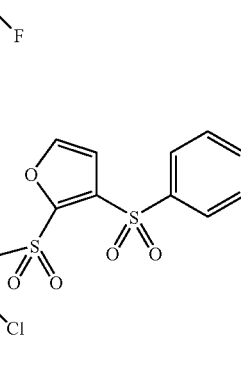 |
| 17 | 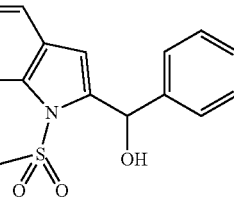 |
| 18 | 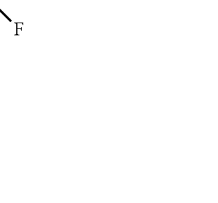 |

-continued

TABLE OF COMPOUNDS

| Compound Number | Structure |
|---|---|
| 19 | 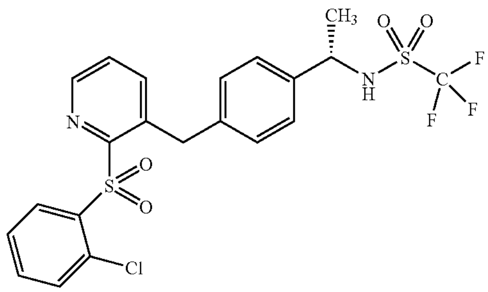 |
| 20 | 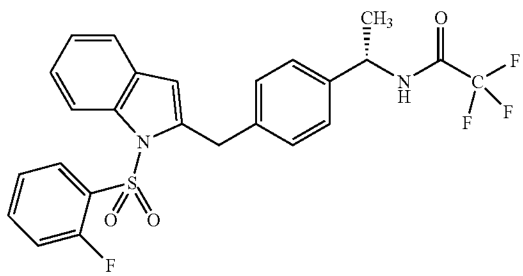 |
| 21 | 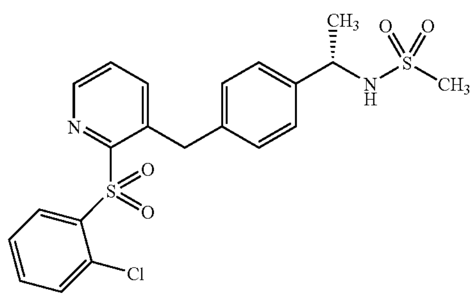 |
| 22 | 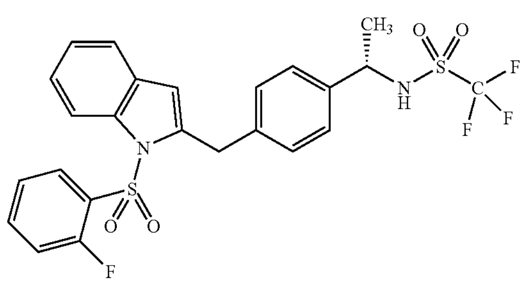 |
| 23 | 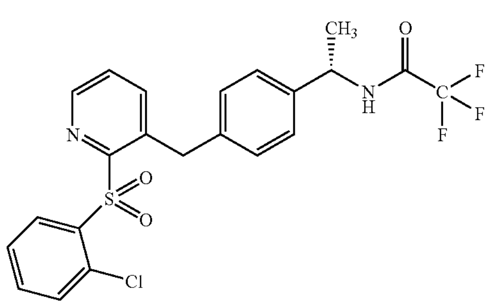 |

-continued

TABLE OF COMPOUNDS

| Compound Number | Structure |
|---|---|
| 24 | 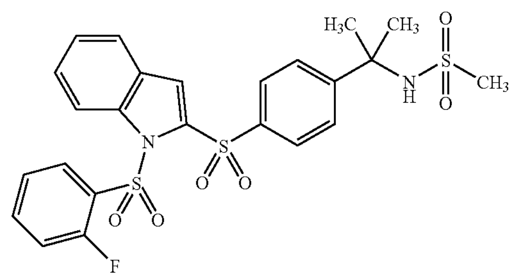 |
| 25 | 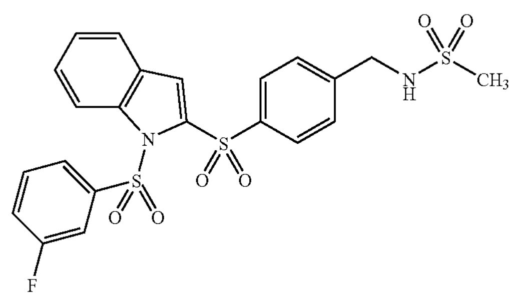 |
| 26 | 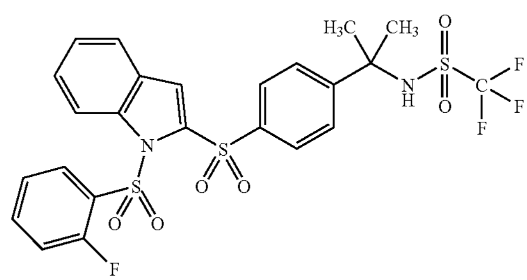 |
| 27 | 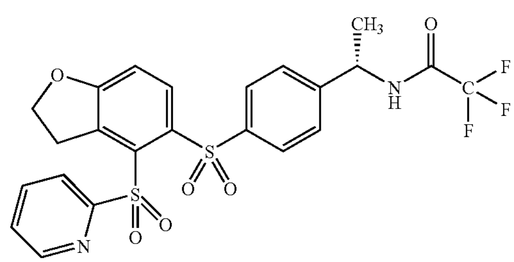 |
| 28 | 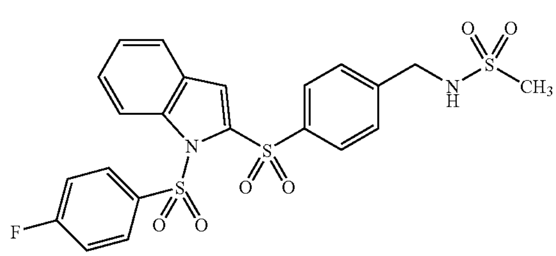 |

-continued

TABLE OF COMPOUNDS

| Compound Number | Structure |
|---|---|
| 29 | 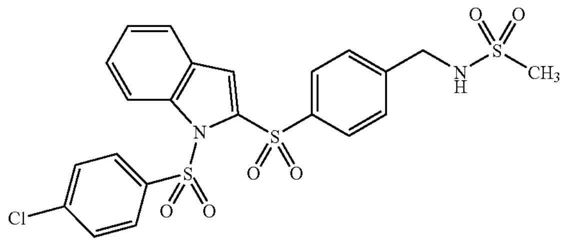 |
| 30 | 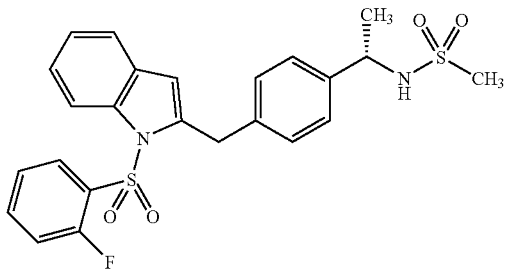 |
| 31 | 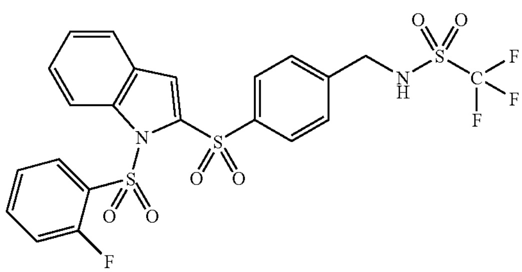 |
| 32 | 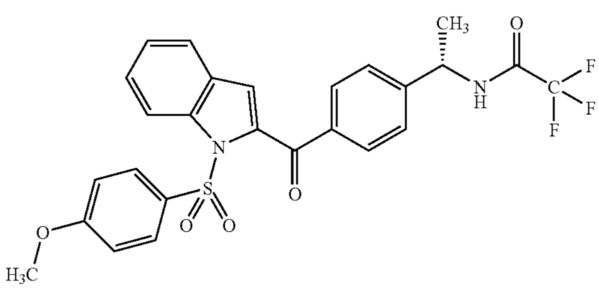 |
| 33 | 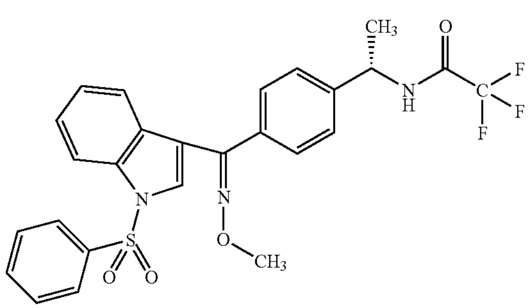 |

-continued

TABLE OF COMPOUNDS

| Compound Number | Structure |
|---|---|
| 34 | 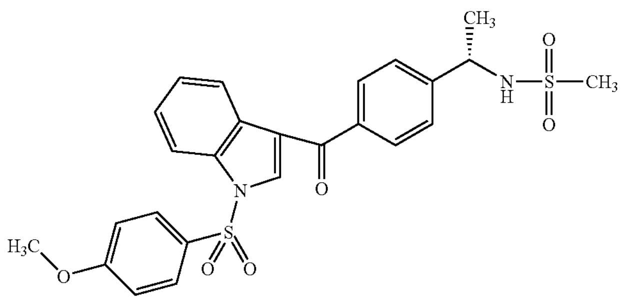 |
| 35 | 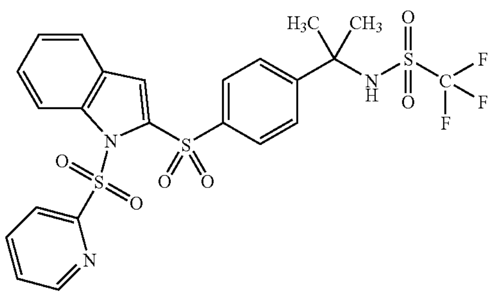 |
| 36 | 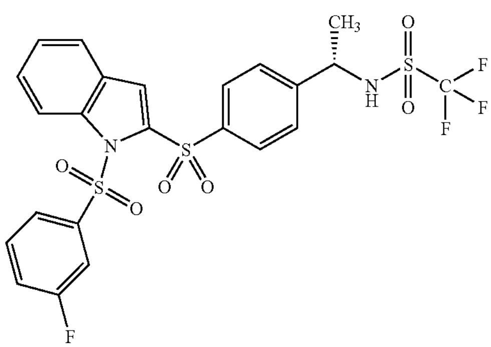 |
| 37 | 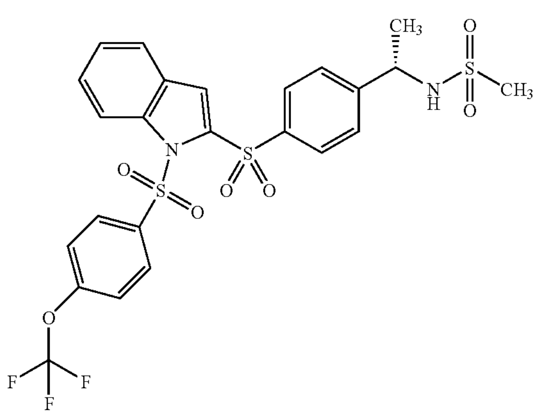 |

-continued

TABLE OF COMPOUNDS

| Compound Number | Structure |
|---|---|
| 38 | 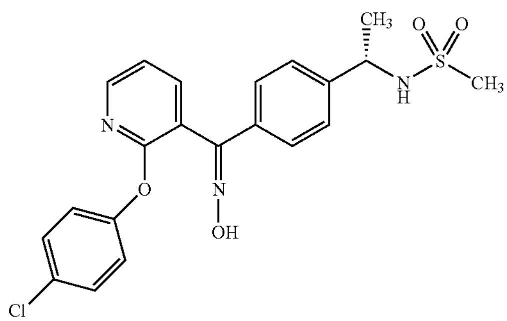 |
| 39 | 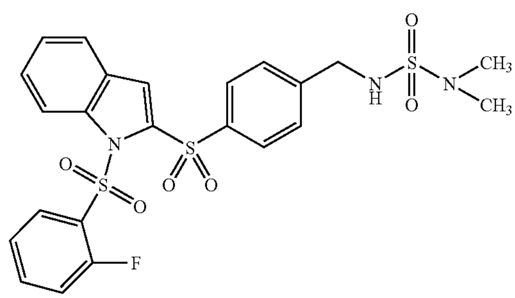 |
| 40 | 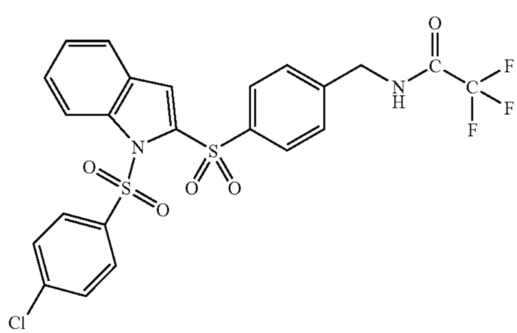 |
| 41 | 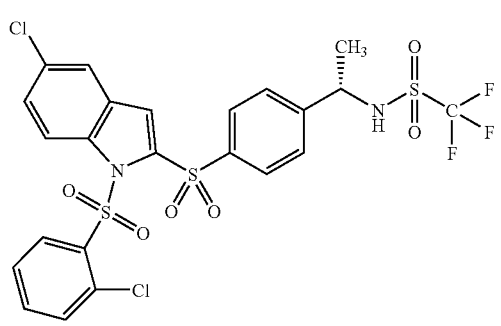 |

-continued

TABLE OF COMPOUNDS

| Compound Number | Structure |
| --- | --- |
| 42 | 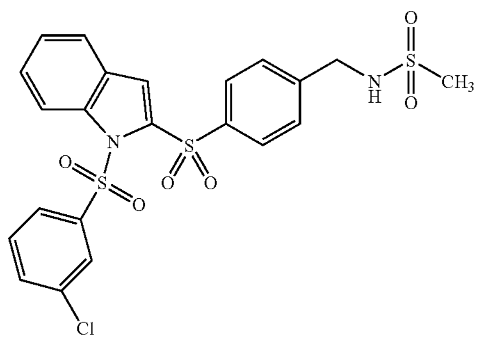 |
| 43 | 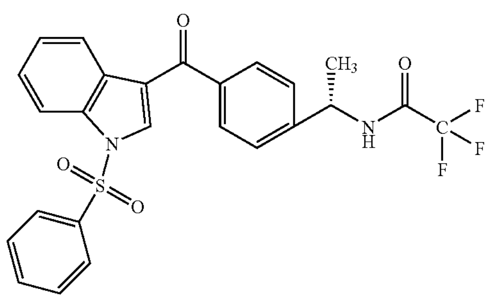 |
| 44 | 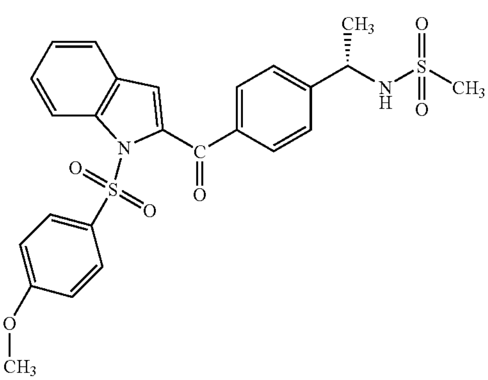 |
| 45 | 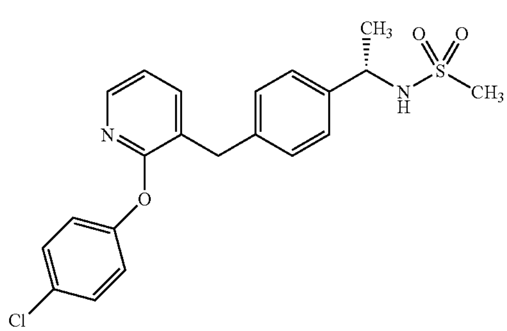 |

-continued

| TABLE OF COMPOUNDS | |
|---|---|
| Compound Number | Structure |
| 46 | |
| 47 | |
| 48 | |
| 49 | |

TABLE OF COMPOUNDS

| Compound Number | Structure |
| --- | --- |
| 50 | 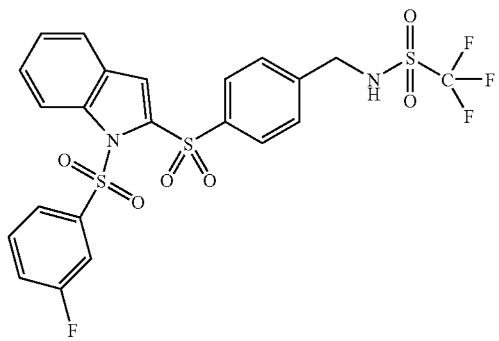 |
| 51 | 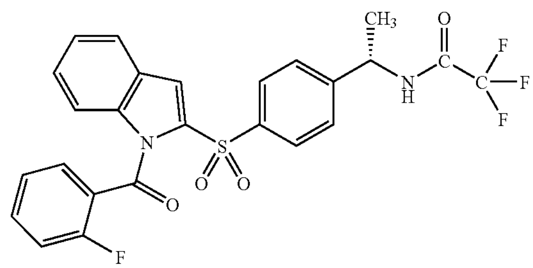 |
| 52 | 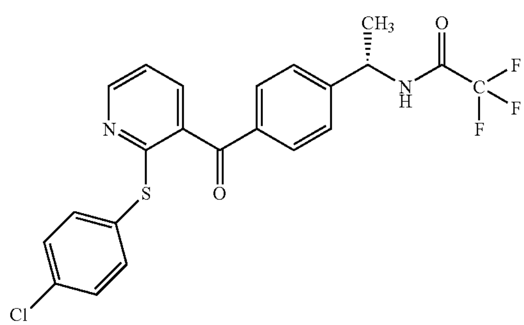 |
| 53 | 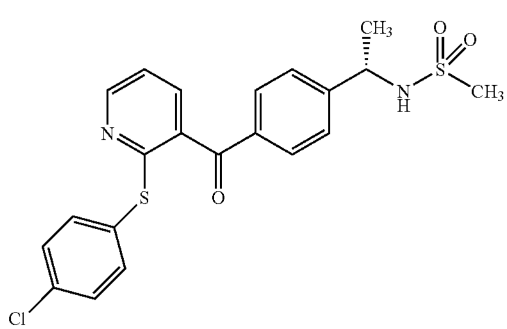 |

-continued

TABLE OF COMPOUNDS

| Compound Number | Structure |
|---|---|
| 54 | 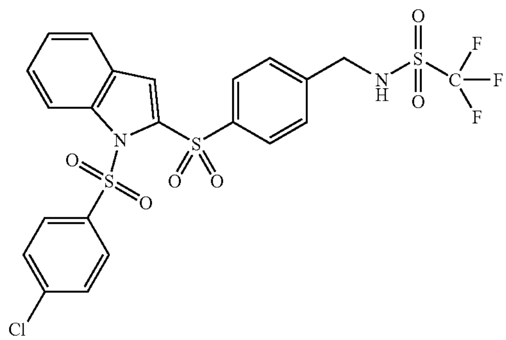 |
| 55 | 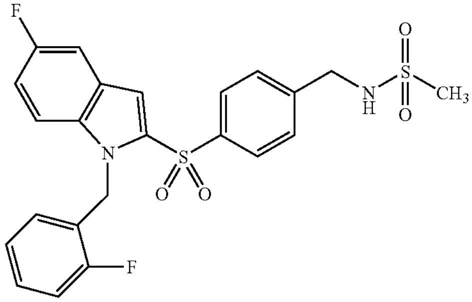 |
| 56 | 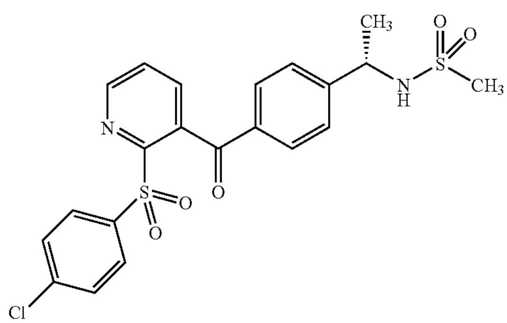 |
| 57 | 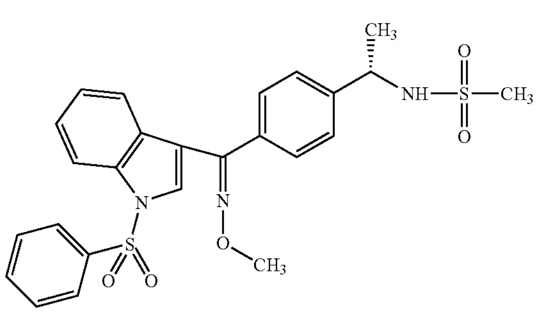 |

-continued
TABLE OF COMPOUNDS
| Compound Number | Structure |
| --- | --- |
| 58 | 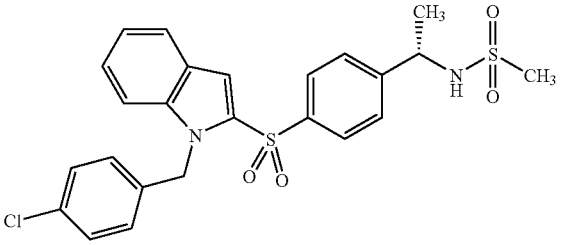 |
| 59 | 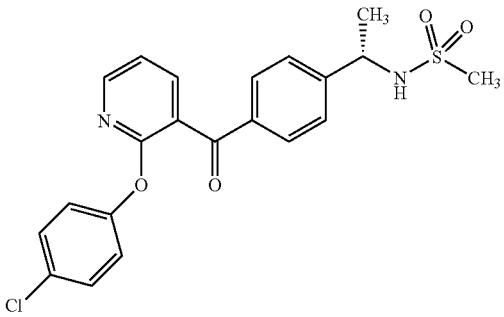 |
| 60 | 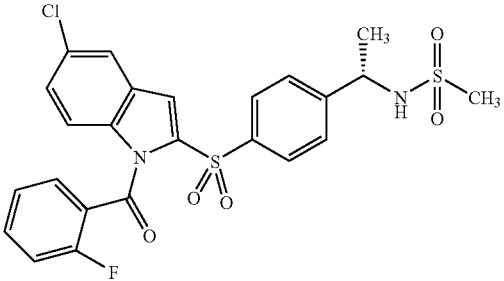 |
| 61 | 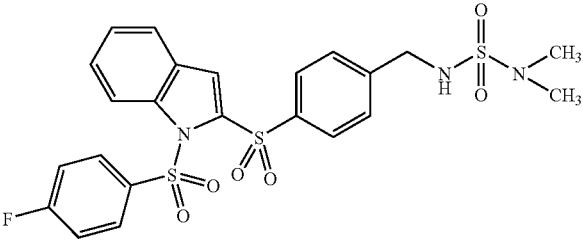 |
| 62 | 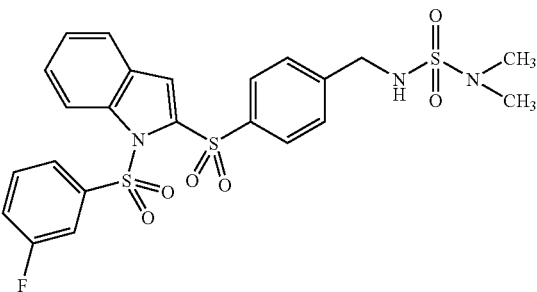 |

-continued
TABLE OF COMPOUNDS
| Compound Number | Structure |
|---|---|
| 63 | 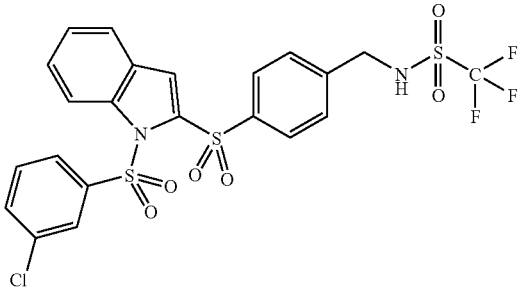 |
| 64 | 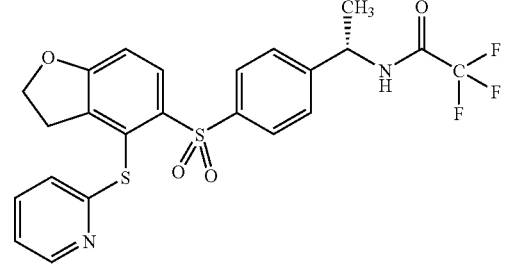 |
| 65 | 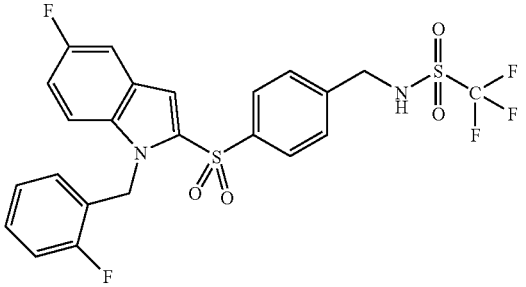 |
| 66 | 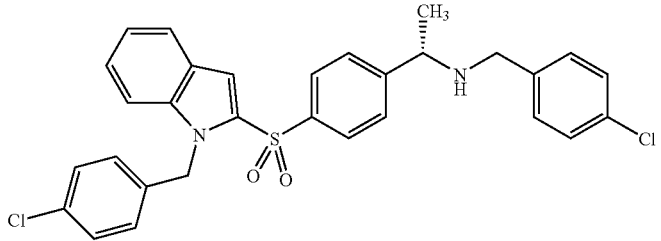 |
| 67 | 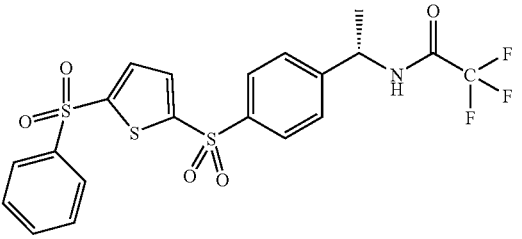 |

It will be understood that various modifications can be made to the embodiments and examples disclosed herein. Therefore, the above description should not be construed as limiting, but merely as exemplifications of preferred embodiments. Those skilled in the art will envision various modifications within the scope and spirit of the claims appended hereto.

What is claimed is:

1. A compound represented by the structural formula:

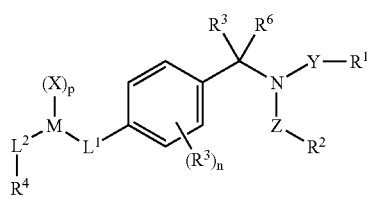

I or a pharmaceutically acceptable salt or solvate thereof; wherein:

$R^1$ is selected from the group consisting of hydrogen, substituted or unsubstituted alkyl, substituted or unsubstituted alkenyl, haloalkyl, —$N(R^7)_2$, substituted or unsubstituted cycloalkyl, substituted or unsubstituted cycloheteroalkyl, substituted or unsubstituted aryl, and substituted or unsubstituted heteroaryl, wherein the term "substituted" means being substituted with $(X)_p$;

$R^2$ is selected from the group consisting of hydogen, substituted or unsubstituted alkyl, substituted or unsubstituted alkenyl, haloalkyl, —$N(R^7)_2$, substituted or unsubstituted cyoloalkyl, substituted or unsubstituted cycloheteroalkyl, substituted or unsubstituted aryl, and substituted or unsubstituted heteroaryl, wherein the term "substituted" means being substituted with $(X)_p$;

$R^3$ is selected from the group consisting of alkyl, heteroalkyl, aryl, hetroaryl, Br, Cl, F, $CF_3$, $OCF_2H$, $OCF_3$, and alkoxy, wherein $R^3$ can be the same or different and is independently selected when n>1;

$R^4$ is selected from the group consisting of H, substituted or unsubstituted alkyl, substituted or unsubstituted alkenyl, substituted or unsubstituted cycloalkyl, substituted or unsubstituted cycloheteroalkyl, substituted or unsubstituted aryl, and substituted or unsubstituted heteroaryl, wherein the term "substituted" means being substituted with $(X)_p$;

$R^5$ and $R^6$, which can be the same or different, are independently selected from the group consisting of H, substituted or unsubstituted alkyl, substituted or unsubstituted alkenyl, substituted or unsubstituted cycloalkyl, substituted or unsubstituted cycloheteroalkyl, substituted or unsubstituted aryl, and substituted or unsubstituted heteroaryl, wherein the term "substituted" means being substituted with $(X)_p$;

$R^7$ is selected from the group consisting of hydrogen, substituted or unsubstituted alkyl, substituted or unsubstituted alkenyl, haloalkyl, substituted or unsubstituted cycloalkyl, substituted or unsubstituted cycloheteroalkyl, substituted or unsubstituted aryl, and substituted or unsubstituted heteroaryl, or two $R^7$ groups can form a ring of 4–7 carbon atoms, wherein the term "substituted" means being substituted with $(X)_p$;

$L^1$ is selected from the group consisting of —$S(O_2)$—, —$S(O)$—, and —S—;

$L^2$ is selected from the group consisting of —$S(O_2)$—, —$S(O)$—, —S—, and —$C(O)$—;

M is

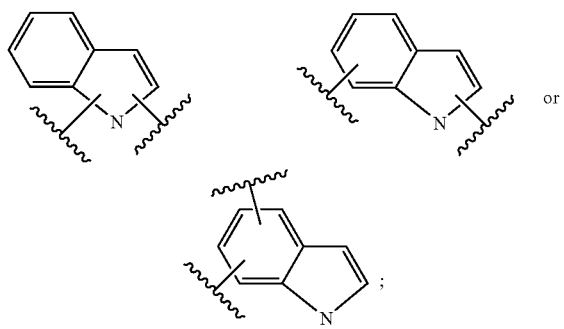

n is 0–4;

p is 0–5;

X can be the same or different and is selected from the group consisting of Br, Cl, F, $CF_3$, OH, $OCF_2H$, $OCF_3$, alkoxy, alkyl, cycloalkyl, —O-cycloalkyl, heteroalkyl, —$C(O)N(R^7)_2$, —$S(O_2)R^2$, and —$OS(O_2)R^2$, wherein X is independently selected when p>1;

Y is —$S(O_2)$— and

Z is selected from the group consisting of a covalent bond, —$CH_2$—, —$S(O_2)$—, and —$C(O)$—, with the following proviso:

when Z is a covalent bond, $R^2$ is directly linked to the nitrogen atom shown in formula I.

2. A compound according to claim 1, wherein $L^1$ is —$S(O_2)$—.

3. A compound according to claim 1, wherein $L^2$ is —$S(O_2)$—.

4. A compound according to claim 1, wherein $R^1$ is $CH_3$ or $CF_3$.

5. A compound according to claim 1, wherein $R^5$ and $R^6$, which can be the same or different, are H or $CH_3$.

6. A compound according to claim 1, wherein n is 0.

7. A compound according to claim 1, wherein X is Cl.

8. A compound according to claim 1, wherein Z is a covalent bond, n is 0, $R^2$ is H, and $R^1$, $R^4$, $R^5$, $R^6$, M, $L^1$, $L^2$, p, Y and X are defined in the following table:

| # | $R^1$ | $R^5$, $R^6$ | $R^4$ (with liking point to $L^2$) | M (with linking points to $L^1$, $L^2$ and X) | $L^1$ | $L^2$ | Y | p, X |
|---|-------|--------------|-------------------------------------|------------------------------------------------|-------|-------|---|------|
| 1 | $CH_3$ | $CH_3$, H | (phenyl-F) | (indole) | —$S(O_2)$— | —$S(O_2)$— | —$S(O_2)$— | 0 |

-continued

| # | R¹ | R⁵, R⁶ | R⁴ (with linking point to L²) | M (with linking points to L¹, L² and X) | L¹ | L² | Y | p, X |
|---|---|---|---|---|---|---|---|---|
| 2 | CF₃ | CH₃, H | 2-F-phenyl | indole (L¹ at 2, L² at N) | —S(O₂)— | —S(O₂)— | —C(O)— | 0 |
| 3 | CF₃ | CH₃, H | 2-F-phenyl | furan (L¹, L²) | —S(O₂)— | —S(O₂)— | —S(O₂)— | 0 |
| 4 | CF₃ | CH₃, H | 4-OCH₃-phenyl | indole (L¹ at 2, L² at N) | —S(O₂)— | —S(O₂)— | —C(O)— | 0 |
| 5 | CH₃ | H, H | 4-OCH₃-phenyl | indole (L¹ at 2, L² at N) | —S(O₂)— | —S(O₂)— | —S(O₂)— | 0 |
| 6 | CH₃ | CH₃, H | 2-F-phenyl | indole with X at 5 | —S(O₂)— | —S(O₂)— | —S(O₂)— | 1, Cl |
| 7 | CF₃ | CH₃, H | 2-F-phenyl | indole with X at 5 | —S(O₂)— | —S(O₂)— | —S(O₂)— | 1, Cl |
| 8 | CH₃ | CH₃, H | phenyl | indole (L¹ at 2, L² at N) | —CH₂— | —S(O₂)— | —S(O₂)— | 0 |
| 9 | CF₃ | CH₃, H | 4-OCH₃-phenyl | indole (L¹ at 2, L² at N) | —CH(OH)— | —S(O₂)— | —C(O)— | 0 |

-continued

| # | R¹ | R⁵, R⁶ | R⁴ (with liking point to L²) | M (with linking points to L¹, L² and X) | L¹ | L² | Y | p, X |
|---|---|---|---|---|---|---|---|---|
| 10 | CF₃ | CH₃, H | phenyl | indole (N-L², 2-L¹) | —CH₂— | —S(O₂)— | —C(O)— | 0 |
| 11 | CF₃ | CH₃, H | 4-methoxyphenyl | indole (N-L², 2-L¹) | —CH₂— | —S(O₂)— | —C(O)— | 0 |
| 12 | CH₃ | H, H | 2-fluorophenyl | indole (N-L², 2-L¹, 5-X) | —S(O₂)— | —S(O₂)— | —S(O₂)— | 1, F |
| 13 | CH₃ | H, H | 2-fluorophenyl | indole (N-L², 2-L¹) | —S(O₂)— | —S(O₂)— | —S(O₂)— | 0 |
| 14 | CF₃ | CH₃, H | 2-fluorophenyl | furan | —S(O₂)— | —S(O₂)— | —C(O)— | 0 |
| 15 | CF₃ | CH₃, H | 2-chlorophenyl | furan | —S(O₂)— | —S(O₂)— | —C(O)— | 0 |
| 16 | CF₃ | CH₃, H | phenyl | indole (N-L², 2-L¹) | —S(O₂)— | —S(O₂)— | —S(O₂)— | 0 |
| 17 | CF₃ | CH₃, H | 2-chlorophenyl | furan | —S(O₂)— | —S(O₂)— | —S(O₂)— | 0 |
| 18 | CF₃ | CH₃, H | 2-fluorophenyl | indole (N-L², 2-L¹) | —CH(OH)— | —S(O₂)— | —C(O)— | 0 |

-continued
| # | R¹ | R⁵, R⁶ | R⁴ (with linking point to L²) | M (with linking points to L¹, L² and X) | L¹ | L² | Y | p, X |
|---|----|--------|-------------------------------|-----------------------------------------|-----|-----|-----|------|
| 19 | CF₃ | CH₃, H | 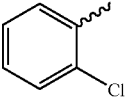 | 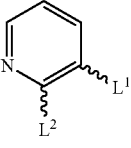 | —CH₂— | —SO₂— | —SO₂— | 0 |
| 20 | CF₃ | CH₃, H | 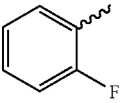 | 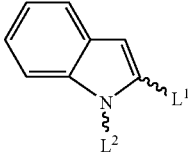 | —CH₂— | —S(O₂)— | —C(O)— | 0 |
| 21 | CH₃ | CH₃, H | 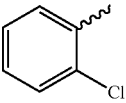 | 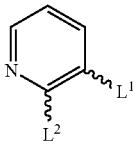 | —CH₂— | —S(O₂)— | —S(O₂)— | 0 |
| 22 | CF₃ | CH₃, H | 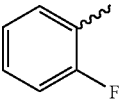 | 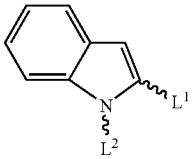 | —CH₂— | —S(O₂)— | —S(O₂)— | 0 |
| 23 | CF₃ | CH₃, H | 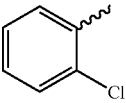 | 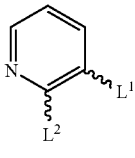 | —CH₂— | —S(O₂)— | —C(O)— | 0 |
| 24 | CH₃ | CH₃, CH₃ | 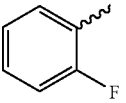 | 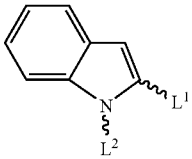 | —S(O₂)— | —S(O₂)— | —S(O₂)— | 0 |
| 25 | CH₃ | H, H | 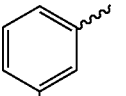 | 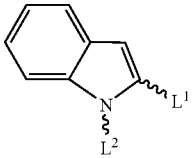 | —S(O₂)— | —S(O₂)— | —S(O₂)— | 0 |
| 26 | CF₃ | CH₃, CH₃ | 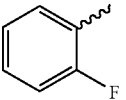 | 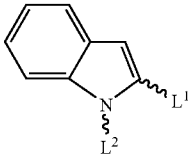 | —S(O₂)— | —S(O₂)— | —S(O₂)— | 0 |
| 27 | CF₃ | CH₃, H | 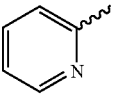 | 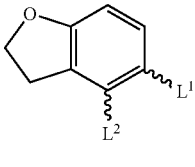 | —S(O₂)— | —S(O₂)— | —C(O)— | 0 |

-continued
| # | R¹ | R⁵, R⁶ | R⁴ (with linking point to L²) | M (with linking points to L¹, L² and X) | L¹ | L² | Y | p, X |
|---|----|--------|-------------------------------|----------------------------------------|-----|-----|---|------|
| 28 | CH₃ | H, H | 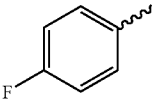 | 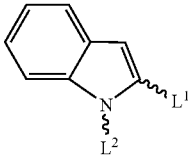 | —S(O₂)— | —S(O₂)— | —S(O₂)— | 0 |
| 29 | CH₃ | H, H | 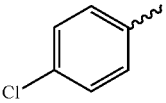 | 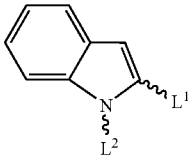 | —S(O₂)— | —S(O₂)— | —S(O₂)— | 0 |
| 30 | CH₃ | CH₃, H | 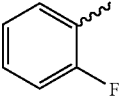 | 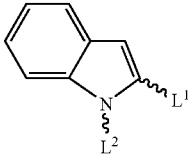 | —CH₂— | —S(O₂)— | —S(O₂)— | 0 |
| 31 | CF₃ | H, H | 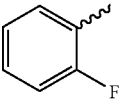 | 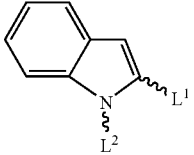 | —S(O₂)— | —S(O₂)— | —S(O₂)— | 0 |
| 32 | CF₃ | CH₃, H | 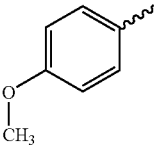 | 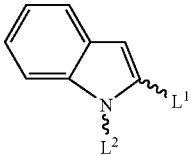 | —C(O)— | —S(O₂)— | —C(O)— | 0 |
| 33 | CF₃ | CH₃, H | 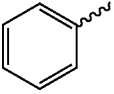 | 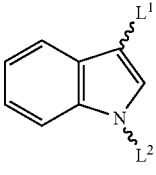 |  | —S(O₂)— | —C(O)— | 0 |
| 34 | CH₃ | CH₃, H | 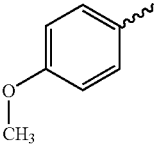 | 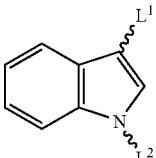 | —C(O)— | —S(O₂)— | —S(O₂)— | 0 |
| 35 | CF₃ | CH₃, CH₃ | 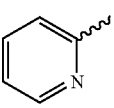 | 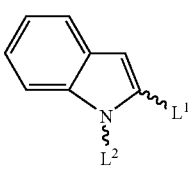 | —S(O₂)— | —S(O₂)— | —S(O₂)— | 0 |

-continued

| # | R¹ | R⁵, R⁶ | R⁴ (with linking point to L²) | M (with linking points to L¹, L² and X) | L¹ | L² | Y | p, X |
|---|---|---|---|---|---|---|---|---|
| 36 | CF₃ | CH₃, H | 3-fluorophenyl | indole (L¹ at 2-position, L² at N) | —S(O₂)— | —S(O₂)— | —S(O₂)— | 0 |
| 37 | CH₃ | CH₃, H | 4-(trifluoromethoxy)phenyl | indole (L¹ at 2-position, L² at N) | —S(O₂)— | —S(O₂)— | —S(O₂)— | 0 |
| 38 | CH₃ | CH₃, H | 4-chlorophenyl | pyridine (L¹ at 3-position, L² at 2-position) | CH=N—O—CH₃ | —O— | —S(O₂)— | 0 |
| 39 |  | H, H | 2-fluorophenyl | indole (L¹ at 2-position, L² at N) | —S(O₂)— | —S(O₂)— | —S(O₂)— | 0 |
| 40 | CF₃ | H, H | 4-chlorophenyl | indole (L¹ at 2-position, L² at N) | —S(O₂)— | —S(O₂)— | —C(O)— | 0 |
| 41 | CF₃ | CH₃, H | 2-chlorophenyl | indole with X at 5-position (L¹ at 2-position, L² at N) | —S(O₂)— | —S(O₂)— | —S(O₂)— | 1, Cl |
| 42 | CH₃ | H, H | 3-chlorophenyl | indole (L¹ at 2-position, L² at N) | —S(O₂)— | —S(O₂)— | —S(O₂)— | 0 |
| 43 | CF₃ | CH₃, H | phenyl | indole (L¹ at 3-position, L² at N) | —C(O)— | —S(O₂)— | —C(O)— | 0 |

-continued

| # | R¹ | R⁵, R⁶ | R⁴ (with linking point to L²) | M (with linking points to L¹, L² and X) | L¹ | L² | Y | p, X |
|---|----|---------|-------------------------------|----------------------------------------|-----|-----|----|------|
| 44 | CH₃ | CH₃, H | 4-methoxyphenyl | indole (L¹ at 2-position, L² at N) | —C(O)— | —S(O₂)— | —S(O₂)— | 0 |
| 45 | CH₃ | CH₃, H | 4-chlorophenyl | pyridine (L¹, L² at 2,3) | —CH₂— | —O— | —S(O₂)— | 0 |
| 46 | CF₃ | CH₃, H | pyridin-3-yl | indole (X at N, L¹ at 5, L² at 4) | —SO₂— | —SO— | —C(O)— | CH₃ |
| 47 | CF₃ | CH₃, H | 2-chlorophenyl | pyridine N-oxide (L¹, L² at 2,3) | —CH₂— | —S(O₂)— | —C(O)— | 0 |
| 48 | CF₃ | CH₃, H | 4-chlorophenyl | pyridine (L¹, L² at 2,3) | —C(O)— | —O— | —C(O)— | 0 |
| 49 | CF₃ | H, H | 4-fluorophenyl | indole (L¹ at 2-position, L² at N) | —S(O₂)— | —S(O₂)— | —S(O₂)— | 0 |
| 50 | CF₃ | H, H | 3-fluorophenyl | indole (L¹ at 2-position, L² at N) | —S(O₂)— | —S(O₂)— | —S(O₂)— | 0 |
| 51 | CF₃ | CH₃, H | 2-fluorophenyl | indole (L¹ at 2-position, L² at N) | —S(O₂)— | —C(O)— | —C(O)— | 0 |
| 52 | CF₃ | CH₃, H | 4-chlorophenyl | pyridine (L¹, L² at 2,3) | —C(O)— | —S— | —C(O)— | 0 |

-continued
| # | R¹ | R⁵, R⁶ | R⁴ (with liking point to L²) | M (with linking points to L¹, L² and X) | L¹ | L² | Y | p, X |
|---|----|---------|------------------------------|------------------------------------------|-----|-----|-----|------|
| 53 | CH₃ | CH₃, H | 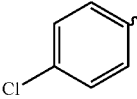 | 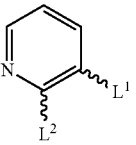 | —C(O)— | —S— | —S(O₂)— | 0 |
| 54 | CF₃ | H, H | 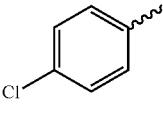 | 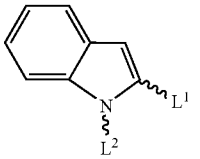 | —S(O₂)— | —S(O₂)— | —S(O₂)— | 0 |
| 55 | CH₃ | H, H | 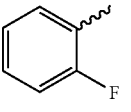 | 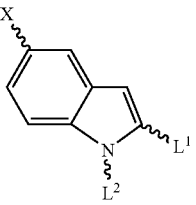 | —S(O₂)— | —CH₂— | —S(O₂)— | 1, F |
| 56 | CH₃ | CH₃, H | 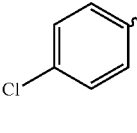 | 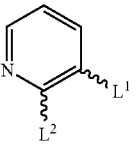 | —C(O)— | —S(O₂)— | —S(O₂)— | 0 |
| 57 | CH₃ | CH₃, H | 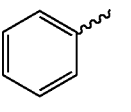 | 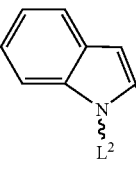 | | | —S(O₂)— | 0 |
| 58 | CH₃ | CH₃, H |  | 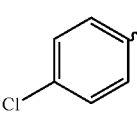 | —S(O₂)— | —CH₂— | —S(O₂)— | 0 |
| 59 | CH₃ | CH₃, H | 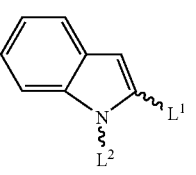 | 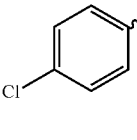 | —C(O)— | —O— | —S(O₂)— | 0 |
| 60 | CH₃ | CH₃, H | 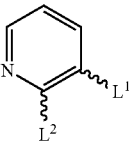 | 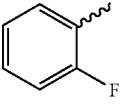 | —S(O₂)— | —C(O)— | —S(O₂)— | 1, Cl |

-continued

| # | R¹ | R⁵, R⁶ | R⁴ (with linking point to L²) | M (with linking points to L¹, L² and X) | L¹ | L² | Y | p, X |
|---|----|--------|-------------------------------|-----------------------------------------|-----|-----|---|------|
| 61 |  | H, H | 4-F-phenyl | indole (L¹, L²) | —S(O₂)— | —S(O₂)— | —S(O₂)— | 0 |
| 62 |  | H, H | 3-F-phenyl | indole (L¹, L²) | —S(O₂)— | —S(O₂)— | —S(O₂)— | 0 |
| 63 | CF₃ | H, H | 3-Cl-phenyl | indole (L¹, L²) | —S(O₂)— | —S(O₂)— | —S(O₂)— | 0 |
| 64 | CF₃ | CH₃, H | 2-pyridyl | 2,3-dihydrobenzofuran (L¹, L²) | —S(O₂)— | —S— | —C(O)— | 0 |
| 65 | CF₃ | H, H | 2-F-phenyl | indole (X, L¹, L²) | —S(O₂)— | —CH₂— | —S(O₂)— | 1, F |
| 66 | 4-Cl-phenyl | CH₃, H | 4-Cl-phenyl | indole (L¹, L²) | —S(O₂)— | —CH₂— | —CH₂— | F. |

9. The compound according to claim 1 having the following formula:

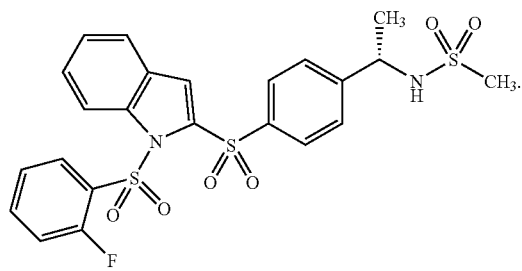

10. The compound according to claim 1 having the following formula:

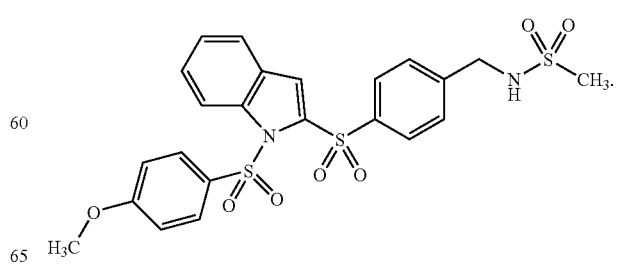

11. The compound according to claim 1 having the following formula:

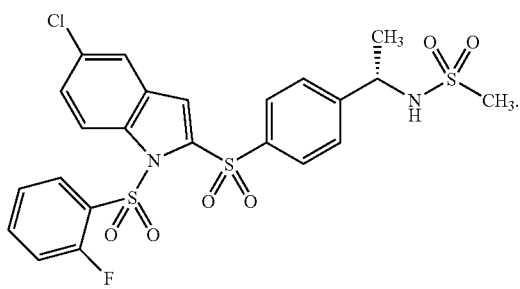

12. The compound according to claim 1 having the following formula:

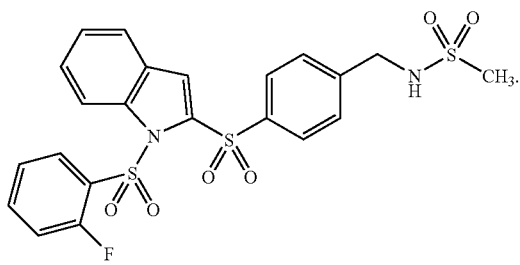

13. The compound according to claim 1 having the following formula:

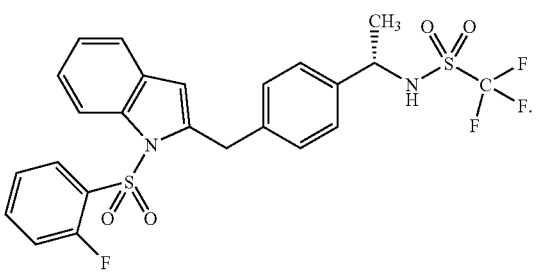

14. The compound according to claim 1 having the following formula:

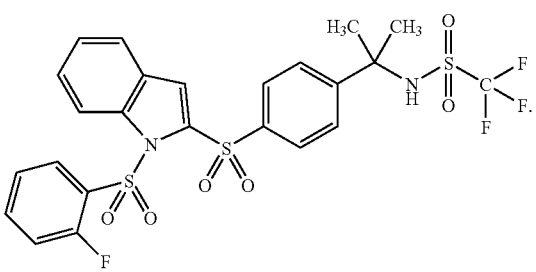

15. The compound according to claim 1 having the following formula:

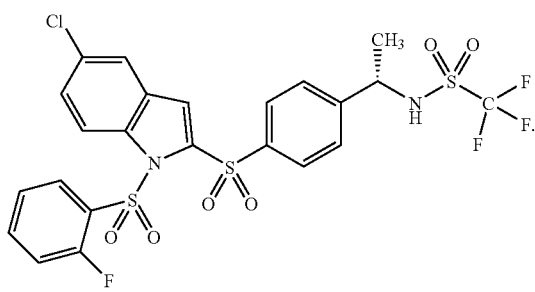

16. The compound according to claim 1 having the following formula:

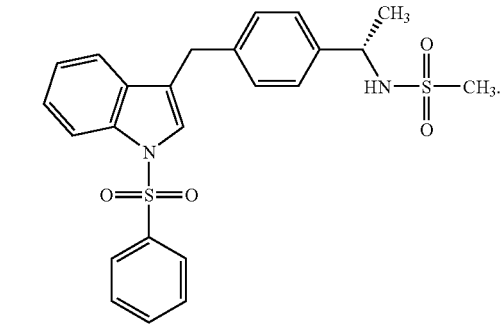

17. The compound according to claim 1 having the following formula:

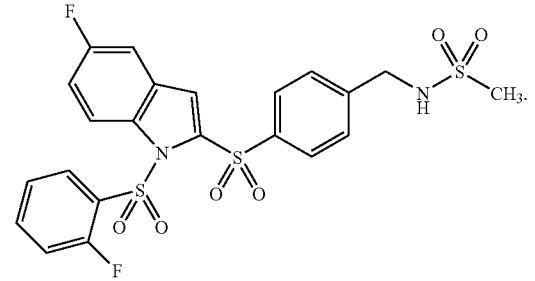

18. The compound according to claim 1 having the following formula:

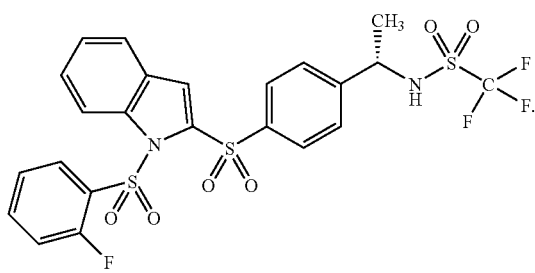

19. The compound according to claim 1 having the following formula:

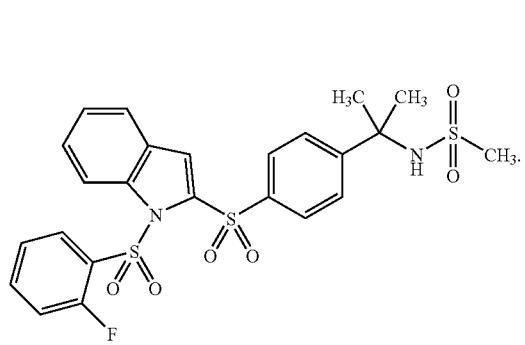

20. The compound according to claim 1 having the following formula:

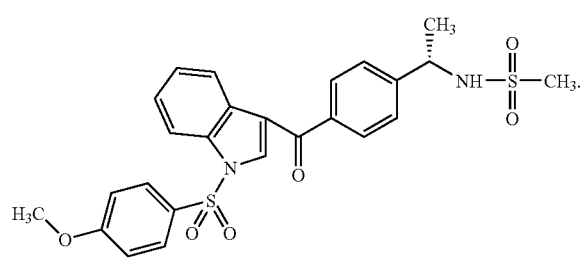

21. The compound according to claim 1 having the following formula:

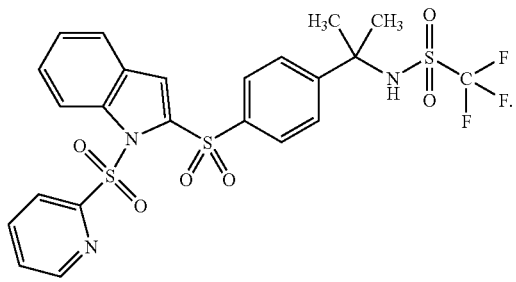

22. The compound according to claim 1 having the following formula:

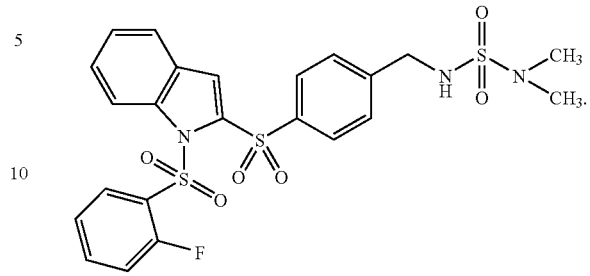

23. The compound according to claim 1 having the following formula:

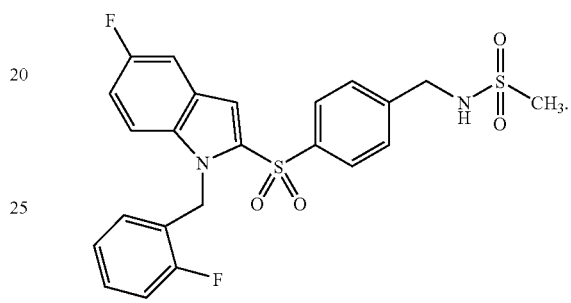

24. The compound according to claim 1 wherein said alkyl is in the various definitions of lower alkyl.

25. A pharmaceutical composition comprising one or more compounds according to claim 1.

26. The pharmaceutical composition according to claim 25, further comprising one or more pharmaceutically acceptable carriers.

27. A method of preparing the pharmaceutical composition of claim 26, said method comprising contacting said one or more compounds of formula I with said one or more pharmaceutically acceptable carriers.

28. The compound according to claim 1 having the following formula:

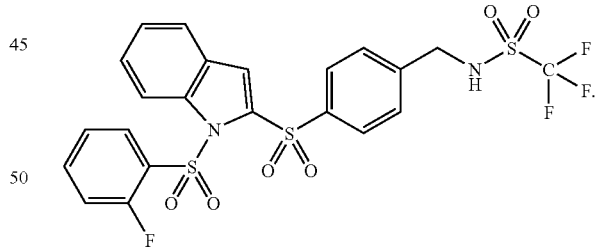

* * * * *

UNITED STATES PATENT AND TRADEMARK OFFICE
CERTIFICATE OF CORRECTION

PATENT NO.        : 7,217,732 B2                                        Page 1 of 1
APPLICATION NO. : 10/464174
DATED             : May 15, 2007
INVENTOR(S)       : Joseph A. Kozlowski It is certified that error appears in the above-identified patent and that said Letters Patent is hereby corrected as shown below:

Claim 1, Formula I, column 95, in line 12 only, delete "R3" and insert --R5-- therefor.

Signed and Sealed this

Sixteenth Day of October, 2007

JON W. DUDAS
*Director of the United States Patent and Trademark Office*